US009461254B2

(12) United States Patent
Tsai et al.

(10) Patent No.: US 9,461,254 B2
(45) Date of Patent: Oct. 4, 2016

(54) ORGANIC ELECTROLUMINESCENT MATERIALS AND DEVICES

(71) Applicant: Universal Display Corporation, Ewing, NJ (US)

(72) Inventors: Jui-Yi Tsai, Ewing, NJ (US); Gregg Kottas, Ewing, NJ (US); Jason Brooks, Ewing, NJ (US); Walter Yeager, Ewing, NJ (US); Nasrin Ansari, Ewing, NJ (US); Edward Barron, Ewing, NJ (US); Chuanjun Xia, Ewing, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 572 days.

(21) Appl. No.: 13/732,502

(22) Filed: Jan. 2, 2013

(65) Prior Publication Data

US 2013/0168656 A1 Jul. 4, 2013

Related U.S. Application Data

(60) Provisional application No. 61/582,691, filed on Jan. 3, 2012.

(51) Int. Cl.
| | |
|---|---|
| *H01L 51/54* | (2006.01) |
| *C09K 11/06* | (2006.01) |
| *H01L 51/00* | (2006.01) |
| *H01L 51/52* | (2006.01) |
| *C07F 15/00* | (2006.01) |
| *H01L 51/50* | (2006.01) |

(52) U.S. Cl.
CPC ....... *H01L 51/0087* (2013.01); *C07F 15/0086* (2013.01); *C09K 11/06* (2013.01); *H01L 51/0032* (2013.01); *H01L 51/0094* (2013.01); *H01L 51/5206* (2013.01); *C09K 2211/1029* (2013.01); *C09K 2211/1044* (2013.01); *C09K 2211/185* (2013.01); *H01L 51/0058* (2013.01); *H01L 51/0072* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

(Continued)

*Primary Examiner* — Marie R. Yamnitzky
(74) *Attorney, Agent, or Firm* — Duane Morris LLP

(57) ABSTRACT

Novel phosphorescent platinum complexes containing tetradentate ligands are provided. The disclosed compounds have three 6-membered metallocycle units in each tertadentate ligand. The disclosed compounds have desirable electronic properties that make them useful when incorporated into a variety of OLED devices.

29 Claims, 3 Drawing Sheets

Formula I

(56) References Cited

U.S. PATENT DOCUMENTS

| | | |
|---|---|---|
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,893,743 B2 * | 5/2005 | Sato et al. .............. 428/690 |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 7,655,323 B2 * | 2/2010 | Walters et al. ...... C07D 487/22 257/E51.044 |
| 7,781,074 B2 * | 8/2010 | Sano et al. .............. 428/690 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0172146 A1 * | 8/2006 | Igarashi et al. ............ 428/690 |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0140602 A1 * | 6/2010 | Sotoyama ........... H01L 51/5036 257/40 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | WO 2009/030981 A2 * | 3/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | WO 2014/031977 A1 * | 2/2014 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3, (2007).

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

(56) References Cited

OTHER PUBLICATIONS

Hamada, Yuji et al., "High Luminance in Organic Electroluminescent Devices with Bis(10-hydroxybenzo[h]quinolinato) beryllium as an Emitter," Chem. Lett., 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater, 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al.,"1,2,4-Triazole Derivative as an Electron Transport Layer in Organic Electroluminescent Devices," Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164.
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15)2280-2282 (2000).
Lo, Shih-Chun et al., "Blue Phosphorescence from Iridium(III) Complexes at Room Temperature," Chem. Mater., 18(21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis(dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on p-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing $N^{\wedge}C^{\wedge}N$-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 87:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al.,"A Novel Class of Phosphorescent Gold(III)Alkynyl-Based Organic Light-Emitting Devices with Tunable Colour," Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

Formula I

ORGANIC ELECTROLUMINESCENT MATERIALS AND DEVICES

CROSS REFERENCE TO RELATED APPLICATIONS

This application claims the benefit under 35 U.S.C. §119 (e) of U.S. Provisional Application No. 61/582,691 filed Jan. 3, 2012, the disclosure of which is incorporated herein by reference in its entirety.

JOINT RESEARCH AGREEMENT

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD

The present invention relates to cyclometallated tetradentate platinum complexes. The complexes are suitable for use in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine)iridium, denoted Ir(ppy)$_3$, which has the following structure:

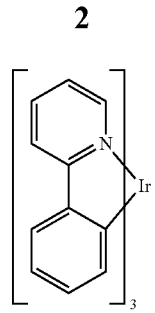

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the formula:

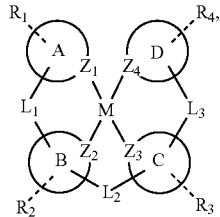

Formula I, is provided. In the compound of Formula I, rings A, B, C and D are each independently a 5- or 6-membered carbocyclic or heterocyclic ring, M is Pt or Pd, $L_1$ and $L_3$ are independently selected from the group consisting of BR, NR, PR, CRR', SiRR', and GeRR', $L_2$ is independently selected from the group consisting of BR, NR, PR, O, S, Se, C=O, S=O, $SO_2$, CRR', SiRR', and GeRR'. $Z_1$, $Z_2$, $Z_3$ and $Z_4$ are carbon or nitrogen and at least one of $Z_2$ and $Z_3$ is carbon. $R_1$, $R_2$, $R_3$ and $R_4$, may represent mono-, di-, tri-, tetra-substitutions, or no substitution, and R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two or more adjacent R, R', $R_1$, $R_2$, $R_3$ and $R_4$ are optionally joined to form a fused ring.

In one aspect, the least one fused ring is formed by joining at least one of R and R' with its adjacent substituents. In one aspect, at least one of $L_1$, $L_2$ and $L_3$ is NR. In one aspect, $L_1$ and $L_3$ are NR.

In one aspect, at least two of $Z_1$, $Z_2$, $Z_3$, and $Z_4$ are nitrogen atoms. In another aspect, at least two of $Z_1$, $Z_2$, $Z_3$, and $Z_4$ are carbon atoms. In one aspect, M is Pt.

In one aspect, A-$L_1$-B is selected from the group consisting of:

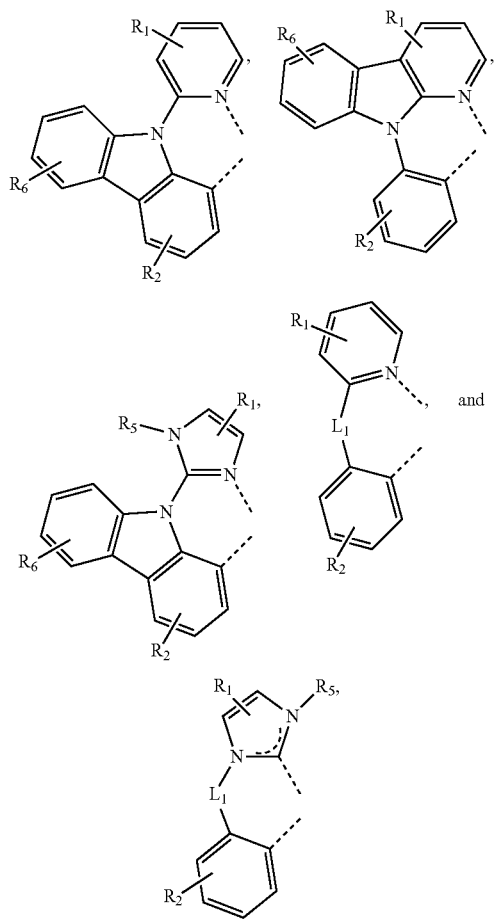

wherein $R_5$ and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the compound has the formula:

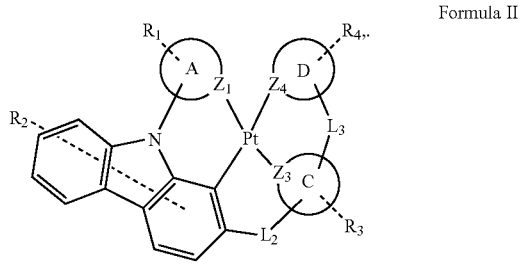

Formula II

In one aspect, the compound has the formula:
Formula III
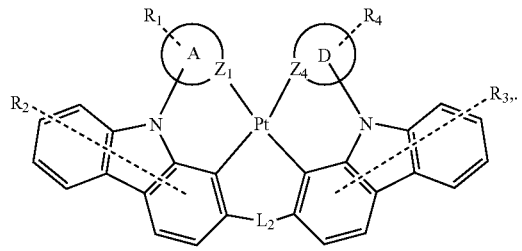
In aspect, the compound has the formula:
Formula IV
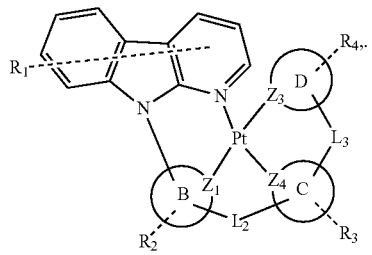
In one aspect, the compound has the formula:
Formula V
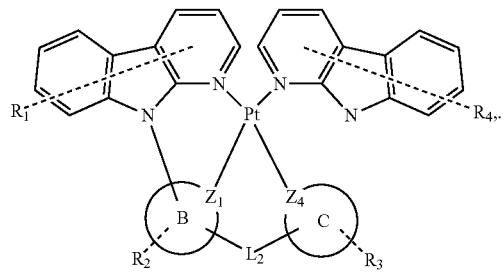
In one aspect, the compound is selected from the group consisting of:
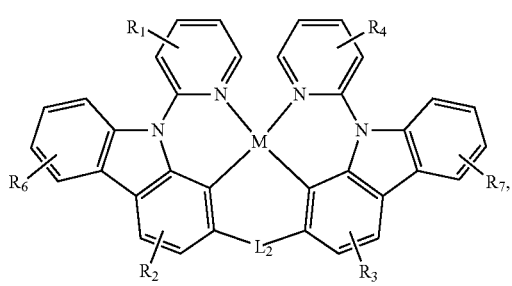
-continued
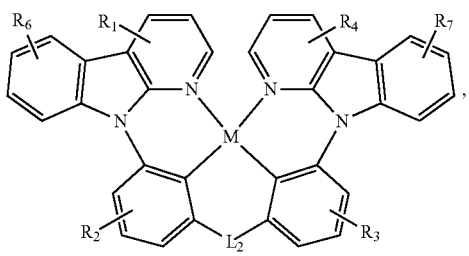
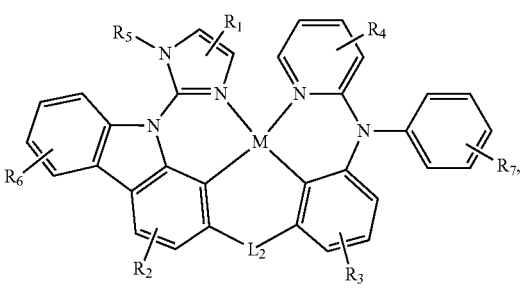

-continued

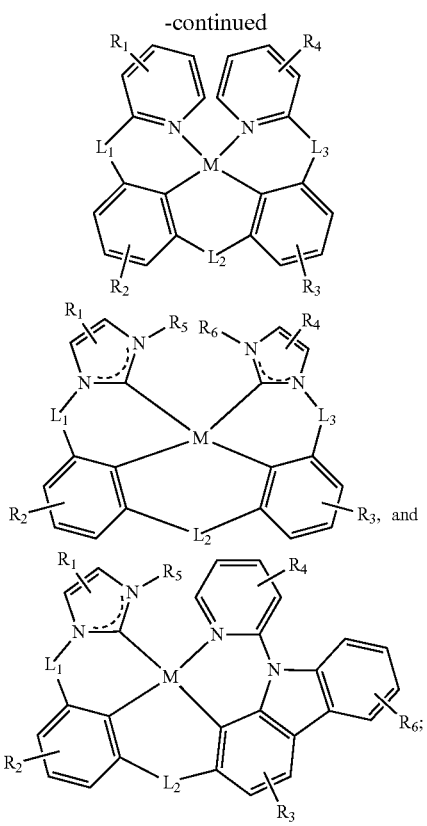

wherein $R_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In aspect, $L_2$ is independently selected from the group consisting of O, S, and NR. In one aspect, $L_2$ is NR, and R is phenyl or substituted phenyl. In one aspect, $L_2$ is O. In one aspect, $Z_1$ and $Z_4$ are nitrogen atoms.

In one aspect, the compound is selected from the group consisting of Compound 1-Compound 132.

In one aspect, a first device is provided. The first device comprises a first organic light emitting device, further comprising an anode, a cathode, and an organic layer, disposed between the anode and the cathode, comprising a compound having the formula:

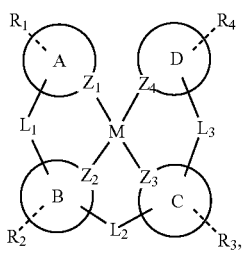

Formula I. In the compound of Formula I, rings A, B, C and D are each independently a 5- or 6-membered carbocyclic or heterocyclic ring, M is Pt or Pd, $L_1$ and $L_3$ are independently selected from the group consisting of BR, NR, PR, CRR', SiRR', and GeRR', $L_2$ is independently selected from the group consisting of BR, NR, PR, O, S, Se, C=O, S=O, $SO_2$, CRR', SiRR', and GeRR'. $Z_1$, $Z_2$, $Z_3$ and $Z_4$ are carbon or nitrogen and at least one of $Z_2$ and $Z_3$ is carbon. $R_1$, $R_2$, $R_3$ and $R_4$, may represent mono-, di-, tri-, tetra-substitutions, or no substitution, and R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two or more adjacent R, R', $R_1$, $R_2$, $R_3$ and $R_4$ are optionally joined to form a fused ring.

In one aspect, the first device is a consumer product. In one aspect, the first device is an organic light-emitting device. In one aspect, the first device comprises a lighting panel.

In one aspect, the organic layer is an emissive layer and the compound is an emissive dopant. In one aspect, the organic layer is an emissive layer and the compound is an non-emissive dopant.

In one aspect, the organic layer further comprises a host. In one aspect, the host comprises a triphenylene containing benzo-fused thiophene or benzo-fused furan. Any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CHC_nH_{2n+1}$, $Ar_1$, $Ar_1-Ar_2$, $C_nH_{2n}-Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10.

In one aspect, the host comprises one or more compounds having the formula:

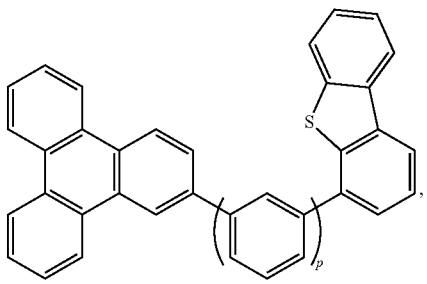

wherein p is 0 or 1.

In one aspect, the host is selected from the group consisting of

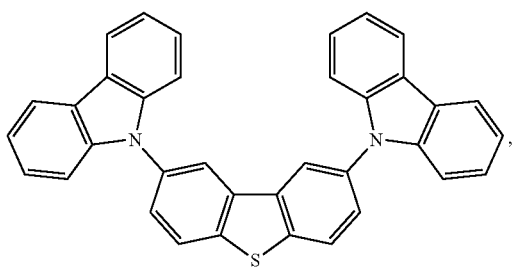

-continued

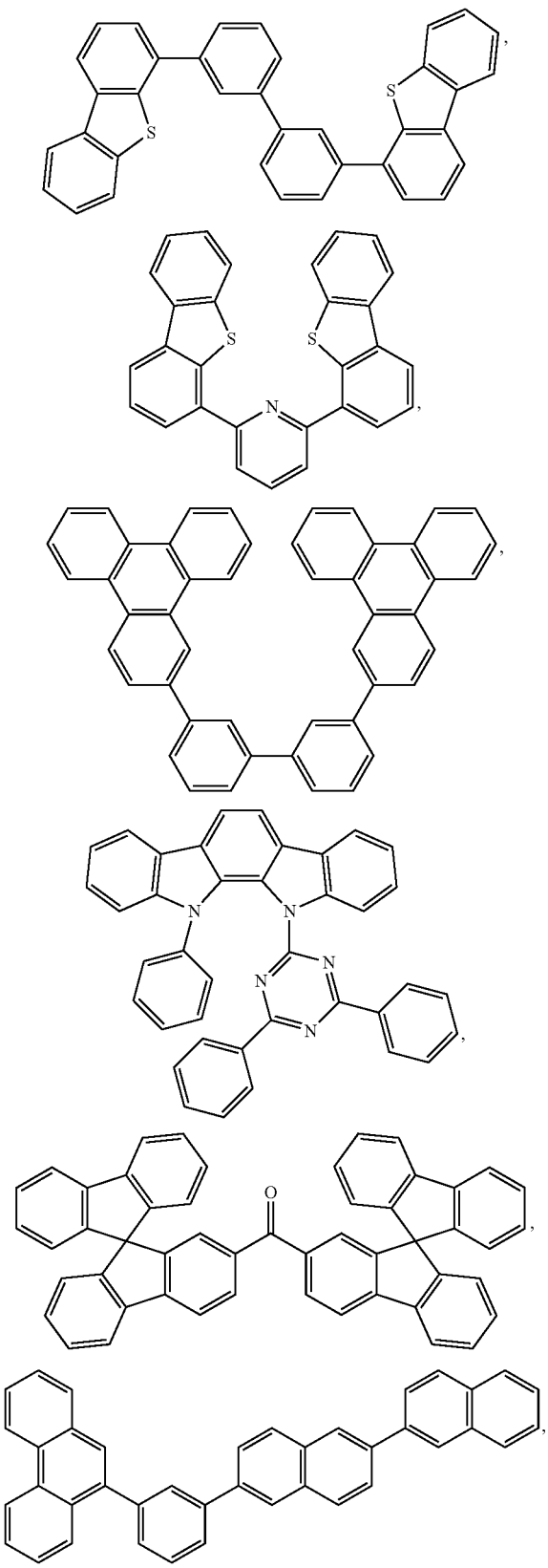

and combinations thereof.

In one aspect, the host comprises a metal complex.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
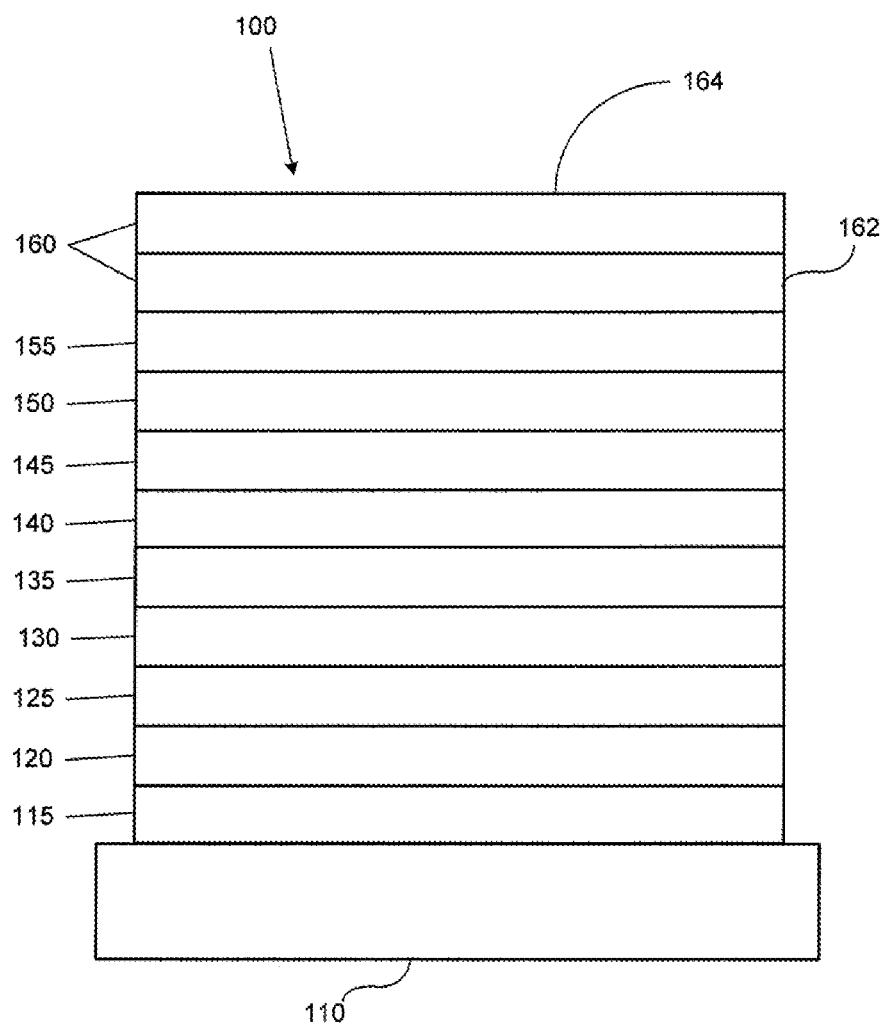
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
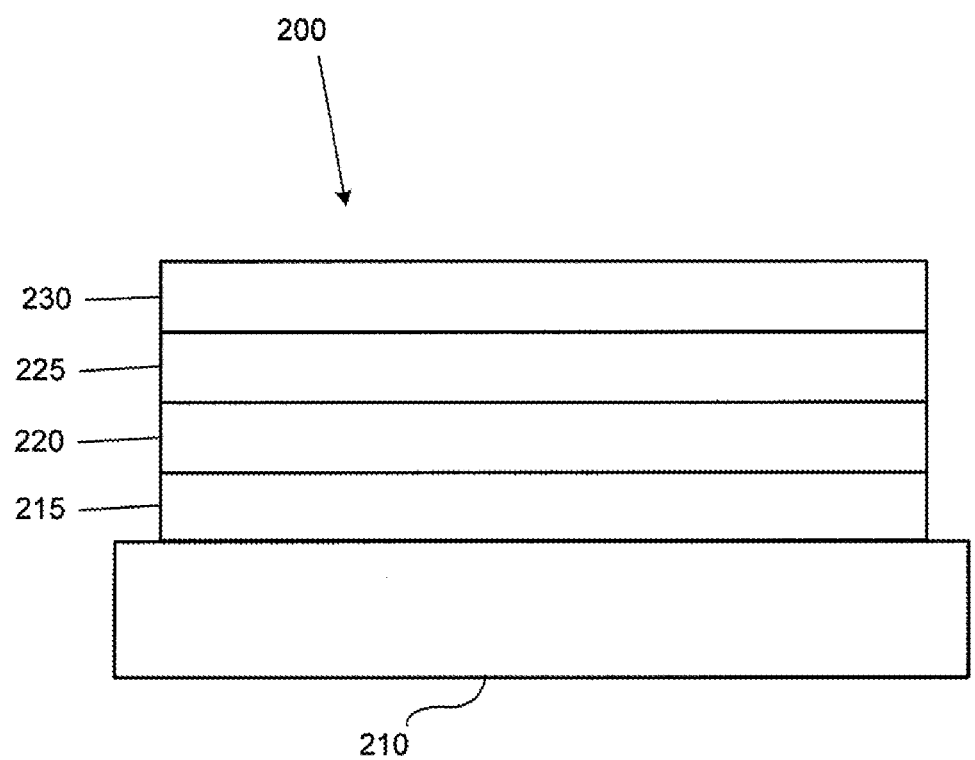
FIG. 2 shows an inverted organic light emitting device that does not have a separate electron transport layer.
Figure 3:
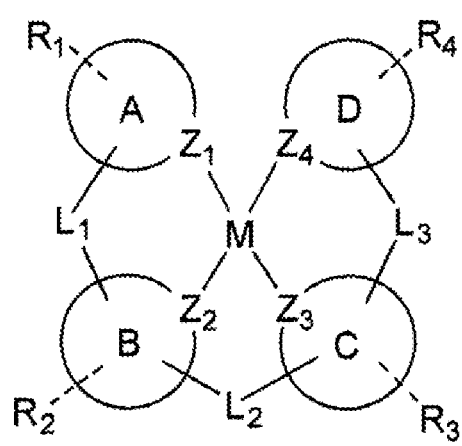
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, now U.S. Pat. No. 7,431,968, which, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the formula:

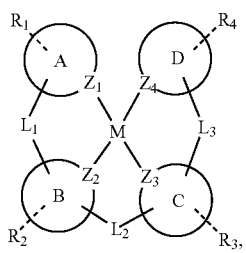

Formula I is provided. In the compound of Formula I, rings A, B, C and D are each independently a 5- or 6-membered carbocyclic or heterocyclic ring, M is Pt or Pd, $L_1$ and $L_3$ are independently selected from the group consisting of BR, NR, PR, CRR', SiRR', and GeRR', $L_2$ is independently selected from the group consisting of BR, NR, PR, O, S, Se, C=O, S=O, $SO_2$, CRR', SiRR', and GeRR'. $Z_1$, $Z_2$, $Z_3$ and $Z_4$ are carbon or nitrogen and at least one of $Z_2$ and $Z_3$ is carbon. $R_1$, $R_2$, $R_3$ and $R_4$, may represent mono-, di-, tri-, tetra-substitutions, or no substitution, and R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two or more adjacent R, R', $R_1$, $R_2$, $R_3$ and $R_4$ are optionally joined to form a fused ring.

$Z_1$, $Z_2$, $Z_3$, and $Z_4$ are atoms in rings A, B, C, and D, respectively, that bond directly with metal M.

It has been unexpectedly discovered that compounds of Formula I, which contain three 6-membered metallocycle units have particularly desirable properties. The three 6-membered metallocycles are illustrated below in FIG. 1 (the metallocycle units are in bold). Metallocycle 1 contains a ring comprising the following sequence of atoms: Pt—N—C—N—C—C, metallocycle 2 contains a ring comprising the following sequence of atoms: Pt—C—C—O—C—C, and finally metallocycle 3 contains a ring comprising the following sequence of atoms: Pt—C—C—N—C—N. FIG. 1 is intended to be merely illustrative, and the particular atoms in each of the metallocycle units can be as described above in the compounds of Formula I. As discussed below, the compounds of Formula I have unexpectedly small calculated HOMO-LUMO energy gaps and high triplet energies.

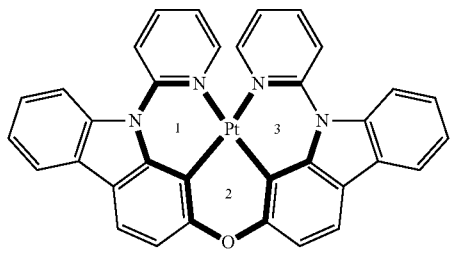

FIG. 1. Illustration of Three 6-Membered Metallocycle Units.

In one embodiment, the least one fused ring is formed by joining at least one of R and R' with its adjacent substituents.

In one embodiment, at least one of $L_1$, $L_2$ and $L_3$ is NR. In one embodiment, $L_1$ and $L_3$ are NR.

In one embodiment, at least two of $Z_1$, $Z_2$, $Z_3$, and $Z_4$ are nitrogen atoms. In another embodiment, at least two of $Z_1$, $Z_2$, $Z_3$, and $Z_4$ are carbon atoms. In one embodiment, M is Pt.

In one embodiment, A-$L_1$-B is selected from the group consisting of:

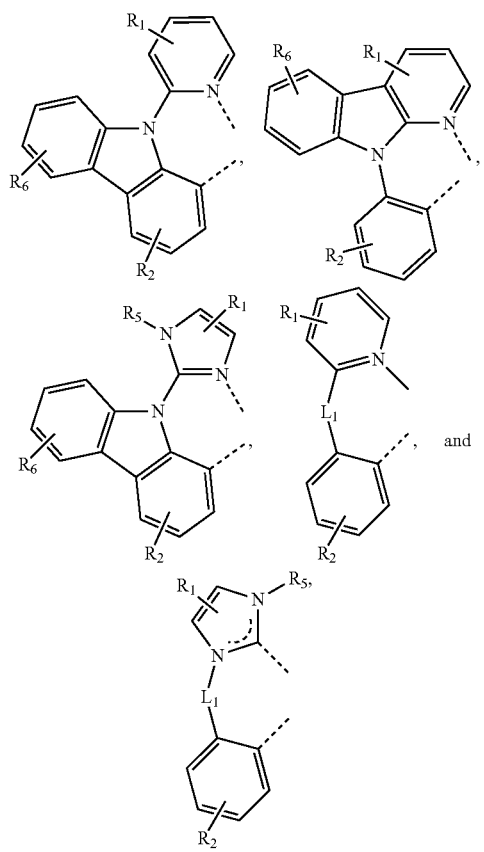

wherein $R_5$ and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. In another embodiment, D-$L_3$-C can be any of the A-$L_1$-B groups described above.

In one embodiment, the compound has the formula:

Formula II

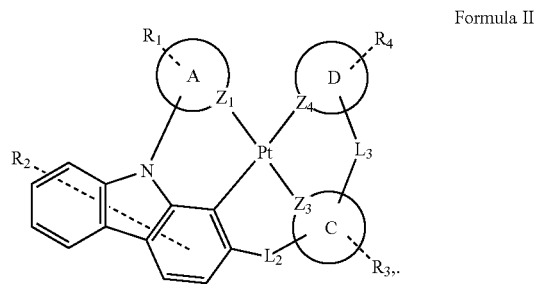

In one embodiment, the compound has the formula:
Formula III
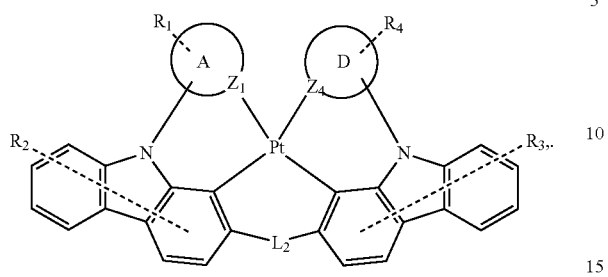
In embodiment, the compound has the formula:
Formula IV
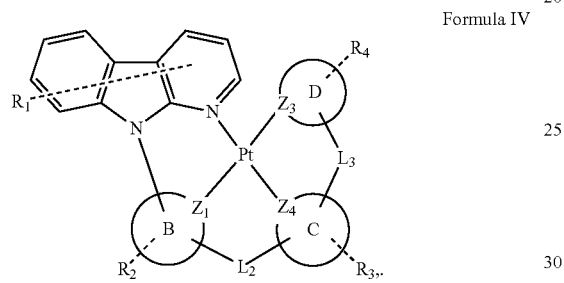
In one embodiment, the compound has the formula:
Formula V
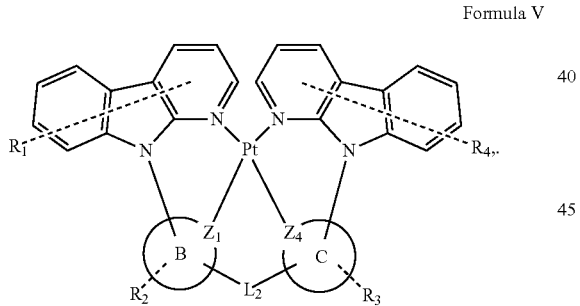
In one embodiment, the compound is selected from the group consisting of:
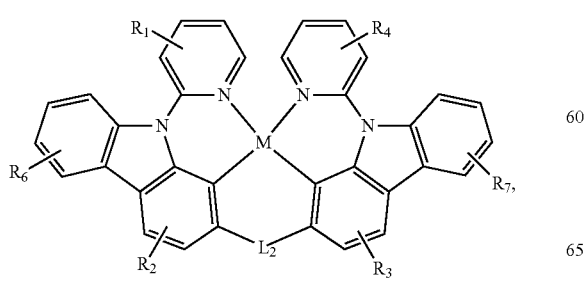
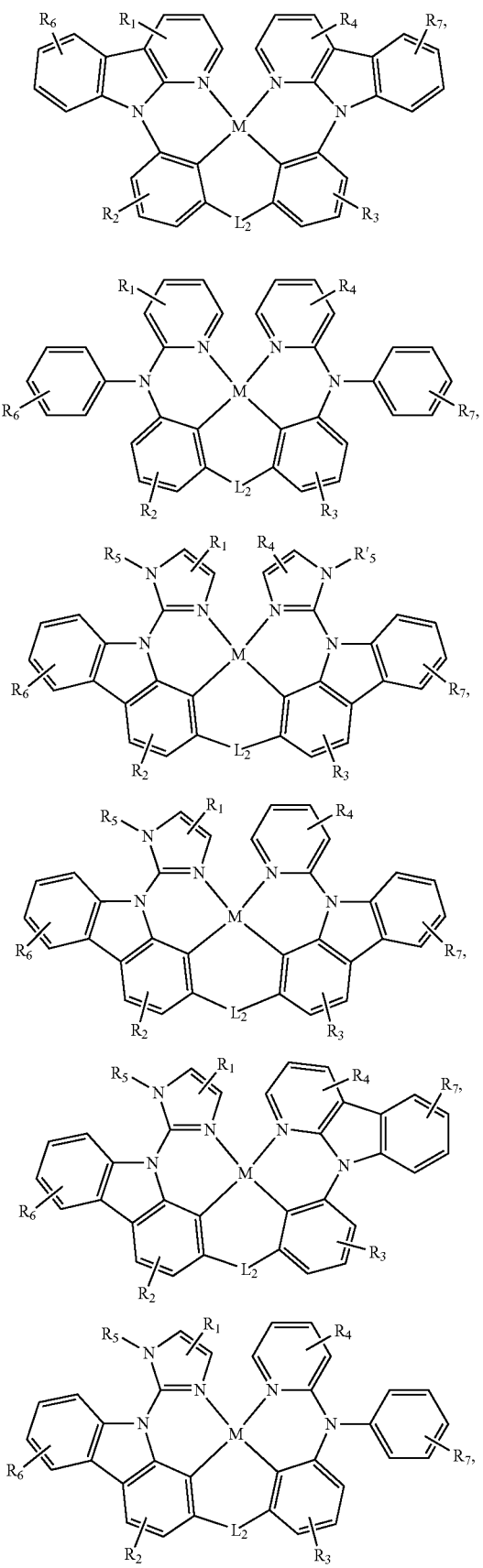

-continued

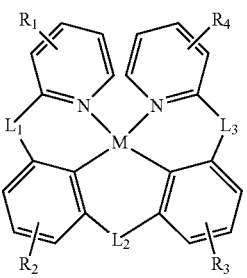

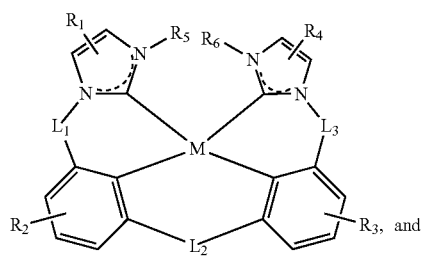

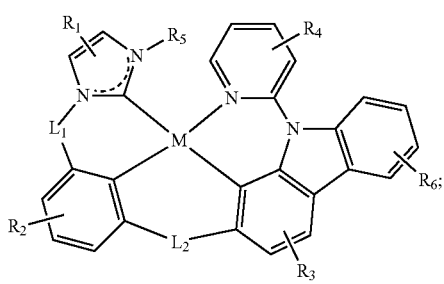

wherein $R_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In embodiment, $L_2$ is independently selected from the group consisting of O, S, and NR. In one embodiment, $L_2$ is NR, and R is phenyl or substituted phenyl. In one embodiment, $L_2$ is O. In one embodiment, $Z_1$ and $Z_4$ are nitrogen atoms.

In one embodiment, the compound is selected from the group consisting of:

Compound 1

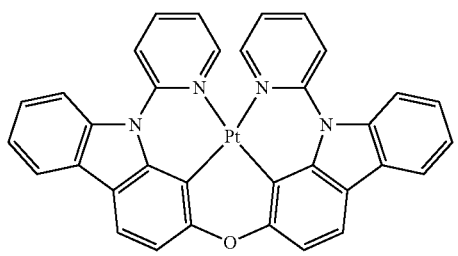

Compound 2

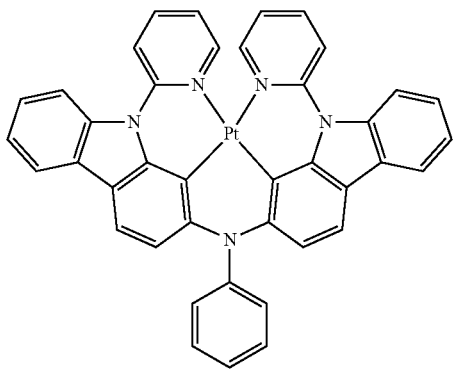

Compound 3

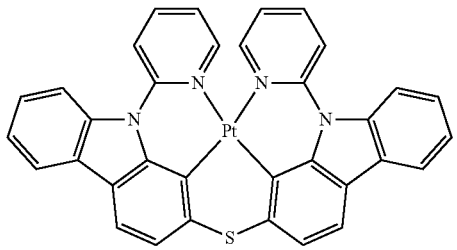

Compound 4

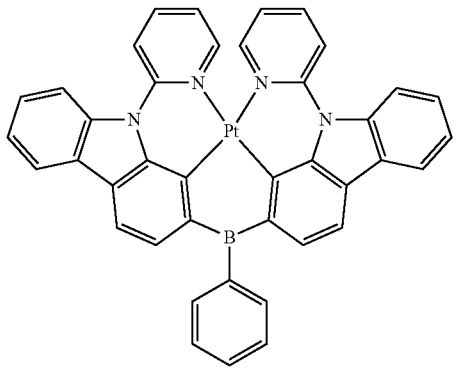

Compound 5

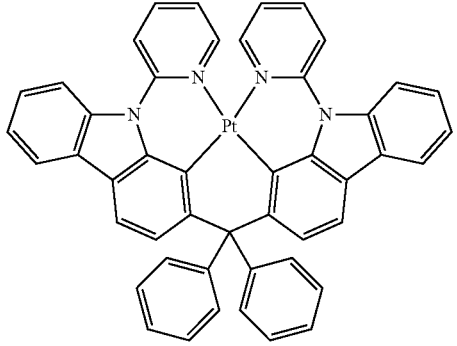

-continued
Compound 6
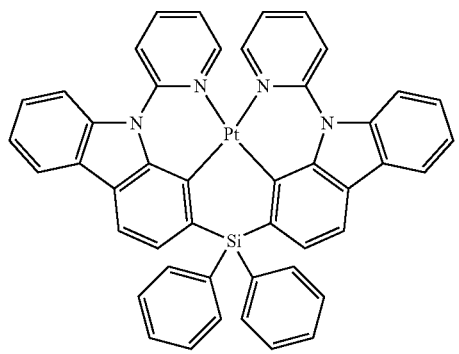
Compound 7
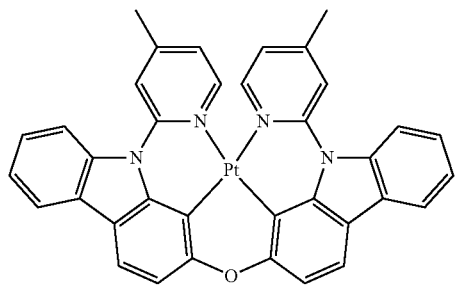
Compound 8
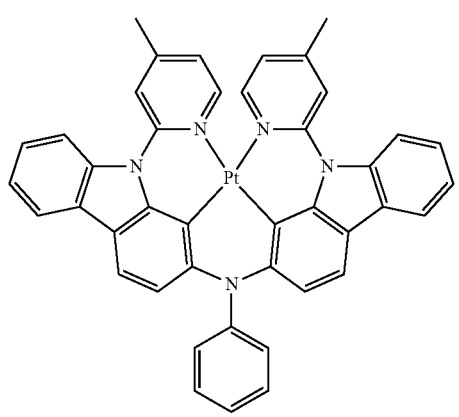
Compound 9
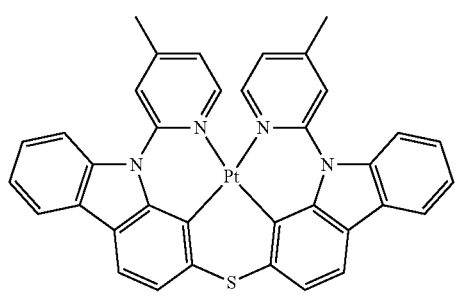
Compound 10
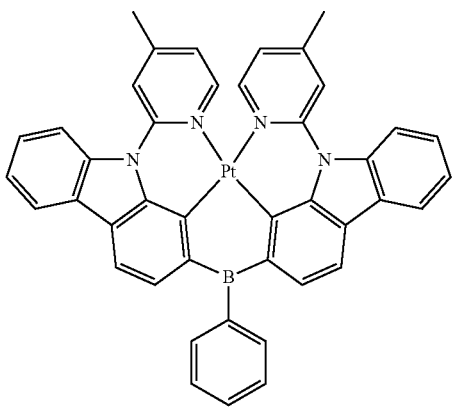
Compound 11
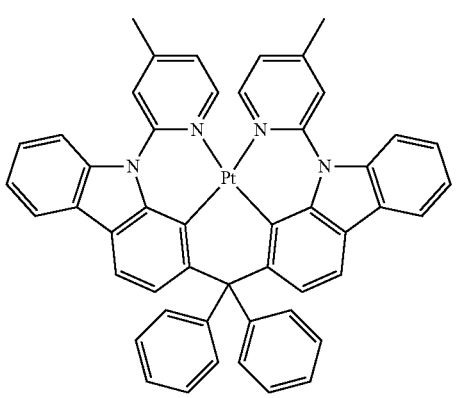
Compound 12
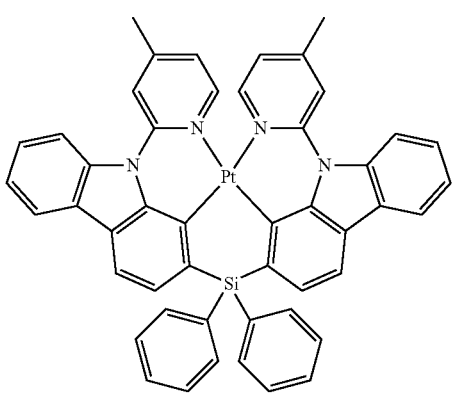
Compound 13
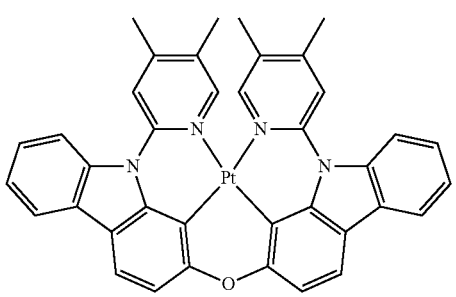

Compound 14
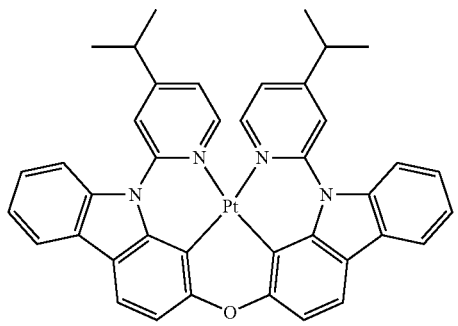
Compound 15
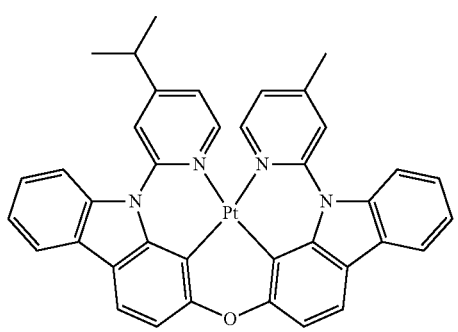
Compound 16
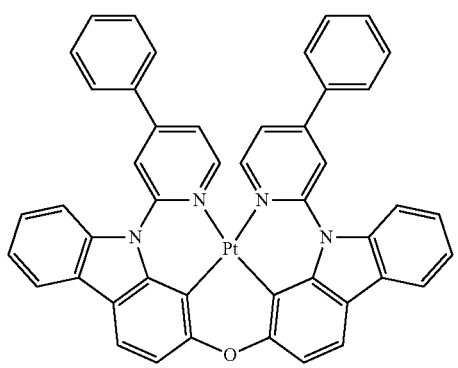
Compound 17
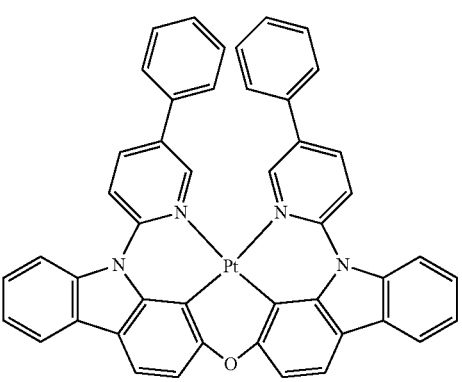
Compound 18
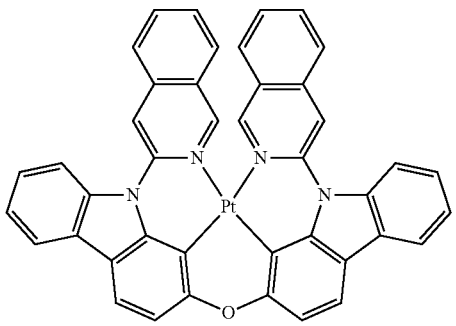
Compound 19
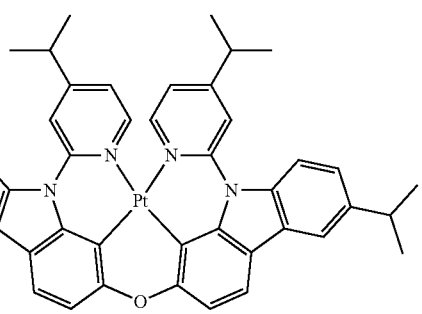
Compound 20
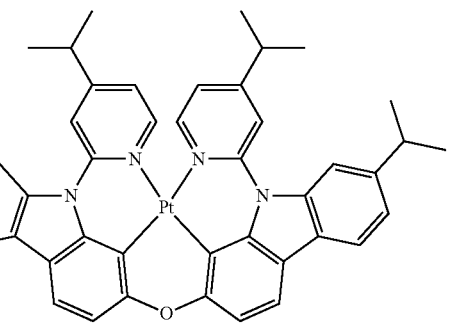
Compound 21
Compound 22
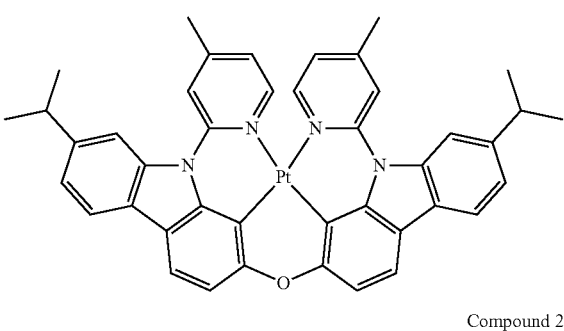

Compound 23
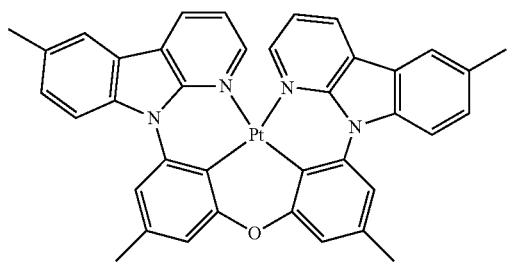
Compound 24
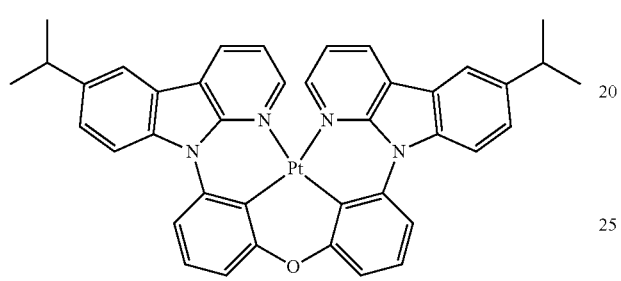
Compound 25
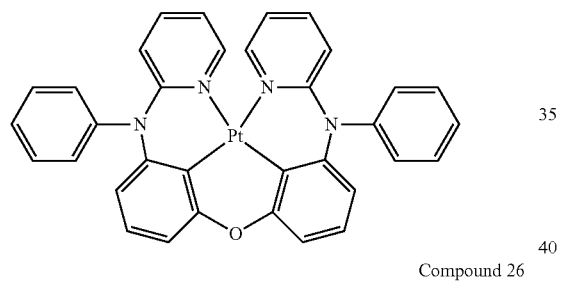
Compound 26
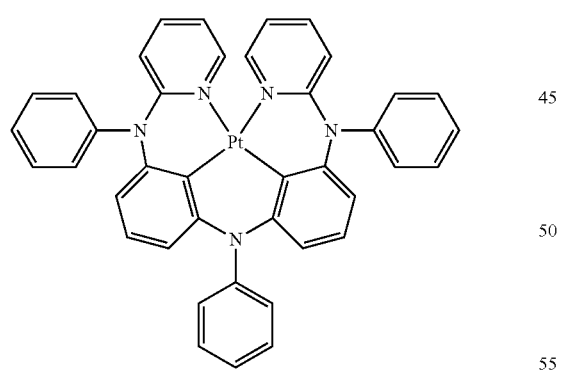
Compound 27
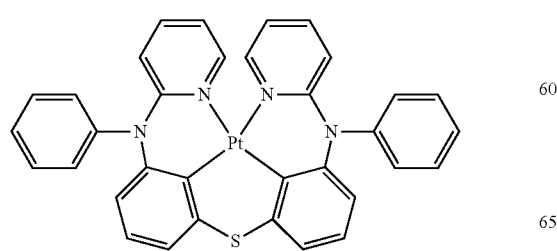
Compound 28
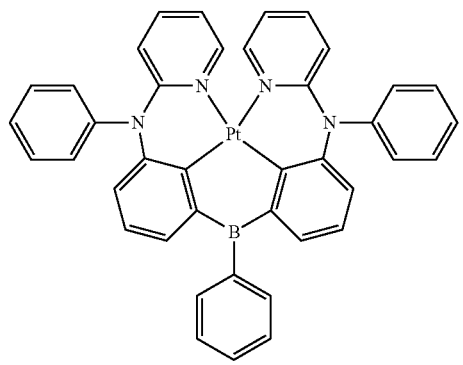
Compound 29
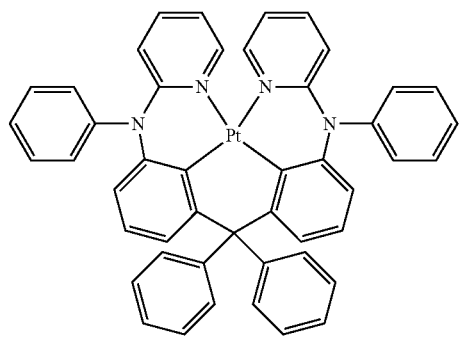
Compound 30
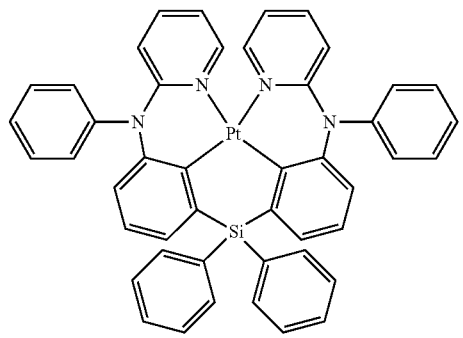
Compound 31
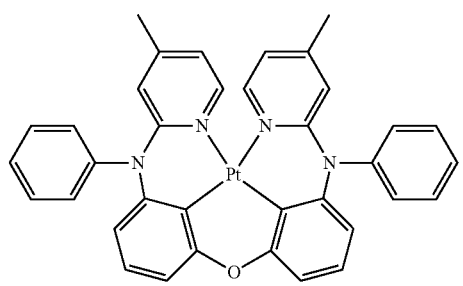

-continued
Compound 32
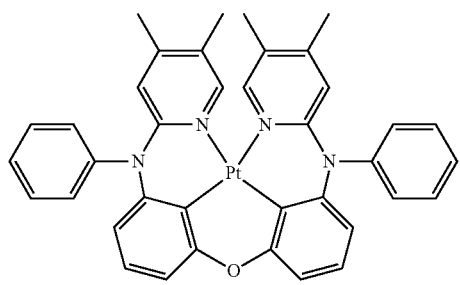
Compound 33
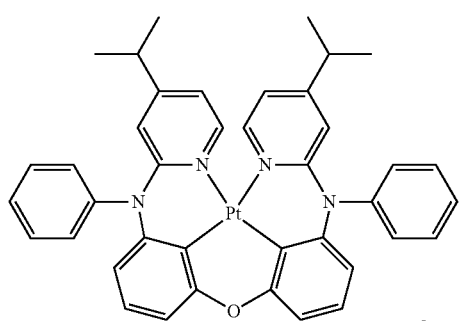
Compound 34
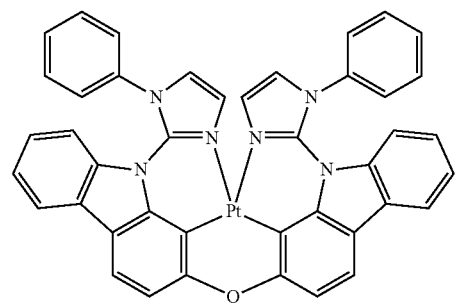
Compound 35
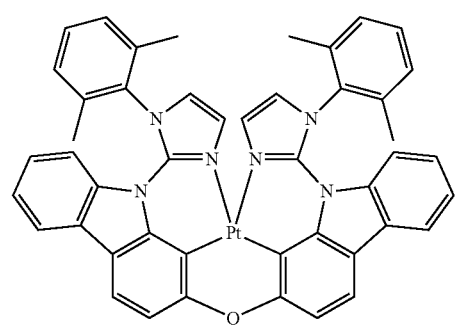
Compound 36
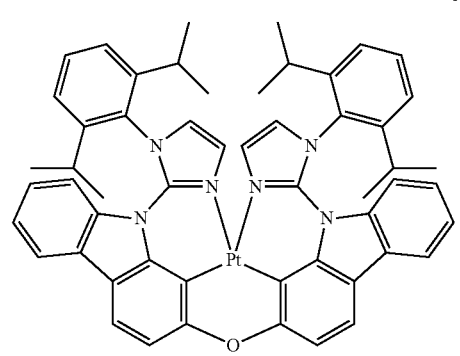
-continued
Compound 37
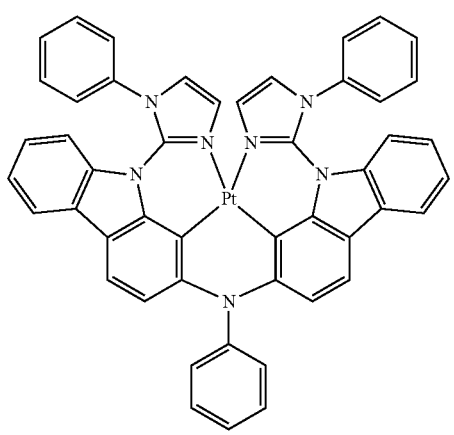
Compound 38
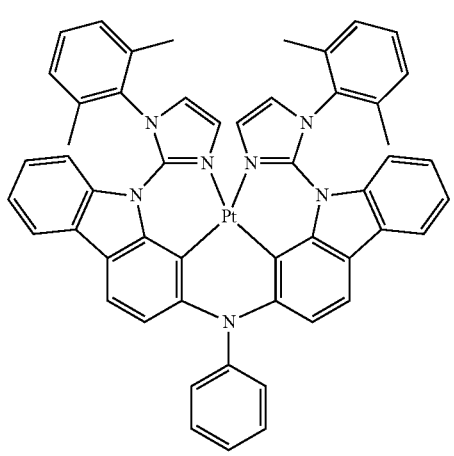
Compound 39
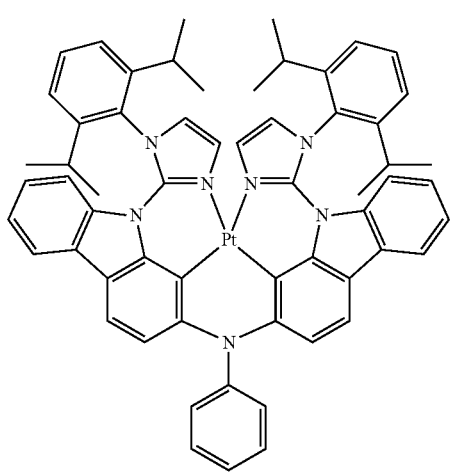

Compound 40
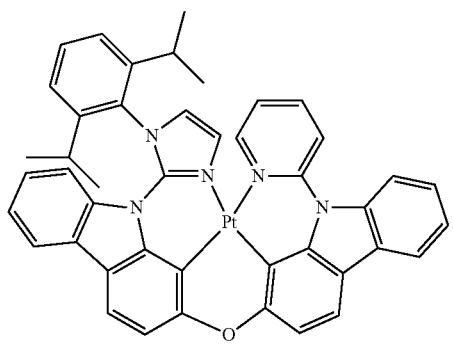
Compound 41
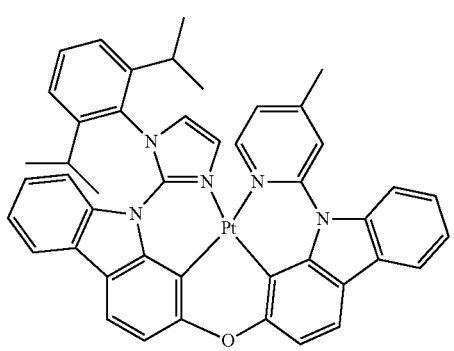
Compound 42
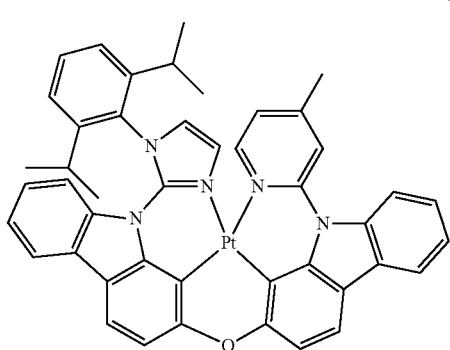
Compound 43
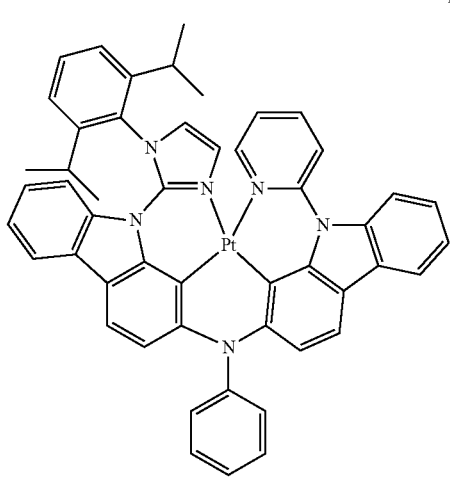
Compound 44
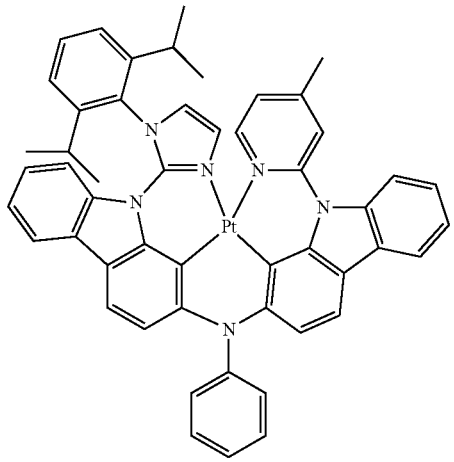
Compound 45
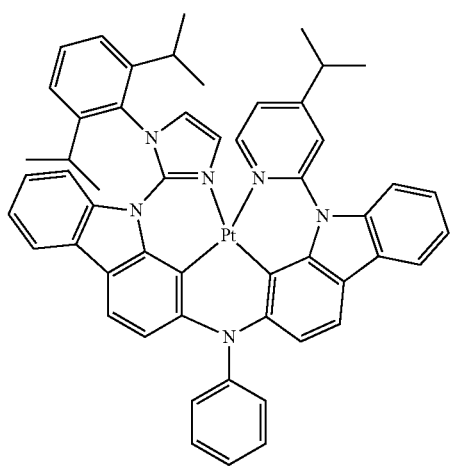
Compound 46
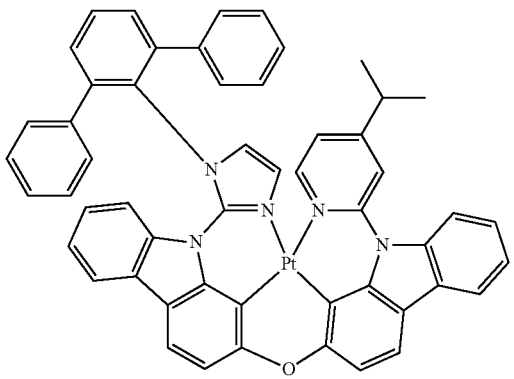

Compound 47
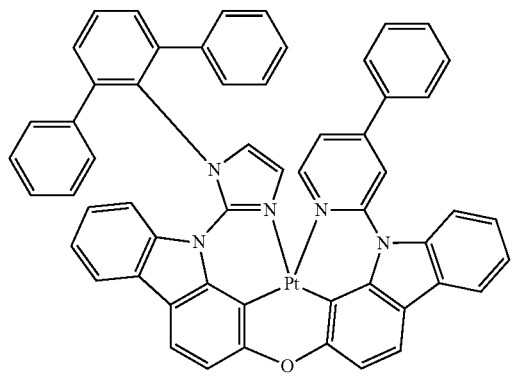
Compound 48
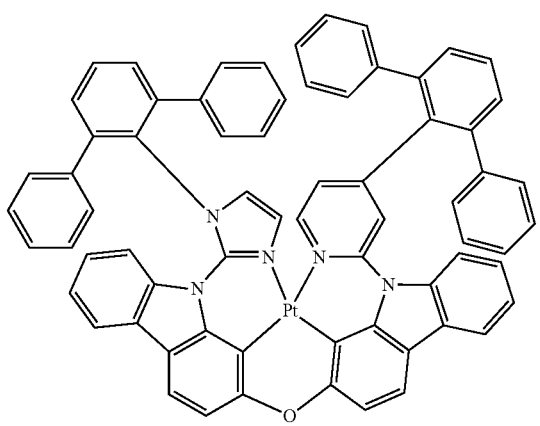
Compound 49
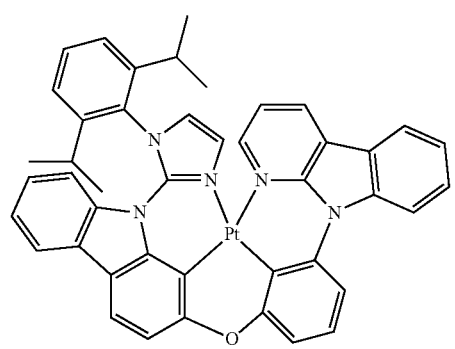
Compound 50
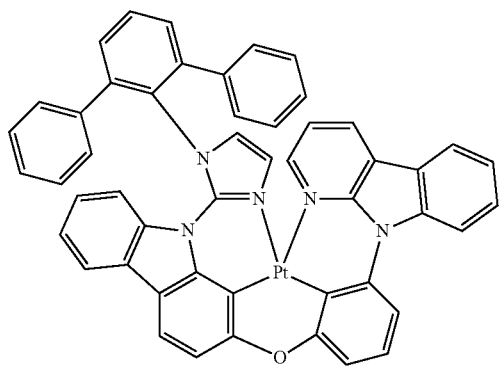
Compound 51
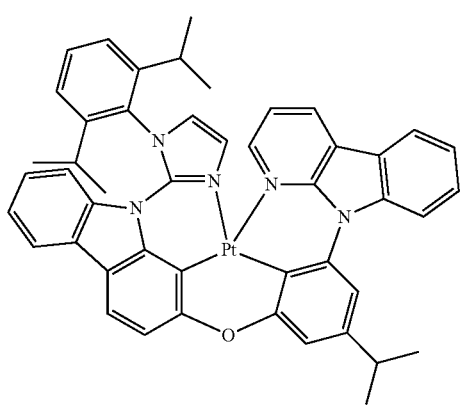
Compound 52
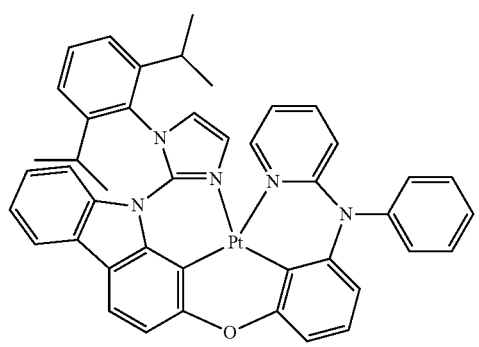
Compound 53
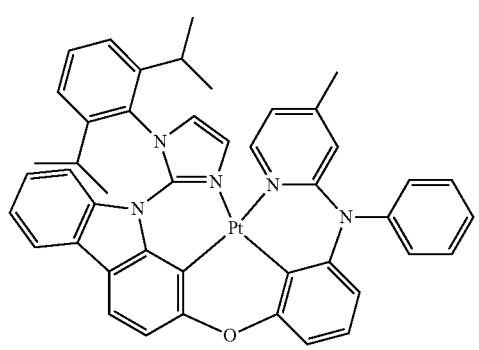
Compound 54
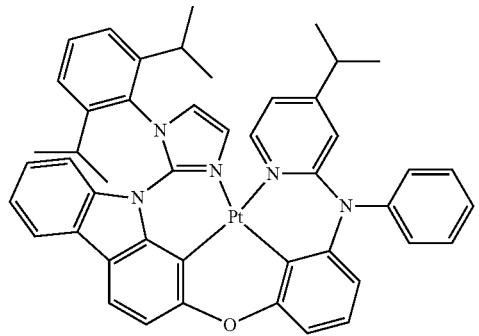

Compound 55
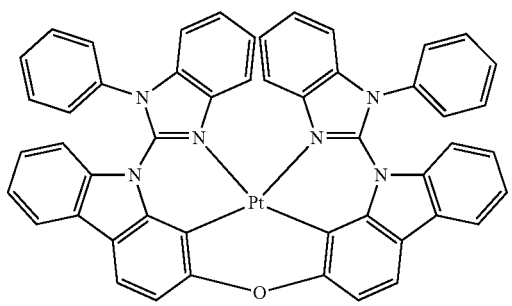
Compound 56
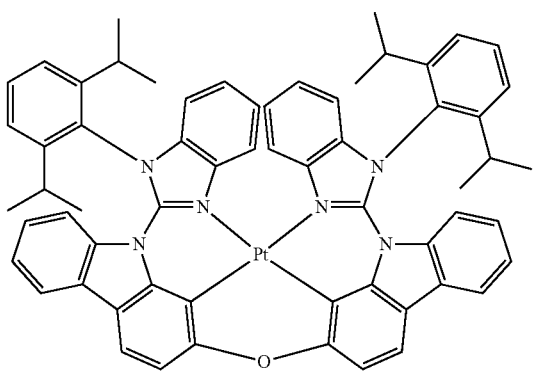
Compound 57
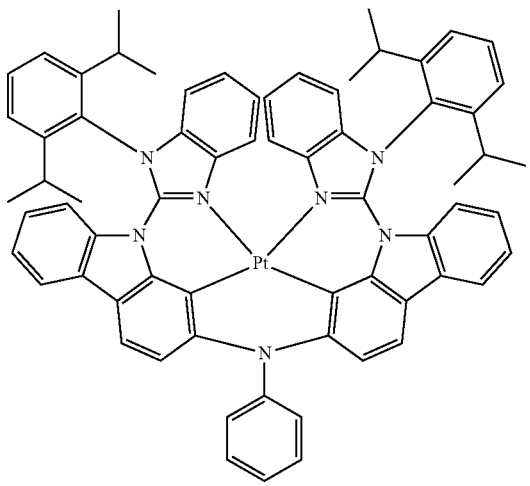
Compound 58
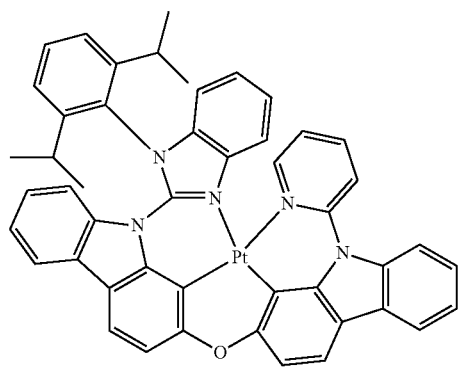
Compound 59
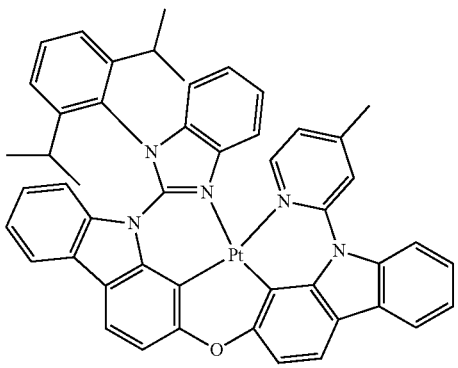
Compound 60
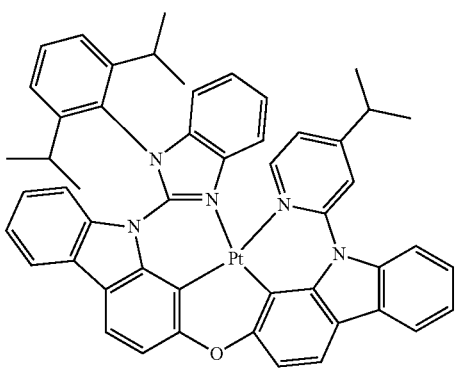
Compound 61
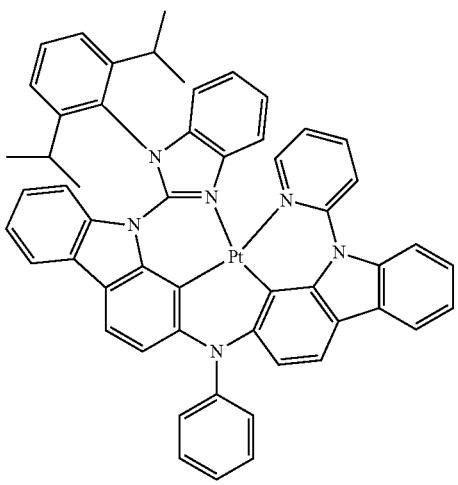

-continued
Compound 62
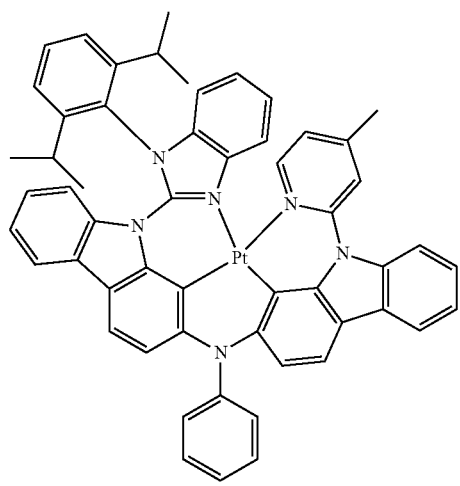
Compound 63
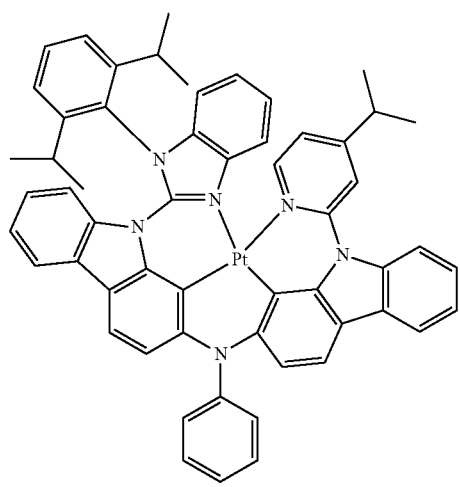
Compound 64
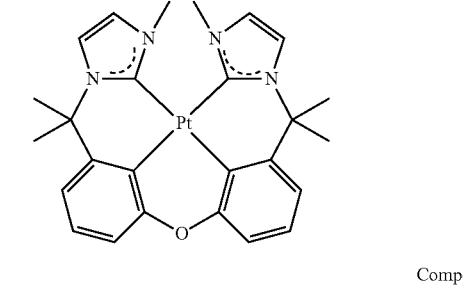
Compound 65
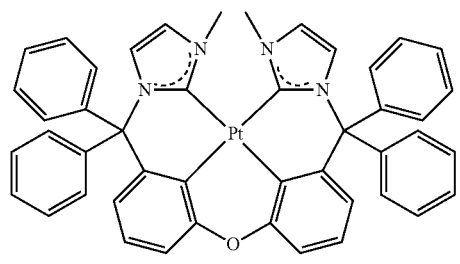
-continued
Compound 66
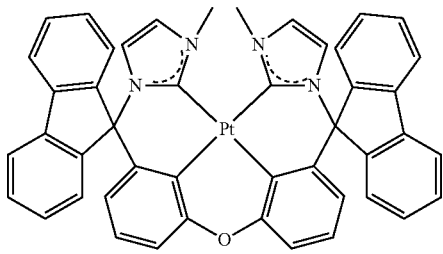
Compound 67
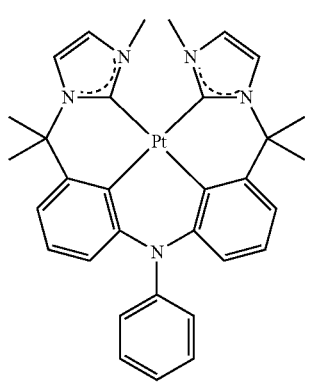
Compound 68
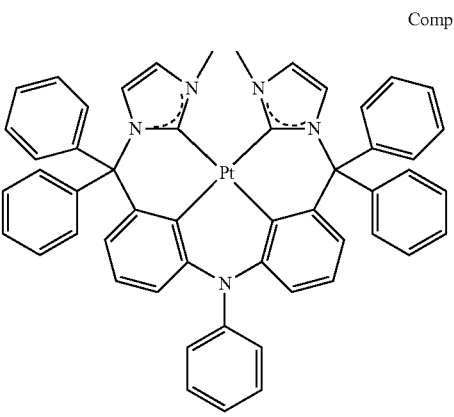
Compound 69
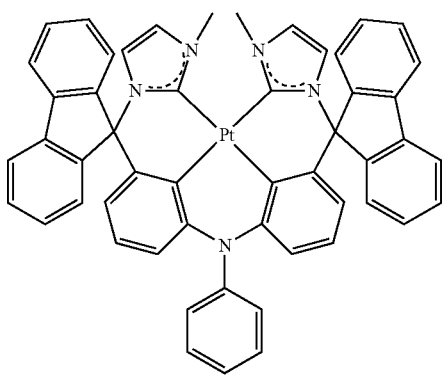

Compound 70
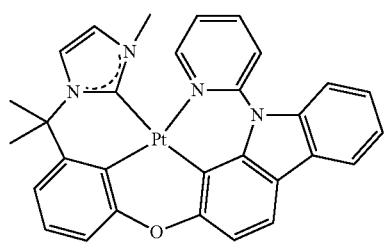
Compound 71
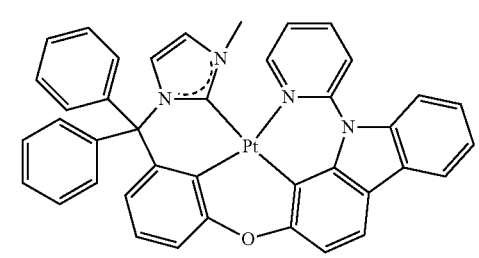
Compound 72
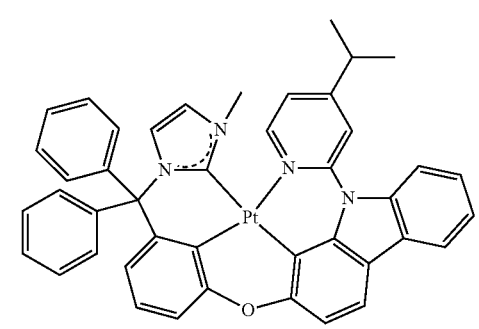
Compound 73
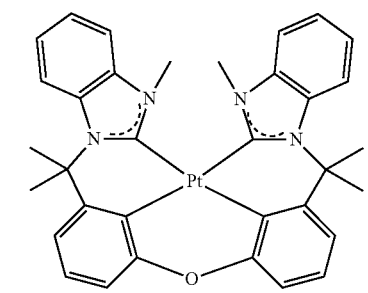
Compound 74
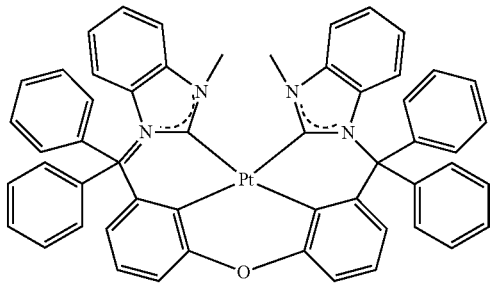
Compound 75
Compound 76
Compound 77
Compound 78
Compound 79
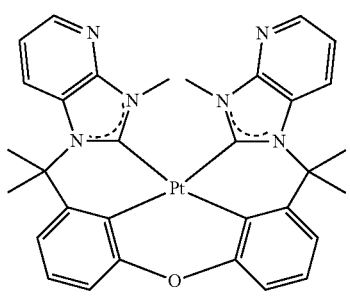

Compound 80
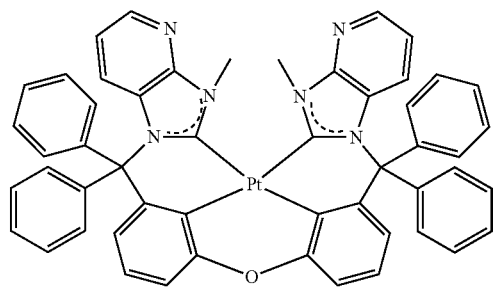
Compound 81
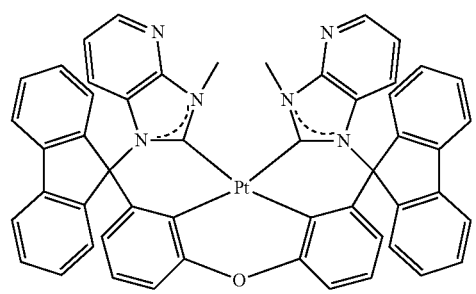
Compound 82
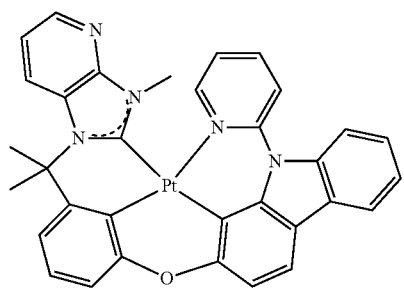
Compound 83
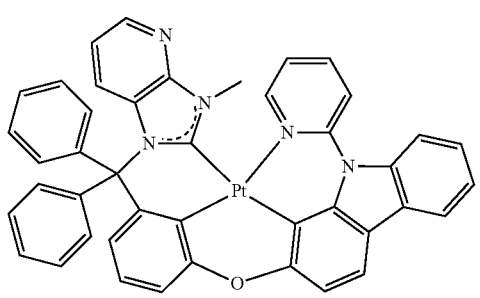
Compound 84
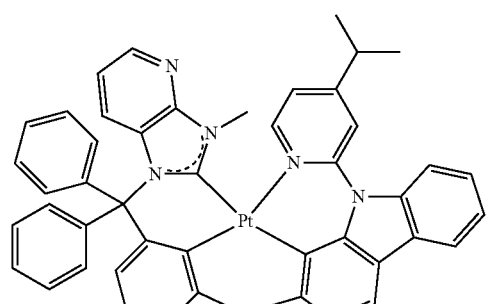
Compound 85
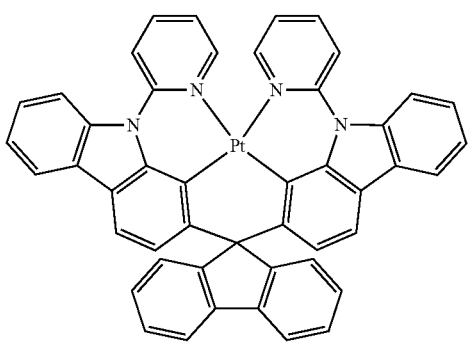
Compound 86
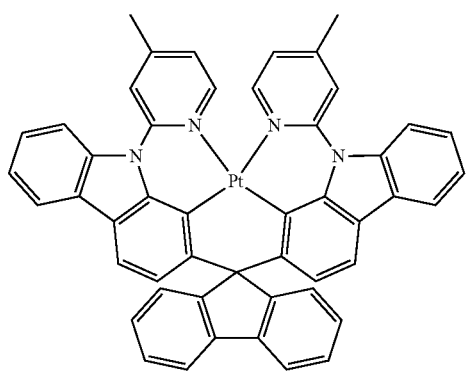
Compound 87
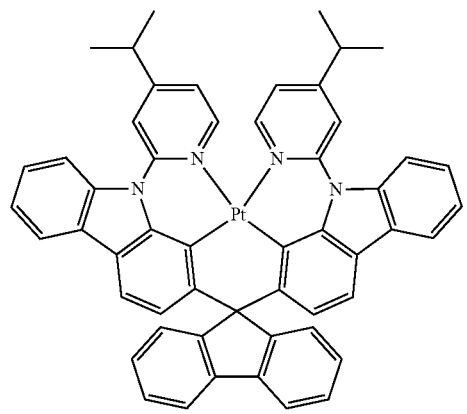
Compound 88
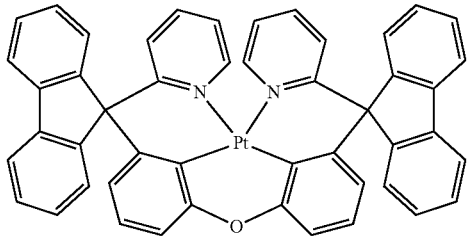

-continued
Compound 89
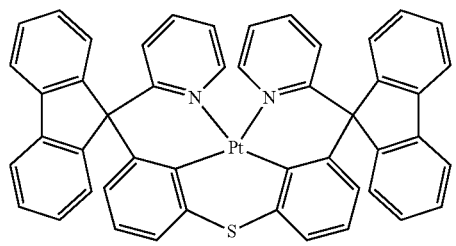
Compound 90
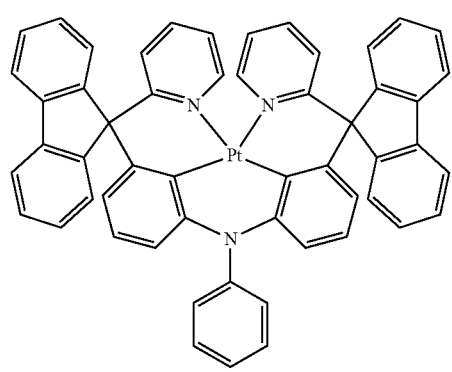
Compound 91
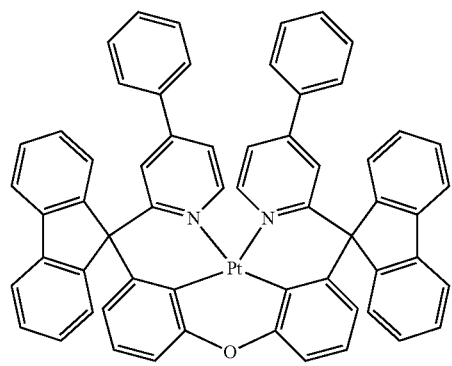
Compound 92
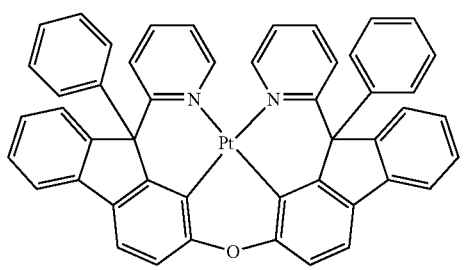
Compound 93
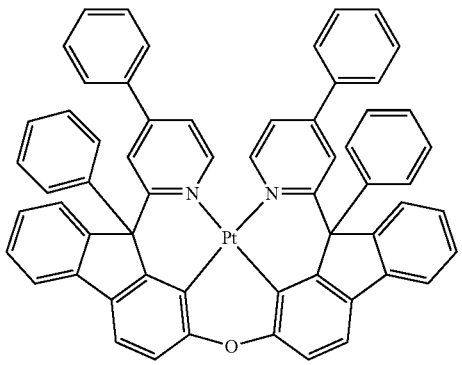
Compound 94
Compound 95
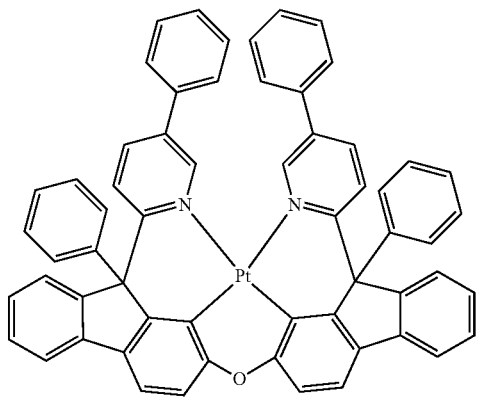
Compound 96
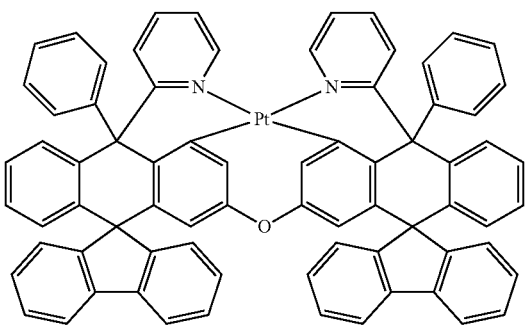

-continued
Compound 97
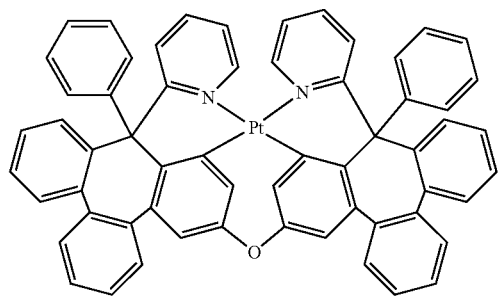
Compound 98
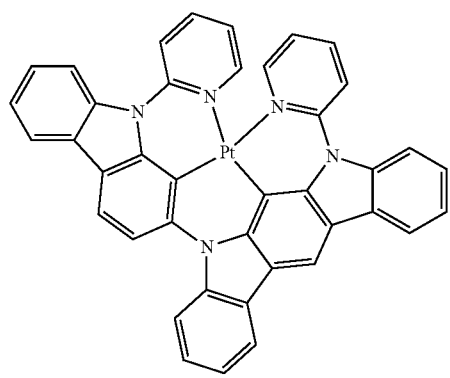
Compound 99
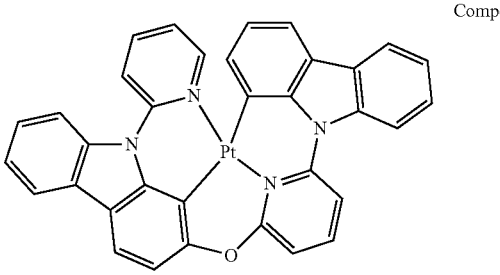
Compound 100
Compound 101
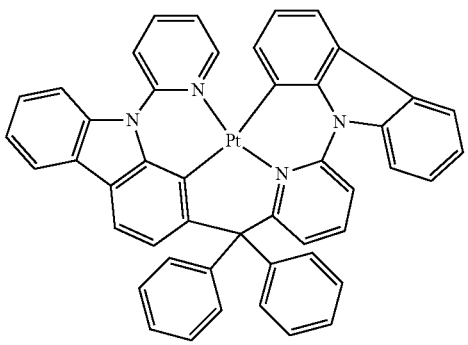
Compound 102
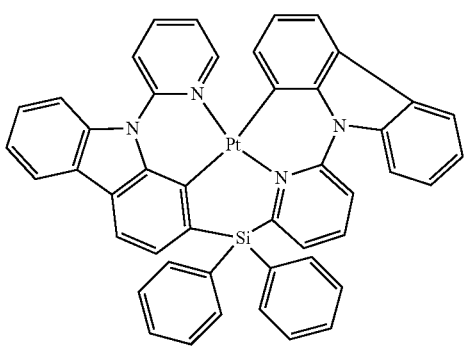
Compound 103
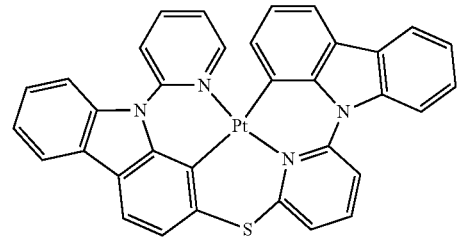
Compound 104
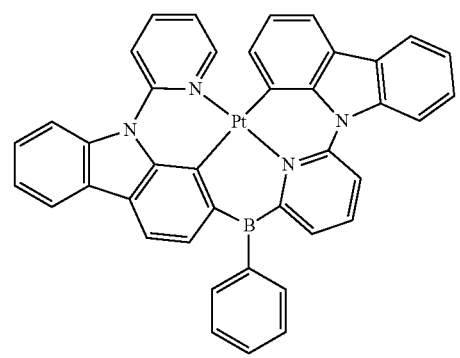

Compound 105
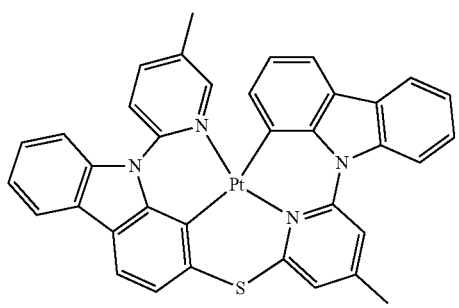
Compound 106
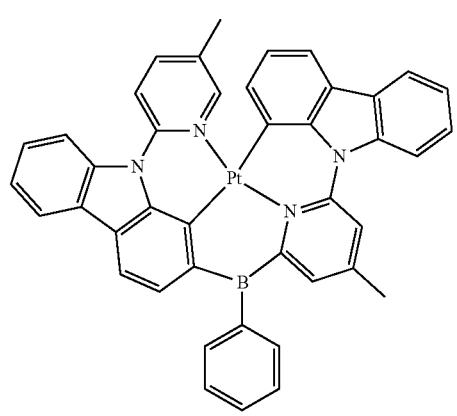
Compound 107
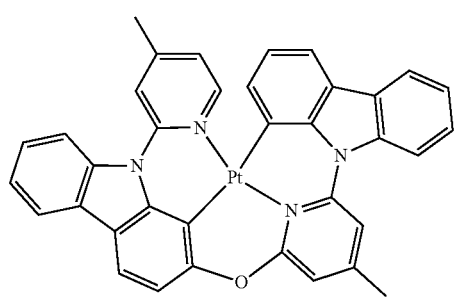
Compound 108
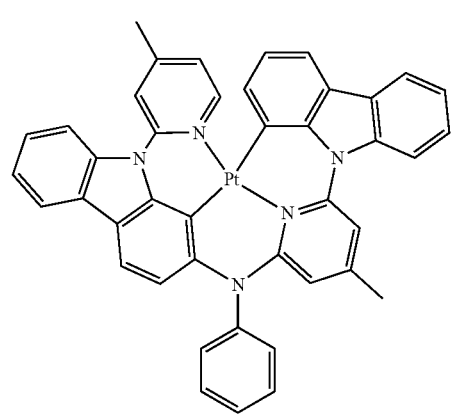
Compound 109
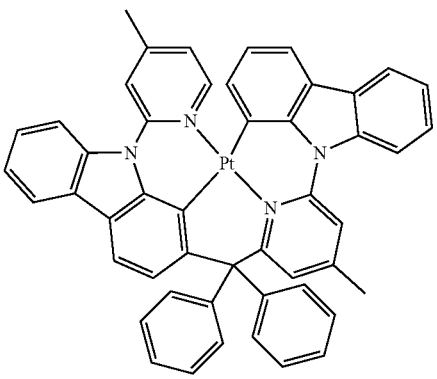
Compound 110
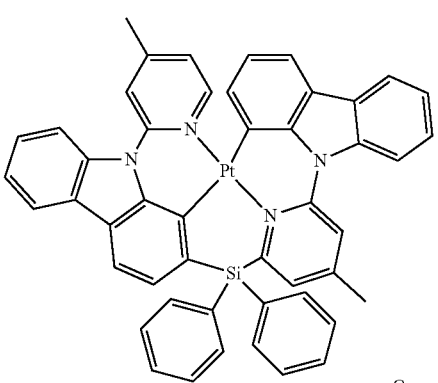
Compound 111
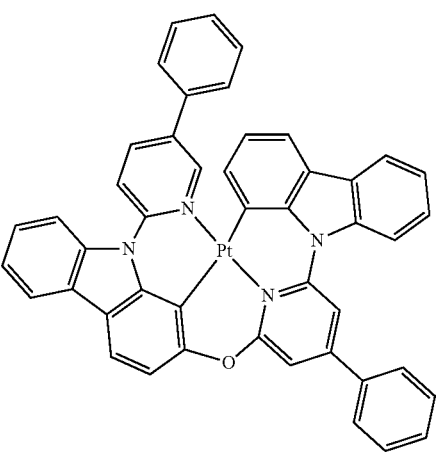
Compound 112
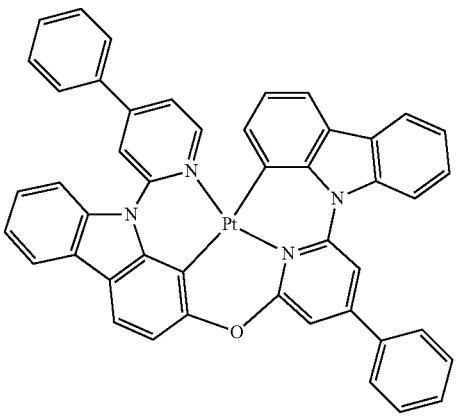

Compound 113
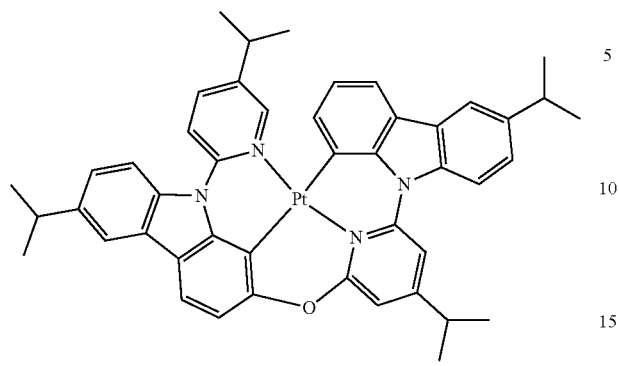
Compound 114
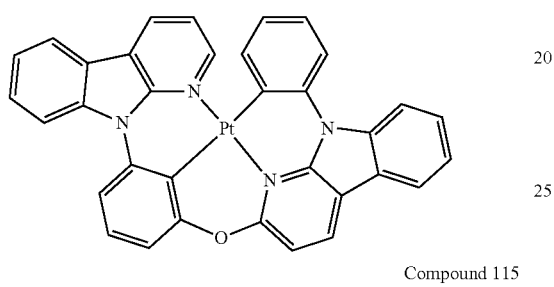
Compound 115
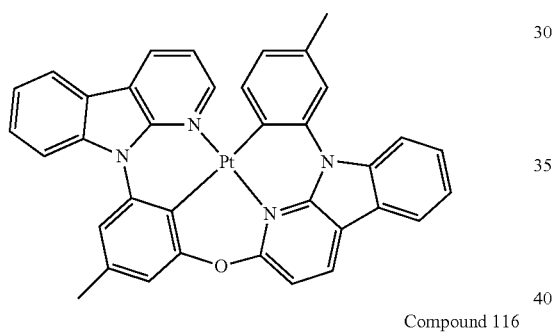
Compound 116
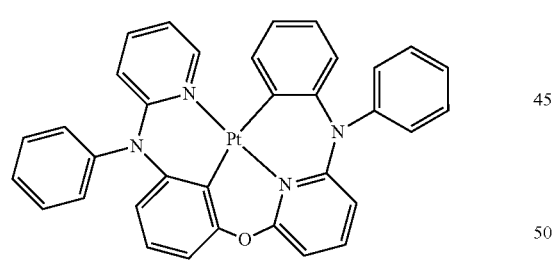
Compound 117
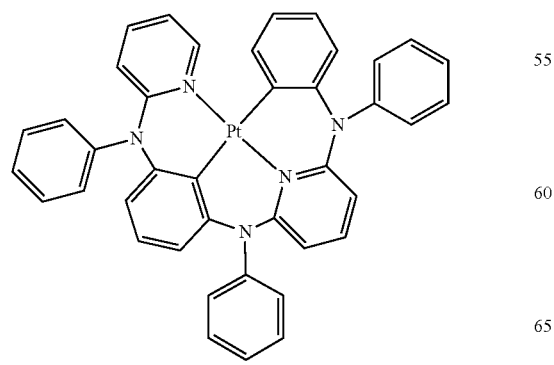
Compound 118
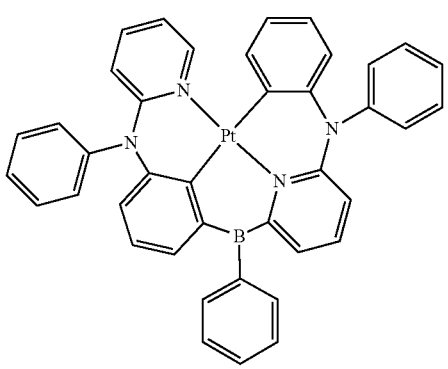
Compound 119
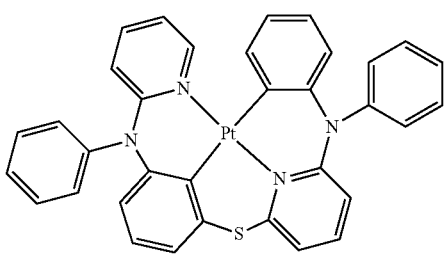
Compound 120
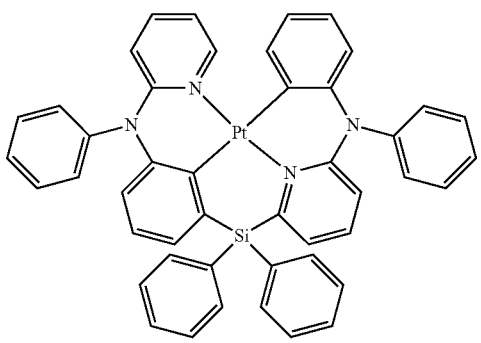
Compound 121
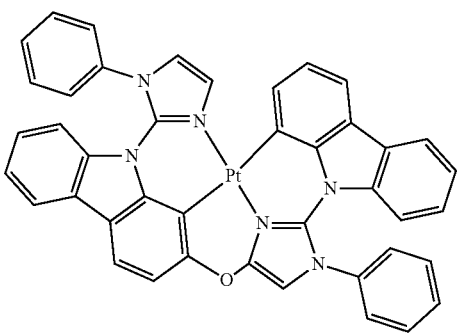

Compound 122
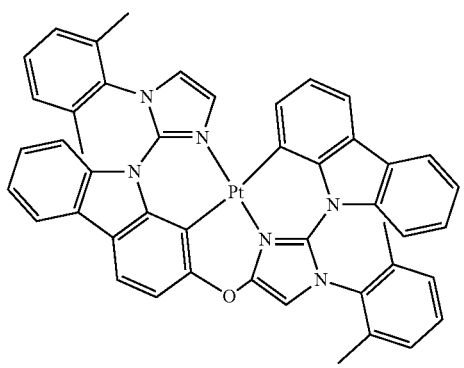
Compound 123
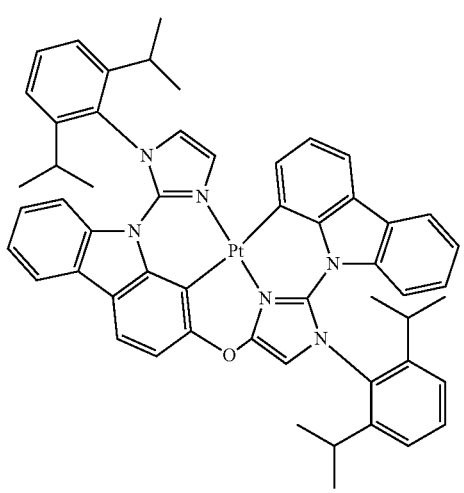
Compound 124
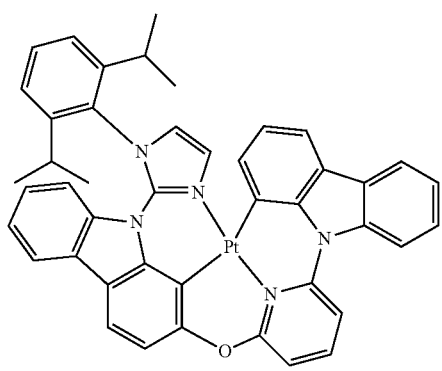
Compound 125
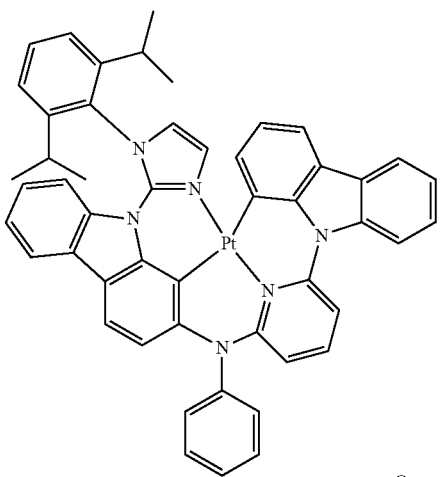
Compound 126
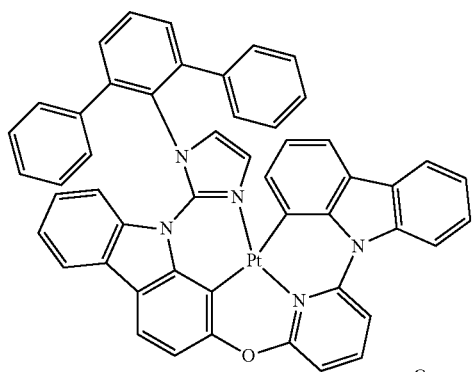
Compound 127
Compound 128
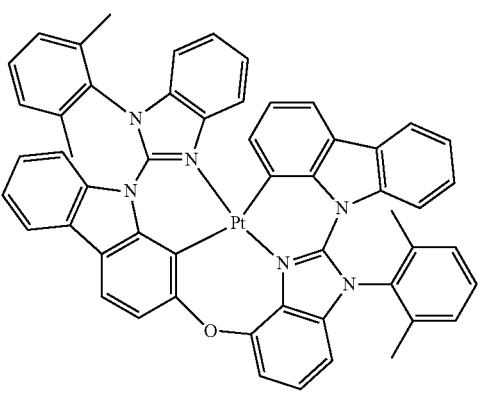

-continued

Compound 129

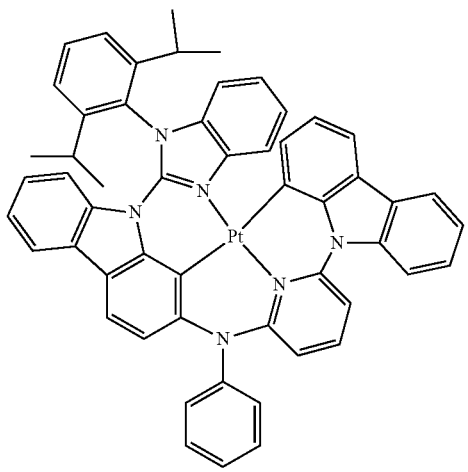

Compound 130

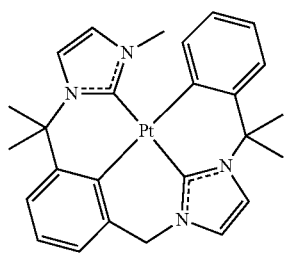

Compound 131

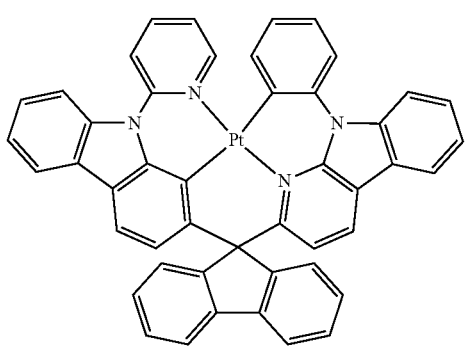

Compound 132

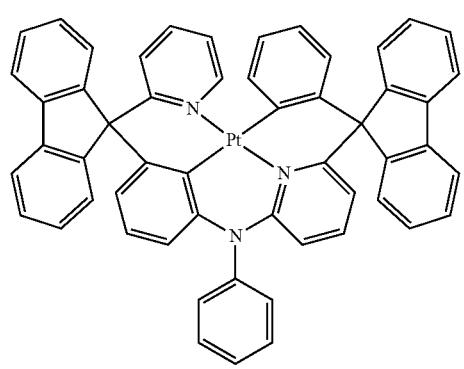

The dashed lines in compounds such as Compound 64 and Compound 75 mean that the fragment containing the dashed lines is a carbene, and the bond between the metal center (e.g. Pt) and the carbon atom is metal-carbene bond.

In one embodiment, a first device is provided. The first device comprises a first organic light emitting device, further comprising an anode, a cathode, and an organic layer, disposed between the anode and the cathode, comprising a compound having the formula:

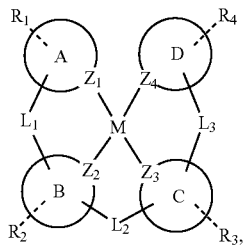

Formula I. In the compound of Formula I, rings A, B, C and D are each independently a 5- or 6-membered carbocyclic or heterocyclic ring, M is Pt or Pd, $L_1$ and $L_3$ are independently selected from the group consisting of BR, NR, PR, CRR', SiRR', and GeRR', $L_2$ is independently selected from the group consisting of BR, NR, PR, O, S, Se, C=O, S=O, $SO_2$, CRR', SiRR', and GeRR'. $Z_1$, $Z_2$, $Z_3$ and $Z_4$ are N carbon or nitrogen and at least one of $Z_2$ and $Z_3$ is carbon. $R_1$, $R_2$, $R_3$ and $R_4$, may represent mono-, di-, tri-, tetra-substitutions, or no substitution, and R, R', $R_1$, $R_2$, $R_3$, and $R_4$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof. Two or more adjacent R, R', $R_1$, $R_2$, $R_3$ and $R_4$ are optionally joined to form a fused ring.

In one embodiment, the first device is a consumer product. In one embodiment, the first device is an organic light-emitting device. In one embodiment, the first device comprises a lighting panel.

In one embodiment, the organic layer is an emissive layer and the compound is an emissive dopant. In one embodiment, the organic layer is an emissive layer and the compound is an non-emissive dopant.

In one embodiment, the organic layer further comprises a host. In one aspect, the host comprises a triphenylene containing benzo-fused thiophene or benzo-fused furan. Any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡CHC$_n$H$_{2n+1}$, $Ar_1$, $Ar_1$—$Ar_2$, $C_nH_{2n}$—$Ar_1$, or no substitution. $Ar_1$ and $Ar_2$ are independently selected from the group consisting of benzene, biphenyl, naphthalene, triphenylene, carbazole, and heteroaromatic analogs thereof, and n is from 1 to 10.

In one embodiment, the host comprises one or more compounds having the formula:

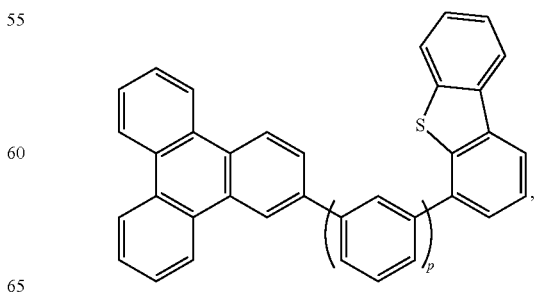

wherein p is 0 or 1.

In one embodiment, the host is selected from the group consisting of

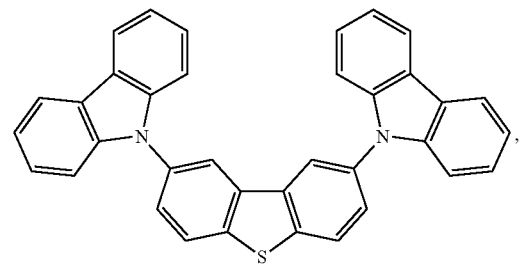

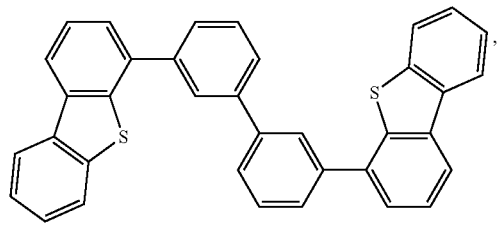

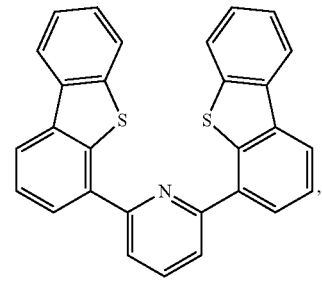

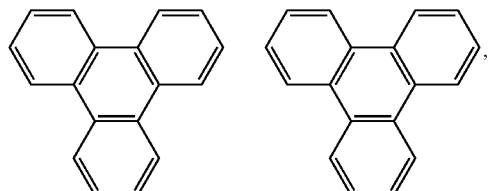

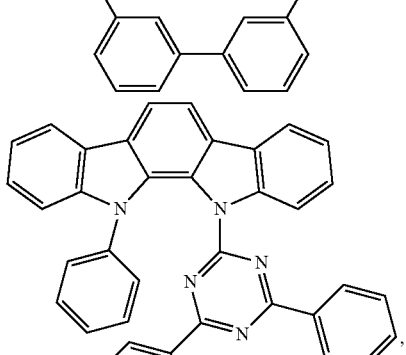

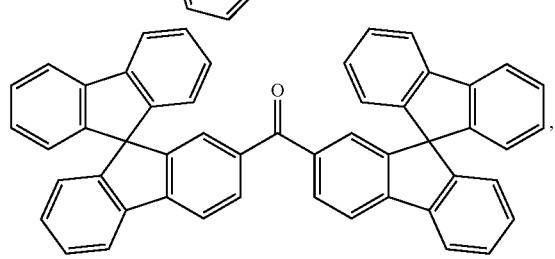

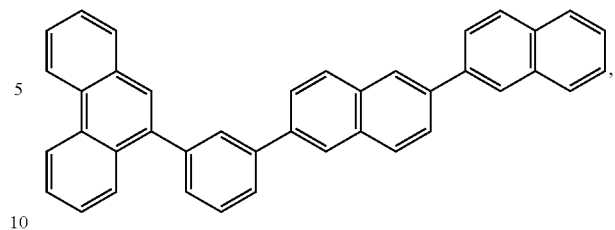

and combinations thereof.

In one embodiment, the host comprises a metal complex.

Device Examples

The exemplary devices described below may advantageously utilize the compounds of Formula I, and are not intended to be limiting. The structures of the materials used in the device examples are shown below:

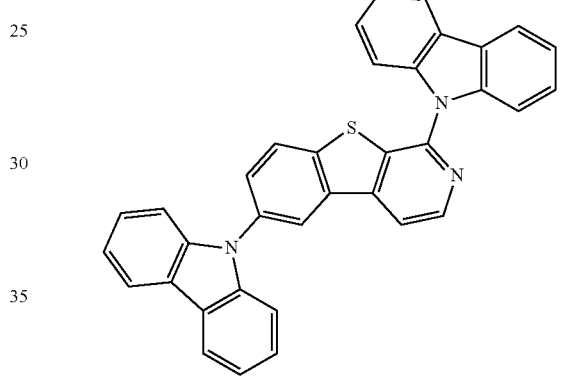

Host 1

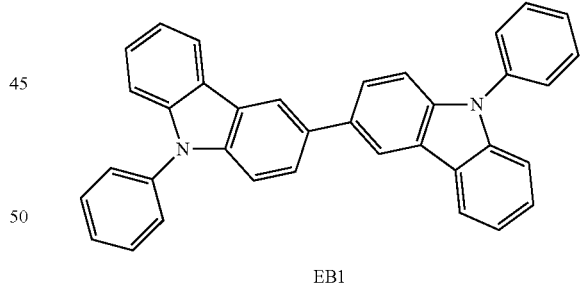

EB1

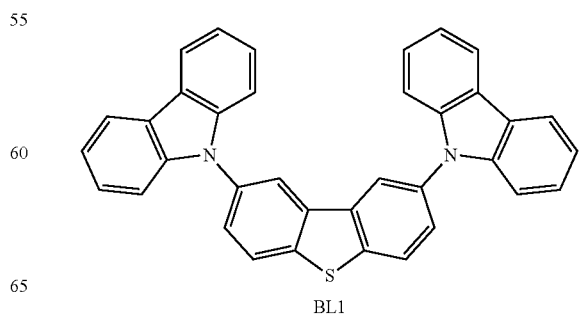

BL1

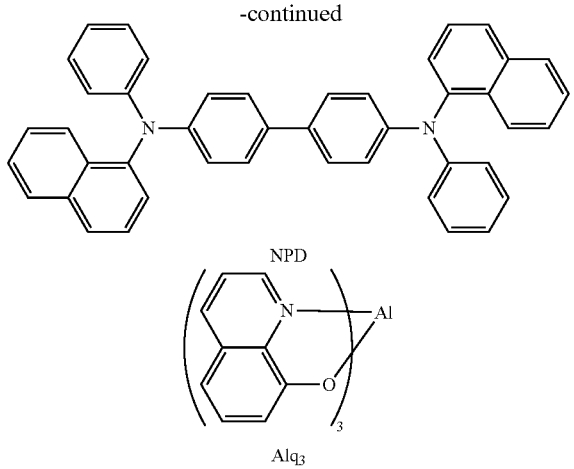

All device examples were fabricated by high vacuum (<10$^{-7}$ Torr) thermal evaporation (VTE). The anode electrode is 800 Å of indium tin oxide (ITO). The cathode consisted of 10 Å of LiF followed by 1000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package.

The organic stack of the devices consisted of sequentially, from the ITO surface, 100 Å of LG101 (purchased from LG Chemical) as the hole injection layer (HIL), 300 Å of NPD as the hole transporting layer (HTL), optionally 50 Å of EB1 as electron blocking layer (EBL), 300 Å of Host 1 doped with 20% of compound of Formula I as the emissive layer (EML), optionally 50 Å of BL1 as hole blocking layer (HBL), and 400 Å of Alq$_3$ as the electron transporting layer (ETL).

TABLE 2

Composition of Exemplary VTE Phosphorescent OLEDs

| Device Ex. | EBL | EML | HBL |
|---|---|---|---|
| 1 | None | Host 1:Compound 1 | None |
| 2 | None | Host 1:Compound 1 | HB1 |
| 3 | EB1 | Host 1:Compound 1 | None |
| 4 | EB1 | Host 1:Compound 1 | HB1 |

TABLE 3

VTE Device Data

| Device Ex. | 1931 CIE X | 1931 CIE Y | $\lambda_{max}$ (nm) | FWHM (nm) | Voltage (V) | At 1000 nits LE (Cd/A) | EQE (%) | PE (lm/W) | 20 mA/cm$^2$ L$_0$ (nits) |
|---|---|---|---|---|---|---|---|---|---|
| 1 | 0.262 | 0.487 | 502 | 88 | 4.7 | 15.5 | 5.8 | 10.4 | 3,112 |
| 2 | 0.267 | 0.502 | 508 | 88 | 6.0 | 11.1 | 4.0 | 5.8 | 2,347 |
| 3 | 0.258 | 0.493 | 504 | 86 | 4.5 | 21.2 | 7.7 | 14.6 | 4,586 |
| 4 | 0.266 | 0.507 | 508 | 88 | 5.9 | 13.9 | 4.9 | 7.4 | 3,157 |

In Table 3, the luminous efficiency (LE), external quantum efficiency (EQE) and power efficiency (PE) were measured at 1000 nits, while the initial luminance (L$_0$) was defined as the luminance upon applying a voltage with a constant current density of 20 mA/cm$^2$.

The devices emit from the dopant with Gaussian emission and $\lambda_{max}$ and FWHM (full width at half maximum) values of about 500 nm and 88 nm, respectively. Devices 1 and 3 have the best efficiency, both without a hole blocking layer. Device 3 was found to have the greatest efficiency, but slightly higher voltage compared to device 1. This result may be due to using EB1 as the electron blocking or exciton blocking layer.

TABLE 4

Computed Electronic Properties Using Density Functional Theory

| ID | Structure | HOMO (eV) | LUMO (eV) | Gap (eV) | T$_1$ (nm) |
|---|---|---|---|---|---|
| Compound 1 | 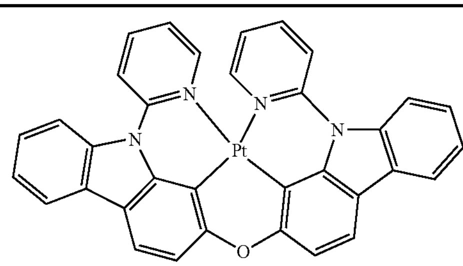 | −4.78 | −1.74 | −3.04 | 521 |

TABLE 4-continued

Computed Electronic Properties Using Density Functional Theory

| ID | Structure | HOMO (eV) | LUMO (eV) | Gap (eV) | $T_1$ (nm) |
|---|---|---|---|---|---|
| Comparative Example 1 | 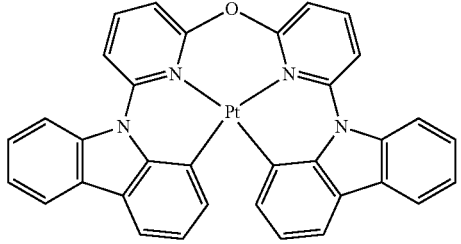 | −5.04 | −1.81 | −3.23 | 526 |
| Comparative Example 2 | 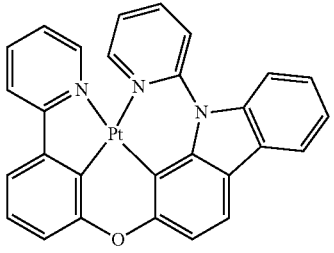 | −4.92 | −1.84 | −3.08 | 554 |
| Comparative Example 3 | 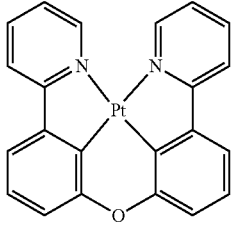 | −5.03 | −1.99 | −3.04 | 587 |

Geometry optimizations and single point energy calculations for the structures in Table 4 were performed using the Gaussian software package with the B3LYP/cep-31g functional and basis set.

Table 4 shows HOMO and LUMO energy levels, the HOMO-LUMO energy gap in electron volts (eV) and predicted triplet energies ($T_1$) in nanometers (nm) for Compound 1 and Comparative Examples 1-3 based on DFT calculations. The calculated triplet energy for Compound 1, in which the carbazole rings are linked by oxygen is higher in energy than Comparative Example 1 where the pyridine rings are linked by oxygen. In addition, the overall HOMO-LUMO energy gap for Compound 1 is smaller than that for Comparative Example 1. Without being bound by theory, this may allow for better stability when the compound is in a charged or excited state. The lower HOMO energy of Compound 1 compared to Comparative Example 1 may allow for it to be a better hole trap in a device resulting in higher device efficiencies. Therefore, both a higher triplet energy and smaller HOMO-LUMO bandgap energy are desirable properties found in compounds of Formula I such as Compound 1 but not in known compounds such as Comparative Example 1. Comparative Examples 2 and 3 further demonstrate how metal complexes with 6-membered metallocycle rings can provide higher triplet energies than those comprised of one 5-membered metallocycle rings (i.e. compounds in which $L_1$ and/or $L_3$ are single bonds, not bridging atoms that link two aromatic rings as in the compounds of Formula I). Comparative Example 2 is an example where $L_1$ is a single bond and has a lower triplet energy of 554 nm compared to Compound 1 and Comparative Example 3 is an example where $L_1$ and $L_3$ are single bonds and has a undesirably low triplet energy of 587 nm (cf. 521 nm for Compound 1). Thus, unexpectedly, compounds of Formula I, such as Compound 1, have both small HOMO-LUMO energy gaps and high triplet energies.

Photoluminescent quantum yield (PLQY) were measured as follows: Polymethylmethacrylate (PMMA) and Compound 1 were weighed out to give 5 weight % of compound 1. The mixture was dissolved in toluene. The solution was filtered through a 2 micron filter and drop cast onto a pre-cleaned quartz substrate. The PLQY measurement was carried out on a Hamamastu C9920 system equipped with a xenon lamp, integrating sphere and model C10027 photonic multi-channel analyzer. Photoluminescent excited state lifetime measurement was carried out by time correlated single photon counting method using a Horiba Jobin Yvon Fluorlog-3 integrated with an IBH data station hub using a 335 nm nanoLED as the excitation source. The data for Compound 1 and Comparative Examples 5 and 6 using these measurement conditions are shown in Table 5.

The PLQY and excited state lifetime measurements for Compound 1 result in values of 83% and 3.8 microseconds, respectively. These values are indicative of very high radiative rates, comparable to high efficiency phosphorescent molecules described in the literature, such as Ir(ppy)₃. Table 5 shows that Compound 1 has a similar PLQY and excited state lifetime to Comparative Examples 5 and 6 under the same measurement conditions. In comparison, compounds with 6-membered metallocycle ring systems, where the conjugation is broken by linking groups between the A and B rings, or the C and D rings, typically do not possess the high PLQY and short excited state lifetimes provided by compounds of Formula I. The Comparative Example 4 is found to be non-emissive at room temperature, demonstrating this property. These desirable values indicate that compounds of Formula I can be useful in OLEDs.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the

TABLE 5

Comparative PLQY and Excited State Lifetime Data

| Compound ID | Structure | PLQY (%) | Excited-State Lifetime (μs) |
|---|---|---|---|
| Compound 1 | 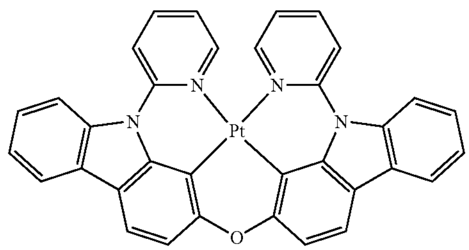 | 83 | 3.8 |
| Comparative Example 4 | 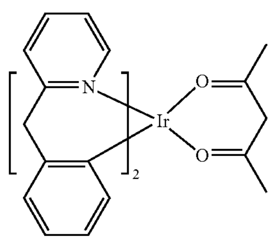 | No emission | — |
| Comparative Example 5 | 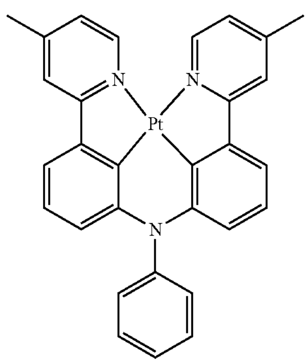 | 70 | 6.6 |
| Comparative Example 6 | | 93 | 1.5 | art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

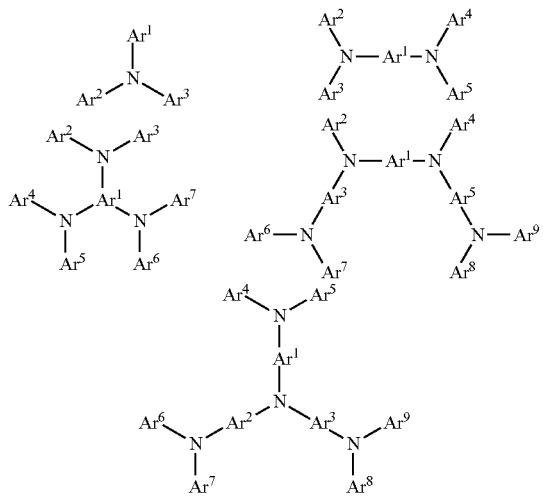

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group.

Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

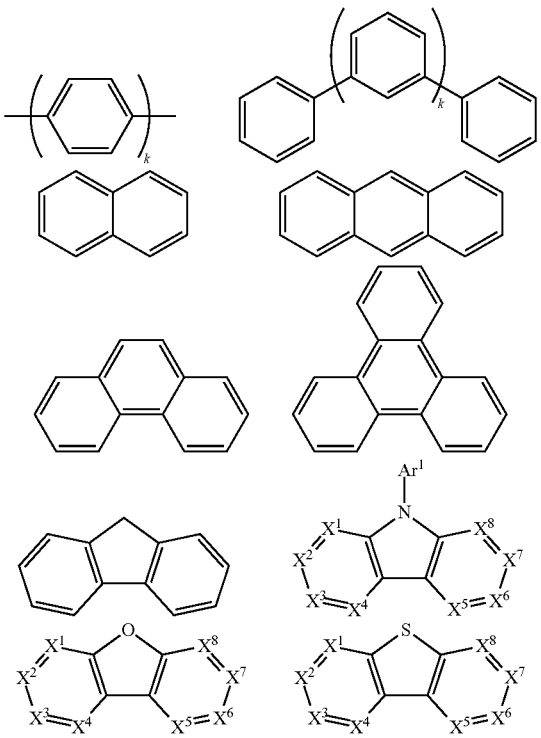

k is an integer from 1 to 20; $X^1$ to $X^8$ is C (including CH) or N; $Ar^1$ has the same group defined above.

Examples of metal complexes used in HIL or HTL include, but not limit to the following general formula:

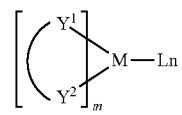

M is a metal, having an atomic weight greater than 40; ($Y^1$—$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$—$Y^2$) is a 2-phenylpyridine derivative.

In another aspect, ($Y^1$—$Y^2$) is a carbene ligand.

In another aspect, M is selected from Ir, Pt, Os, and Zn.

In a further aspect, the metal complex has a smallest oxidation potential in solution vs. Fc$^+$/Fc couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

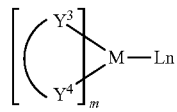

M is a metal; $(Y^3-Y^4)$ is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

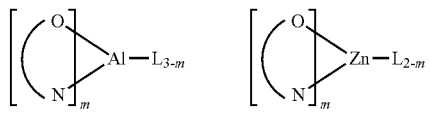

(O—N) is a bidentate ligand, having metal coordinated to atoms O and N.

In another aspect, M is selected from Ir and Pt.

In a further aspect, $(Y^3-Y^4)$ is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

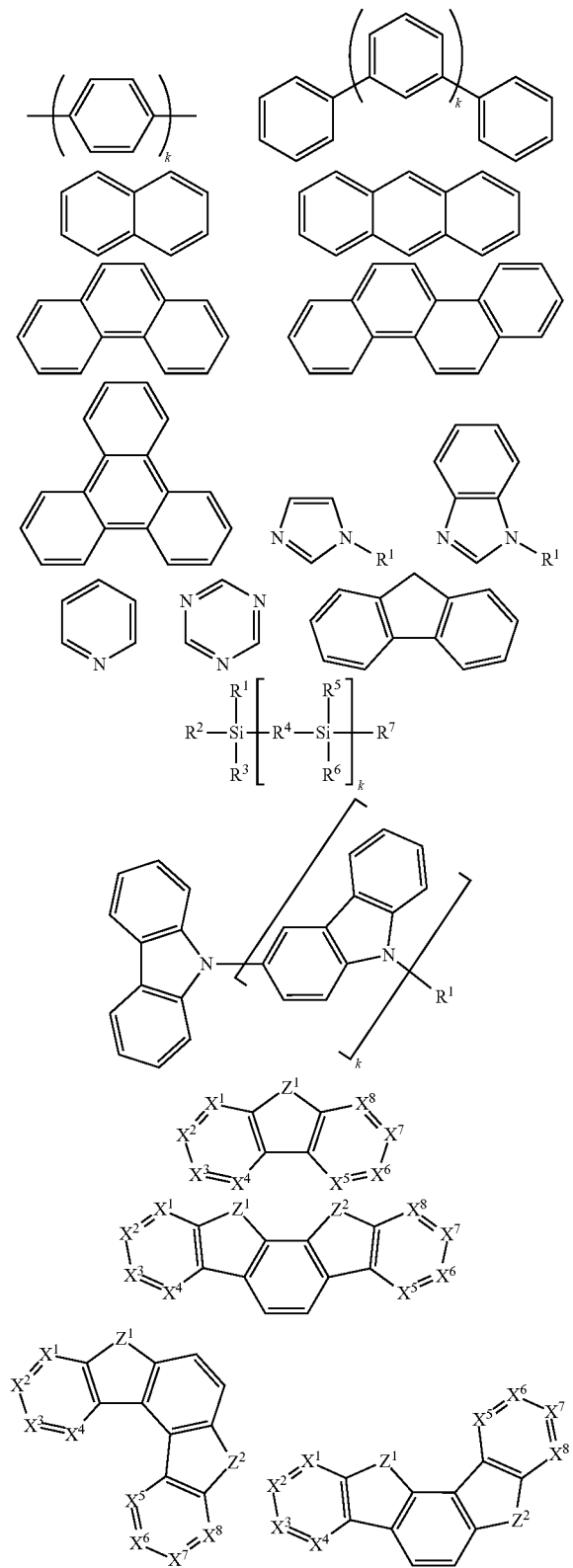

-continued

R¹ to R⁷ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

X¹ to X⁸ is selected from C (including CH) or N.

Z¹ and Z² is selected from NR¹, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

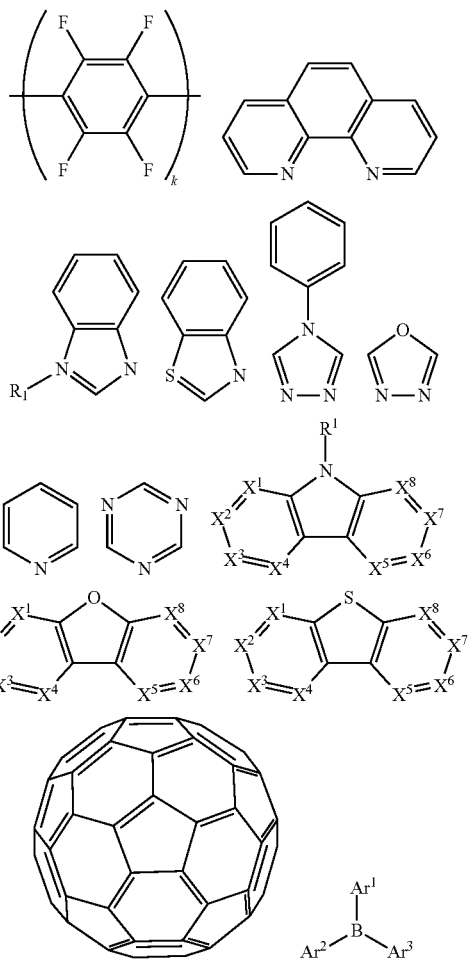

R¹ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

Ar¹ to Ar³ has the similar definition as Ar's mentioned above.

k is an integer from 0 to 20.

X¹ to X⁸ is selected from C (including CH) or N.

In another aspect, the metal complexes used in ETL contains, but not limit to the following general formula:

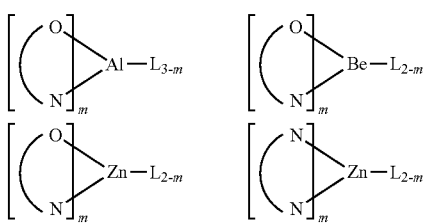

(O—N) or (N—N) is a bidentate ligand, having metal coordinated to atoms O, N or N,N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 6 below. Table 6 lists non-limiting classes of materials, non-limiting examples of compounds for each class, and references that disclose the materials.

TABLE 6
| MATERIAL | EXAMPLES OF MATERIAL | PUBLICATIONS |
| --- | --- | --- |
| Hole injection materials | | |
| Phthalocyanine and porphryin compounds | 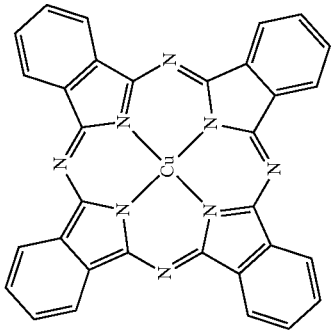 | Appl. Phys. Lett. 69, 2160 (1996) |
| Starburst triarylamines | 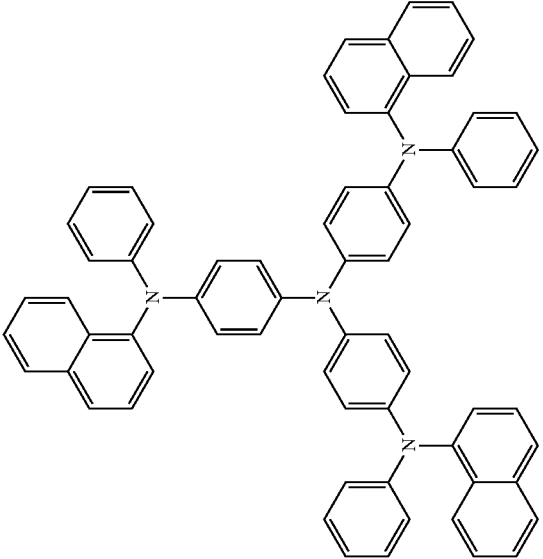 | J. Lumin. 72-74, 985 (1997) |
| $CF_x$ Fluorohydrocarbon polymer |  | Appl. Phys. Lett. 78, 673 (2001) |

TABLE 6-continued
| MATERIAL | EXAMPLES OF MATERIAL | PUBLICATIONS |
|---|---|---|
| Conducting polymers (e.g., PEDOT:PSS, polyaniline, polypthiophene) | 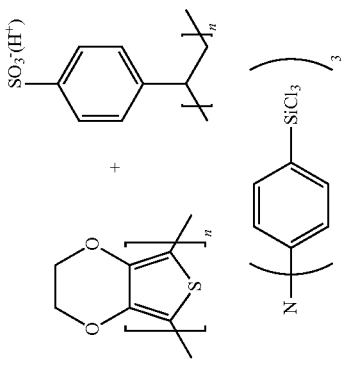 | Synth. Met. 87, 171 (1997) WO2007002683 |
| Phosphonic acid and silane SAMs | | US2003016053 |
| Triarylamine or polythiophene polymers with conductivity dopants | | EP1725079A1 |

TABLE 6-continued
| MATERIAL | EXAMPLES OF MATERIAL | PUBLICATIONS |
|---|---|---|
| Organic compounds with conductive inorganic compounds, such as molybdenum and tungsten oxides | 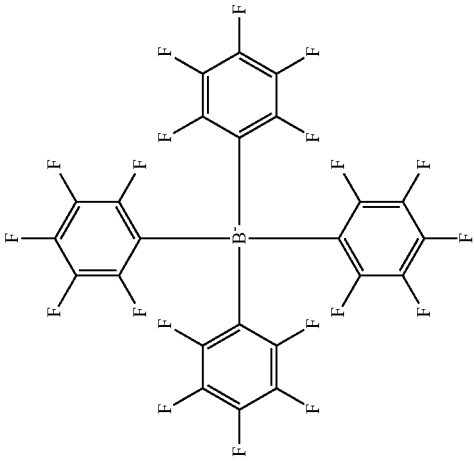 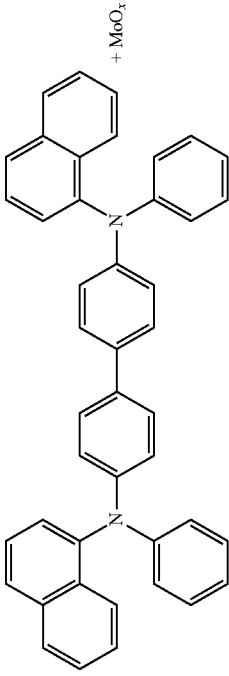 | US2005013751 SID Symposium Digest, 37, 923 (2006) WO2009018009 |
| n-type semiconducting organic complexes | 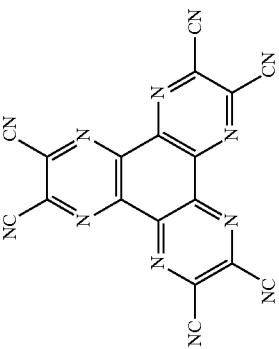 | US20020158242 |

TABLE 6-continued
| MATERIAL | EXAMPLES OF MATERIAL | PUBLICATIONS |
| --- | --- | --- |
| Metal organometallic complexes | | US20060240279 |
| Cross-linkable compounds | 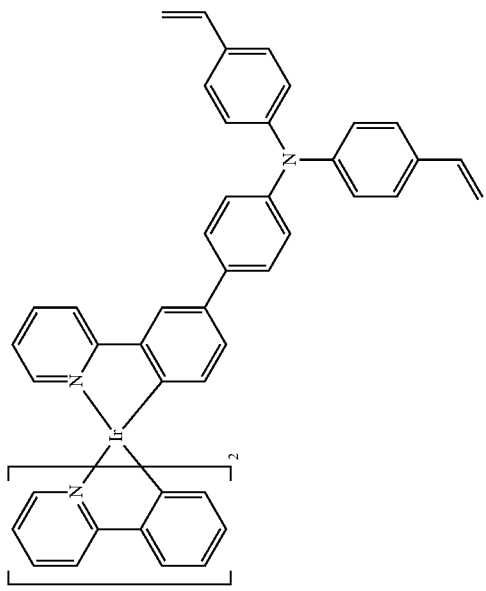 | US20080220265 |

TABLE 6-continued
| MATERIAL | EXAMPLES OF MATERIAL | PUBLICATIONS |
|---|---|---|
| Polythiophene based polymers and copolymers | 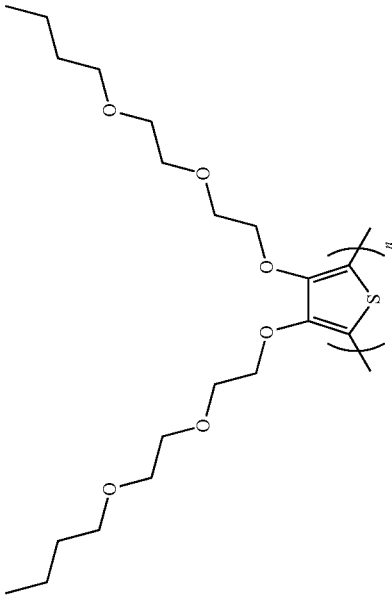 | WO 2011075644<br>EP2350216 |
| Hole transporting materials | | |
| Triarylamines (e.g., TPD, α-NPD) | 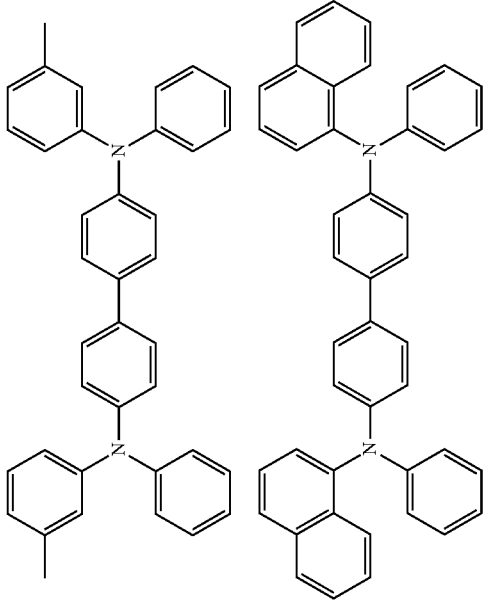 | Appl. Phys. Lett. 51, 913 (1987)<br><br>U.S. Pat. No. 5,061,569 |

TABLE 6-continued
| MATERIAL | EXAMPLES OF MATERIAL | PUBLICATIONS |
|---|---|---|
| | 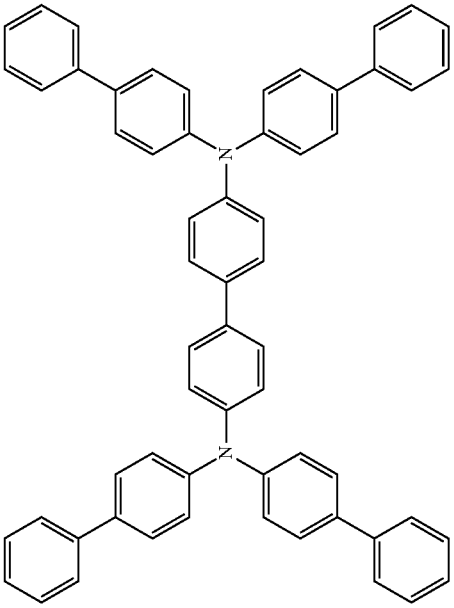 | EP650955 |
| | 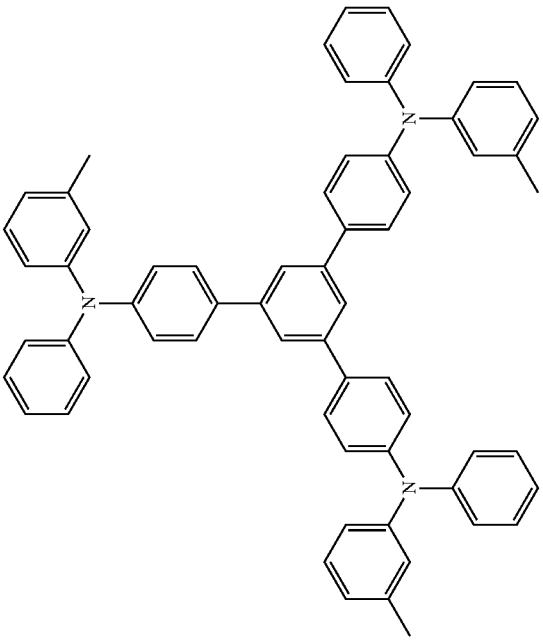 | J. Mater. Chem. 3, 319 (1993) |

| MATERIAL | EXAMPLES OF MATERIAL | PUBLICATIONS |
|---|---|---|
| | 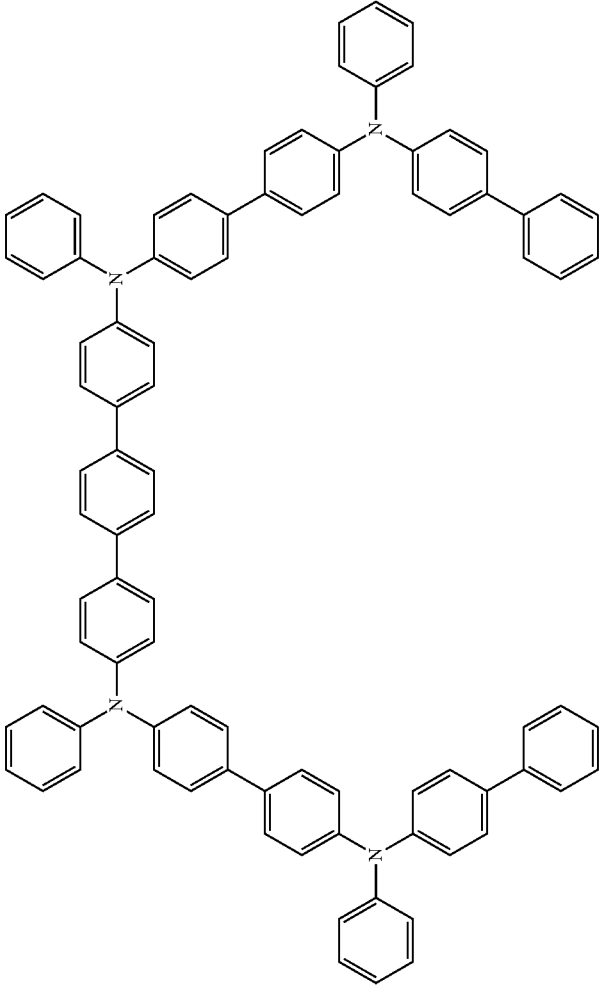 | Appl. Phys. Lett. 90, 183503 (2007) |

TABLE 6-continued
| MATERIAL | EXAMPLES OF MATERIAL | PUBLICATIONS |
|---|---|---|
|  | 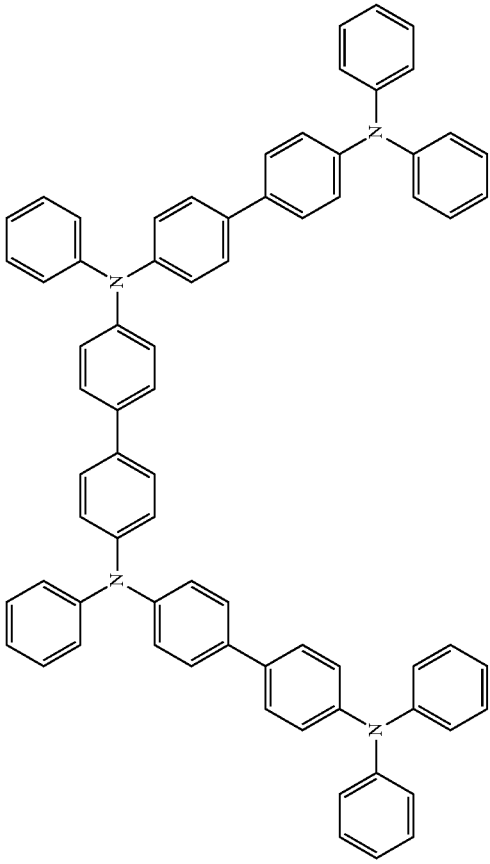 | Appl. Phys. Lett. 90, 183503 (2007) |
| Triaylamine on spirofluorene core | 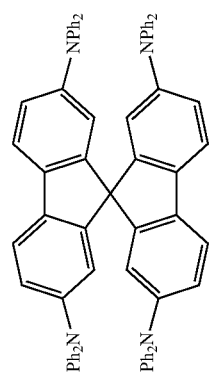 | Synth. Met. 91, 209 (1997) |

TABLE 6-continued
| MATERIAL | EXAMPLES OF MATERIAL | PUBLICATIONS |
|---|---|---|
| Arylamine carbazole compounds | 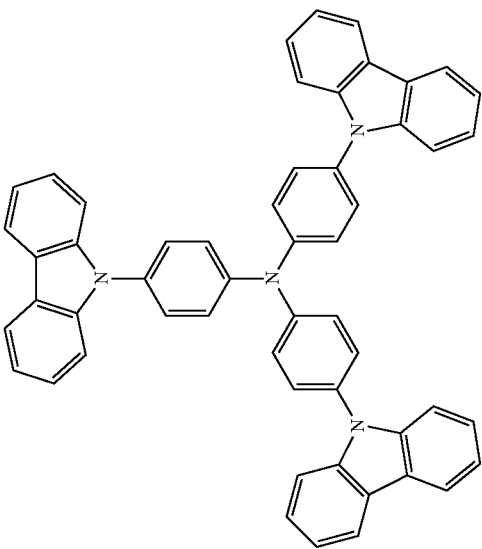 | Adv. Mater. 6, 677 (1994), US20080124572 |
| Triarylamine with (di)benzothiophene/(di)benzofuran | | US20070278938, US20080106190 US20110163302 |

TABLE 6-continued
| MATERIAL | EXAMPLES OF MATERIAL | PUBLICATIONS |
|---|---|---|
| Indolocarbazoles | 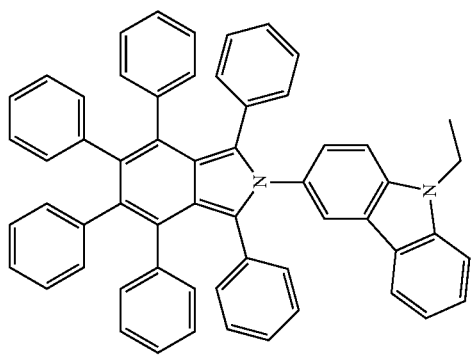 | Synth. Met. 111, 421 (2000) |
| Isoindole compounds | 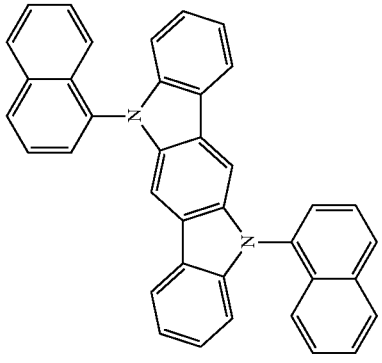 | Chem. Mater. 15, 3148 (2003) |

TABLE 6-continued

| MATERIAL | EXAMPLES OF MATERIAL | PUBLICATIONS |
|---|---|---|
| Metal carbene complexes | | US20080018221 |
| Phosphorescent OLED host materials Red hosts | | |
| Arylcarbazoles | | Appl. Phys. Lett. 78, 1622 (2001) |
| Metal 8-hydroxyquinolates (e.g, Alq$_3$, BAlq) | | Nature 395, 151 (1998) |
| | | US20060202194 |

TABLE 6-continued
| MATERIAL | EXAMPLES OF MATERIAL | PUBLICATIONS |
|---|---|---|
| | 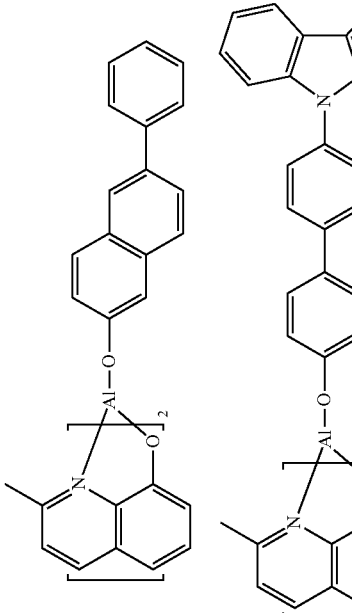 | WO2005014551 |
| | 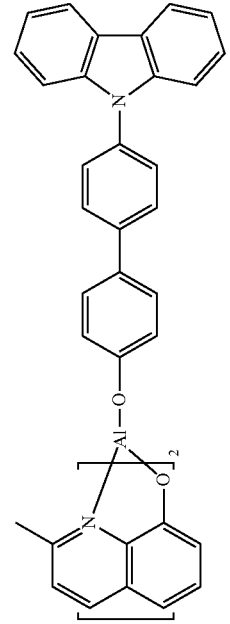 | WO2006072002 |
| Metal phenoxybenzothiazole compounds | 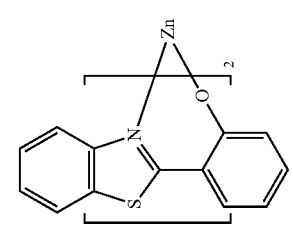 | Appl. Phys. Lett. 90, 123509 (2007) |
| Conjugated oligomers and polymers (e.g., polyfluorene) | 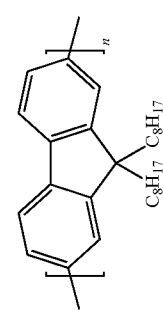 | Org. Electron. 1, 15 (2000) |

TABLE 6-continued
| MATERIAL | EXAMPLES OF MATERIAL | PUBLICATIONS |
|---|---|---|
| Aromatic fused rings | 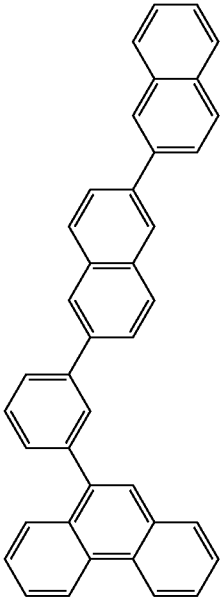 | WO2009066779, WO2009066778, WO2009063833, US20090045731, US20090045730, US20090908311, US20090008605, US20090009065 |
| Zinc complexes | 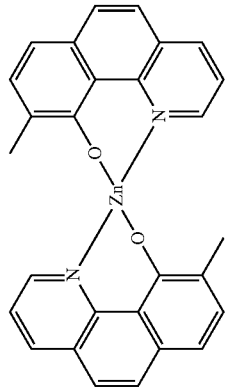 | WO2011056066 |
| Chrysene based compounds | 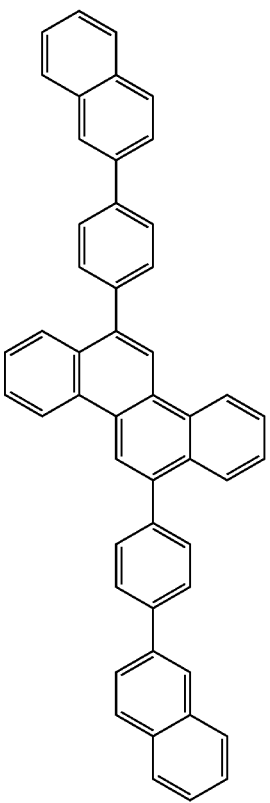 | WO2011086863 |
| Green hosts | | |
| Arylcarbazoles | 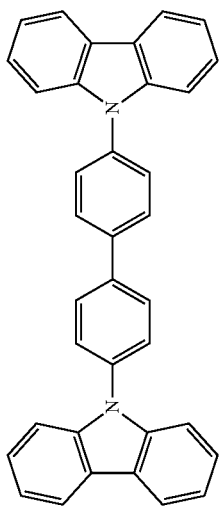 | Appl. Phys. Lett. 78, 1622 (2001) |

TABLE 6-continued
| MATERIAL | EXAMPLES OF MATERIAL | PUBLICATIONS |
|---|---|---|
| | 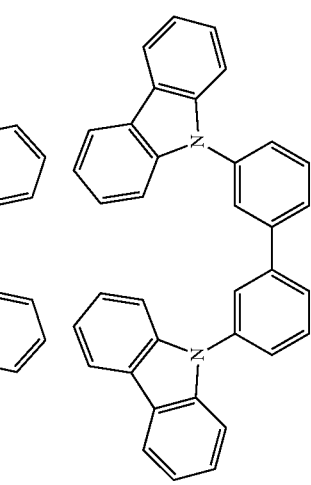 | US20030175553 WO2001039234 |
| Aryltriphenylene compounds | 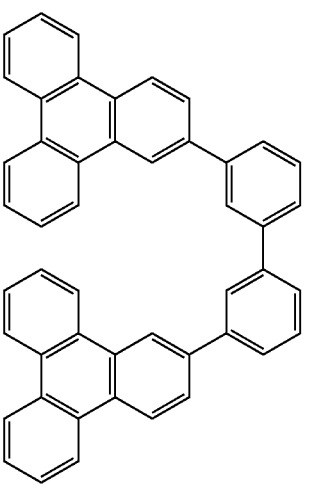 | US20060280965 |

| MATERIAL | EXAMPLES OF MATERIAL | PUBLICATIONS |
|---|---|---|
| | | US20060280965 |
| | | WO2009021126 |
| Poly-fused heteroaryl compounds | | US20090309488 US20090302743 US20100012931 |

TABLE 6-continued
| MATERIAL | EXAMPLES OF MATERIAL | PUBLICATIONS |
|---|---|---|
| Donor acceptor type molecules | 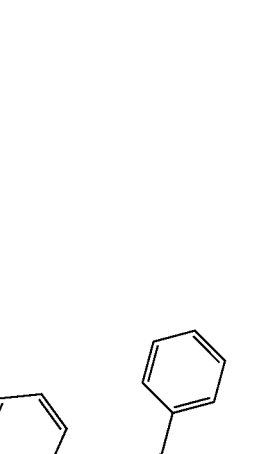 | WO2008056746 |
| |  | WO2010107244 |

TABLE 6-continued

| MATERIAL | EXAMPLES OF MATERIAL | PUBLICATIONS |
|---|---|---|
| Aza-carbazole/DBT/DBF | | JP2008074939 |
| | | US20100187984 |
| Polymers (e.g., PVK) | | Appl. Phys. Lett. 77, 2280 (2000) |

TABLE 6-continued
| MATERIAL | EXAMPLES OF MATERIAL | PUBLICATIONS |
|---|---|---|
| Spirofluorene compounds | 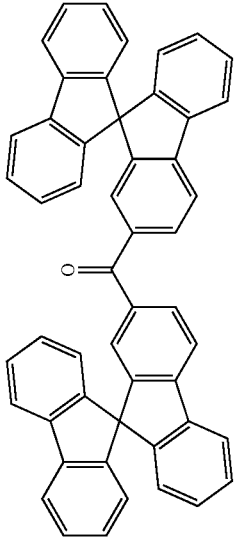 | WO2004093207 |
| Metal phenoxybenzooxazole compounds | | WO2005089025 |
| | | WO2006132173 |
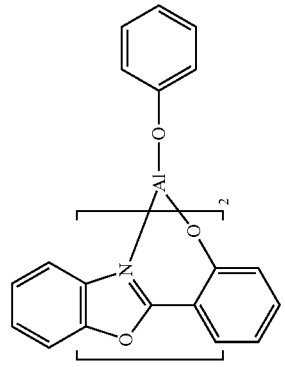

TABLE 6-continued
| MATERIAL | EXAMPLES OF MATERIAL | PUBLICATIONS |
|---|---|---|
| | 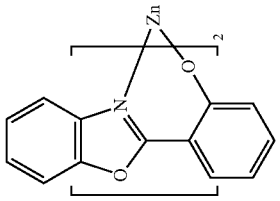 | JP2005111610 |
| Spirofluorene-carbazole compounds | 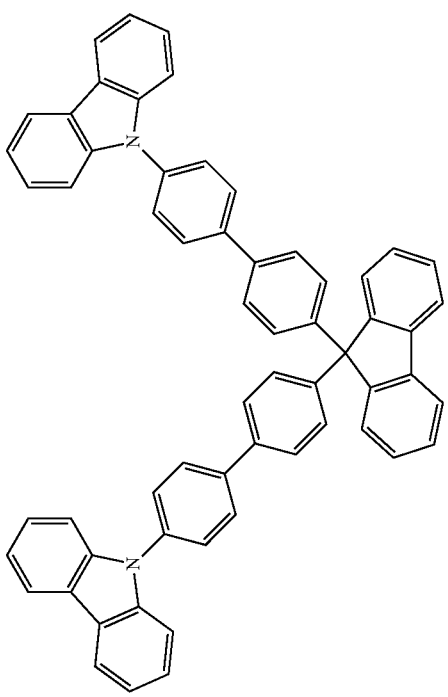 | JP2007254297 JP2007254297 |

TABLE 6-continued
| MATERIAL | EXAMPLES OF MATERIAL | PUBLICATIONS |
|---|---|---|
| Indolocarbazoles | 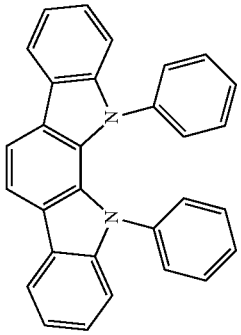 | WO2007063796 |
| | 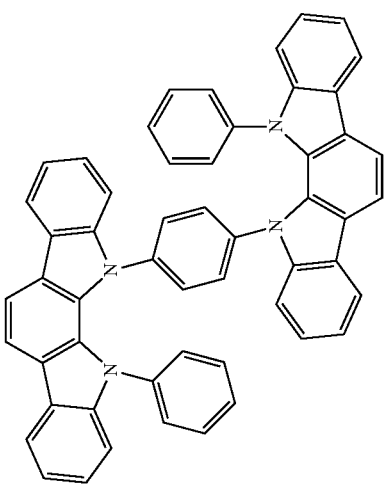 | WO2007063754 |
| 5-member ring electron deficient heterocycles (e.g, triazole, oxadiazole) | 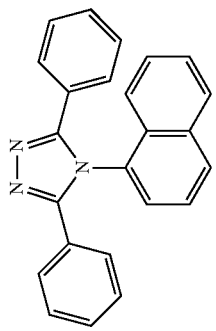 | J. Appl. Phys. 90, 5048 (2001) |

TABLE 6-continued

| MATERIAL | EXAMPLES OF MATERIAL | PUBLICATIONS |
|---|---|---|
| | | WO2004107822 |
| | | US2005011240 |
| Tetraphenylene complexes | | US2005012407 |
| Metal phenoxypyridine compounds | | WO2005030900 |

TABLE 6-continued

| MATERIAL | EXAMPLES OF MATERIAL | PUBLICATIONS |
|---|---|---|
| Metal coordination complexes (e.g., Zn, Al with N^N ligands) | | US20040137268, US20040137267 |
| Blue hosts | | |
| Arylcarbazoles | | Appl. Phys. Lett. 82, 2422 (2003) |
| | | US20070190359 |
| Dibenzothiophene/Dibenzofuran-carbazole compounds | | WO2006114966, US20090167162 |

TABLE 6-continued
| MATERIAL | EXAMPLES OF MATERIAL | PUBLICATIONS |
|---|---|---|
| | 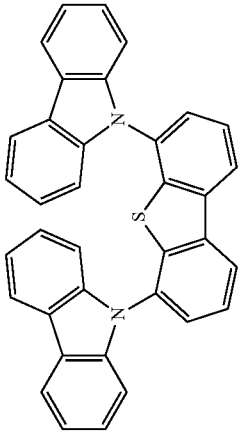 | US20090167162 |
| | 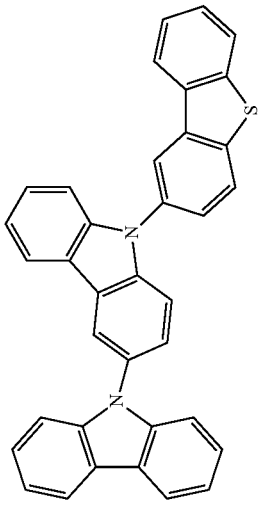 | WO2009086028 |
| | 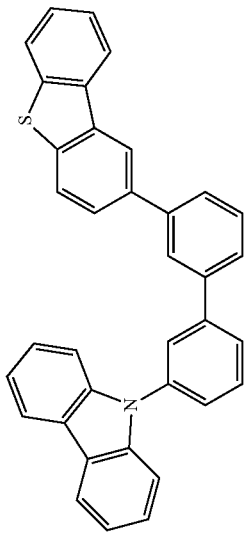 | US20090030202, US20090017330 |

TABLE 6-continued

| MATERIAL | EXAMPLES OF MATERIAL | PUBLICATIONS |
|---|---|---|
| | | US20100084966 |
| Silicon aryl compounds | | US20050238919 |
| | | WO2009003898 |

TABLE 6-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |

TABLE 6-continued

| MATERIAL | EXAMPLES OF MATERIAL | PUBLICATIONS |
|---|---|---|
| High triplet metal organometallic complex | | U.S. Pat. No. 7,154,114 |
| Phosphorescent dopants Red dopants | | |
| Heavy metal porphyrins (e.g., PtOEP) | | Nature 395, 151 (1998) |
| Iridium(III) organometallic complexes | | Appl. Phys. Lett. 78, 1622 (2001) |

TABLE 6-continued

| MATERIAL | EXAMPLES OF MATERIAL | PUBLICATIONS |
|---|---|---|
| | | US2006835469 |
| | | US2006835469 |
| | | US2006202194 |

TABLE 6-continued

| MATERIAL | EXAMPLES OF MATERIAL | PUBLICATIONS |
|---|---|---|
| | | US20060202194 |
| | | US20070087321 |
| | | US20080261076 US20100090591 |

TABLE 6-continued

| MATERIAL | EXAMPLES OF MATERIAL | PUBLICATIONS |
| --- | --- | --- |
| | | US2007087321 |
| | | Adv. Mater. 19, 739 (2007) |
| | | WO2009100991 |

| MATERIAL | EXAMPLES OF MATERIAL | PUBLICATIONS |
|---|---|---|
| | | WO2008101842 |
| | | U.S. Pat. No. 7,232,618 |
| Platinum(II) organometallic complexes | | WO2003040257 |

TABLE 6-continued

| MATERIAL | EXAMPLES OF MATERIAL | PUBLICATIONS |
|---|---|---|
| | | US20070103060 |
| Osminum(III) complexes | | Chem. Mater. 17, 3532 (2005) |
| Ruthenium(II) complexes | | Adv. Mater. 17, 1059 (2005) |

TABLE 6-continued
| MATERIAL | EXAMPLES OF MATERIAL | PUBLICATIONS |
|---|---|---|
| Rhenium (I), (II), and (III) complexes | 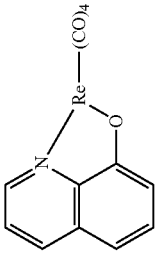 | US20050244673 |
| Green dopants | | |
| Iridium(III) organometallic complexes | 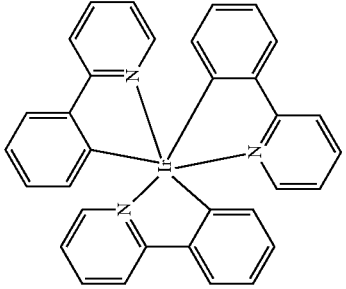 and its derivatives | Inorg. Chem. 40, 1704 (2001) |
| | 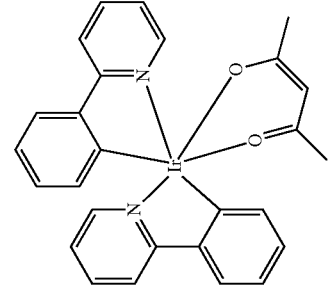 | US20020034656 |

TABLE 6-continued
| MATERIAL | EXAMPLES OF MATERIAL | PUBLICATIONS |
|---|---|---|
| | 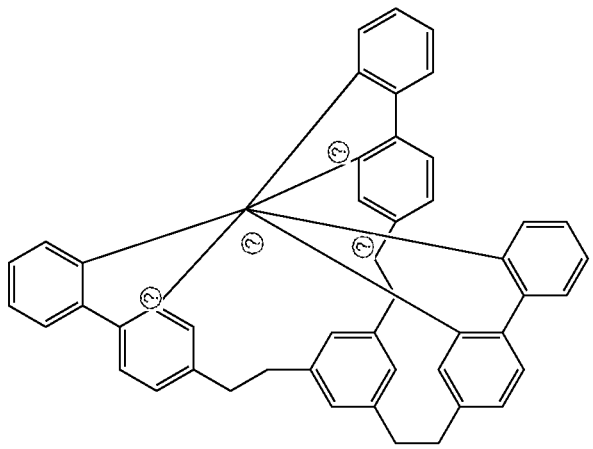 | U.S. Pat. No. 7,322,232 |
| | 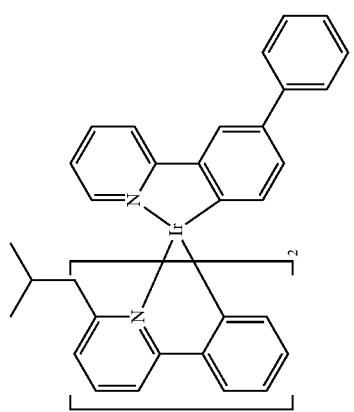 | US20090108737 |

TABLE 6-continued

| MATERIAL | EXAMPLES OF MATERIAL | PUBLICATIONS |
| --- | --- | --- |
| | | WO2010028151 |
| | | EP1841834B |
| | | US20060127696 |

TABLE 6-continued

| MATERIAL | EXAMPLES OF MATERIAL | PUBLICATIONS |
|---|---|---|
| | (structure) | US20090039776 |
| | (structure) | U.S. Pat. No. 6,921,915 |
| | (structure) | US20100244004 |

TABLE 6-continued
| MATERIAL | EXAMPLES OF MATERIAL | PUBLICATIONS |
|---|---|---|
| | 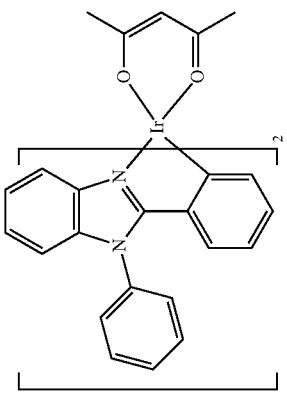 | U.S. Pat. No. 6,687,266 |
| | 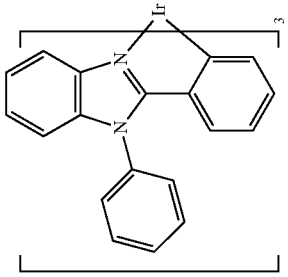 | Chem. Mater. 16, 2480 (2004) |
| | 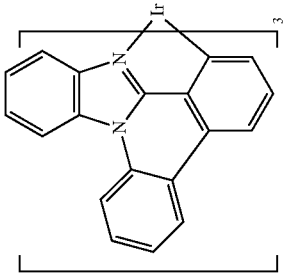 | US20070190359 |

TABLE 6-continued

| MATERIAL | EXAMPLES OF MATERIAL | PUBLICATIONS |
|---|---|---|
| | | US 20060008670 JP2007123392 |
| | | WO2010086089, WO2011044988 |
| | | Adv. Mater. 16, 2003 (2004) |
| | | Angew. Chem. Int. Ed. 2006, 45, 7800 |

TABLE 6-continued

| MATERIAL | EXAMPLES OF MATERIAL | PUBLICATIONS |
|---|---|---|
| | | WO2009050290 |
| | | US20090165846 |
| | | US20080015355 |
| | | US20010015432 |

TABLE 6-continued

| MATERIAL | EXAMPLES OF MATERIAL | PUBLICATIONS |
|---|---|---|
| | | US20100295032 |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |

TABLE 6-continued

| MATERIAL | EXAMPLES OF MATERIAL | PUBLICATIONS |
|---|---|---|
| | | Appl. Phys. Lett. 86, 153505 (2005) |
| | | Chem. Lett. 34, 592 (2005) |
| | | WO2002015645 |

TABLE 6-continued

| MATERIAL | EXAMPLES OF MATERIAL | PUBLICATIONS |
|---|---|---|
| | (structure) | US20060263635 |
| | (structure) | US20060182992<br>US20070103060 |
| Cu complexes | (structure) | WO2009000673 |

TABLE 6-continued

| MATERIAL | EXAMPLES OF MATERIAL | PUBLICATIONS |
|---|---|---|
| | | US20070111026 |
| Gold complexes | | Chem. Commun. 2906 (2005) |
| Rhenium(III) complexes | | Inorg. Chem. 42, 1248 (2003) |

TABLE 6-continued
| MATERIAL | EXAMPLES OF MATERIAL | PUBLICATIONS |
|---|---|---|
| Osmium(II) complexes | | U.S. Pat. No. 7,279,704 |
| Deuterated organometallic complexes | | US2003013865 |
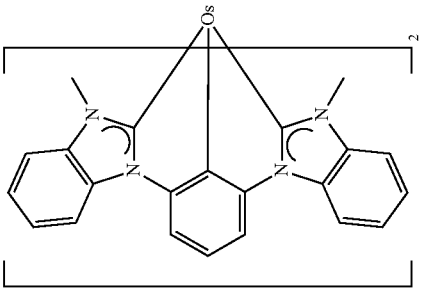

TABLE 6-continued
| MATERIAL | EXAMPLES OF MATERIAL | PUBLICATIONS |
|---|---|---|
| Organometallic complexes with two or more metal centers | 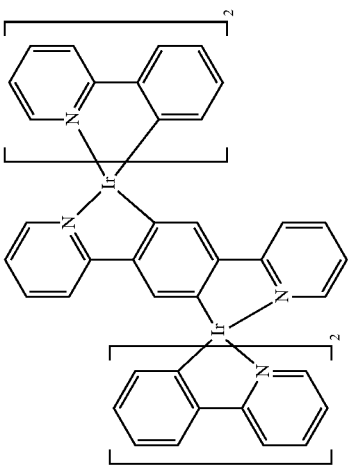 | US20030152802 |
| | 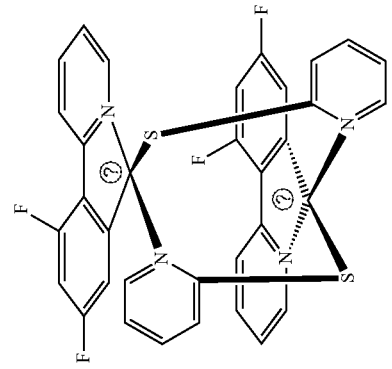 | U.S. Pat. No. 7,090,928 |
| Blue dopants | | |
| Iridium(III) organometallic complexes | 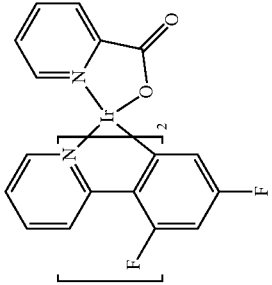 | WO2002002714 |

TABLE 6-continued
| MATERIAL | EXAMPLES OF MATERIAL | PUBLICATIONS |
|---|---|---|
| | 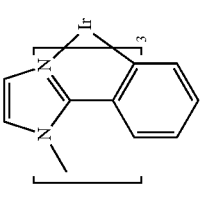 | WO2006009024 |
| | 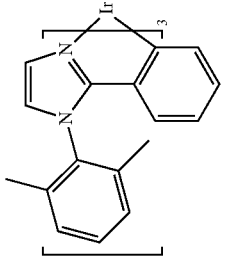 | US20060251923 US20110057559 US20110204333 |
| | 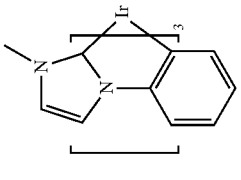 | U.S. Pat. No. 7,393,599, WO2006056418, US20050260441, WO2005019373 |
| | 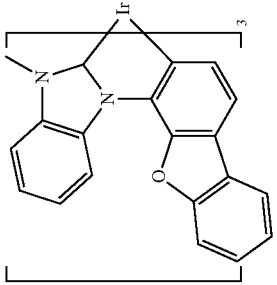 | U.S. Pat. No. 7,534,505 |

TABLE 6-continued
| MATERIAL | EXAMPLES OF MATERIAL | PUBLICATIONS |
|---|---|---|
| | 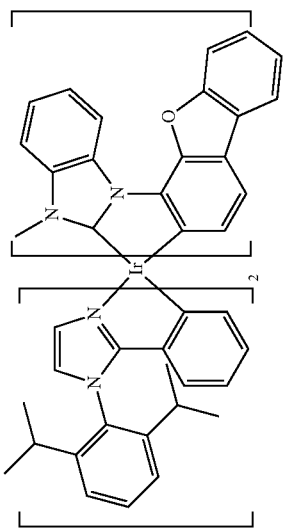 | WO2011051404 |
| | | U.S. Pat. No. 7,445,855 |
| | 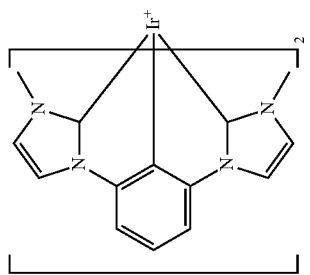 | US20070190359, US20080297033 US20100148663 |

TABLE 6-continued
| MATERIAL | EXAMPLES OF MATERIAL | PUBLICATIONS |
|---|---|---|
| | 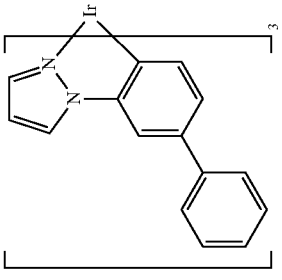 | U.S. Pat. No. 7,338,722 |
| | 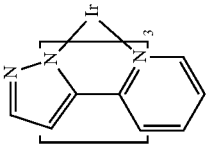 | US20020134984 |
| | 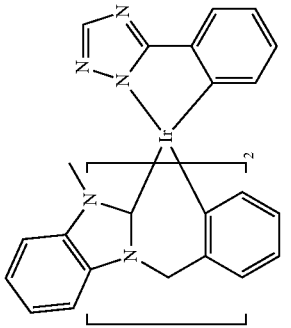 | Angew. Chem. Int. Ed. 47, 1 (2008) |
| | 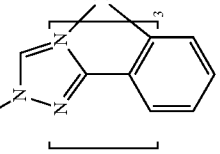 | Chem. Mater. 18, 5119 (2006) |

TABLE 6-continued

| MATERIAL | EXAMPLES OF MATERIAL | PUBLICATIONS |
|---|---|---|
| | | Inorg. Chem. 46, 4308 (2007) |
| | | WO2005123873 |
| | | WO2005123873 |

TABLE 6-continued
| MATERIAL | EXAMPLES OF MATERIAL | PUBLICATIONS |
|---|---|---|
| | 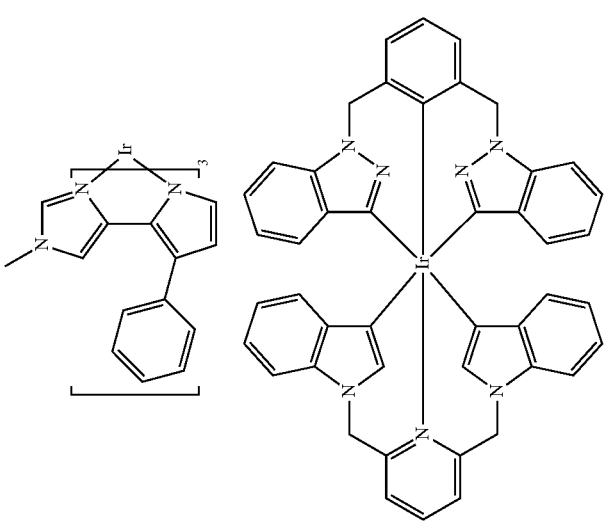 | WO2007004380 WO2006082742 |
| Osmium(II) complexes | 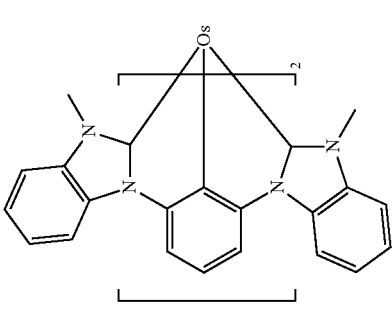 | U.S. Pat. No. 7,279,704 |

TABLE 6-continued

| MATERIAL | EXAMPLES OF MATERIAL | PUBLICATIONS |
|---|---|---|
| | | Organometallics 23, 3745 (2004) |
| Gold complexes | | Appl. Phys. Lett. 74, 1361 (1999) |
| Platinum(II) complexes | | WO2006098120, WO2006103874 |
| Pt tetradentate complexes with at least one metal-carbene bond | | U.S. Pat. No. 7,655,323 |

TABLE 6-continued
| MATERIAL | EXAMPLES OF MATERIAL | PUBLICATIONS |
|---|---|---|
| Exciton/hole blocking layer materials | | |
| Bathocuprine compounds (e.g., BCP, BPhen) | 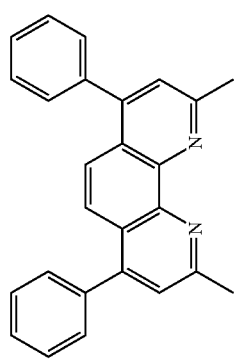 | Appl. Phys. Lett. 75, 4 (1999)<br><br>Appl. Phys. Lett. 79, 449 (2001) |
| Metal 8-hydroxyquinolates (e.g., BAlq) | 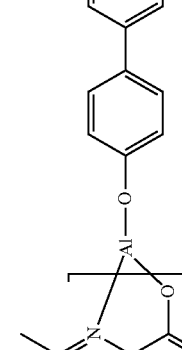 | Appl. Phys. Lett. 81, 162 (2002) |

TABLE 6-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 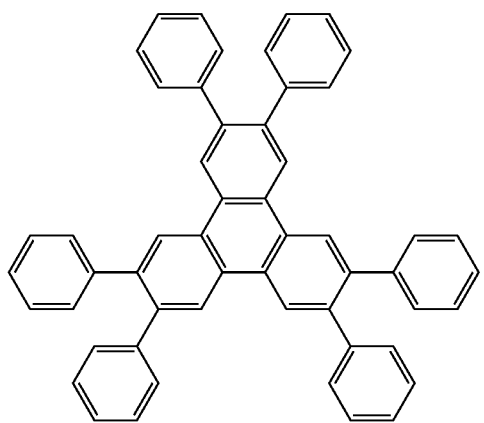 | Appl. Phys. Lett. 81, 162 (2002) |
| Triphenylene compounds | 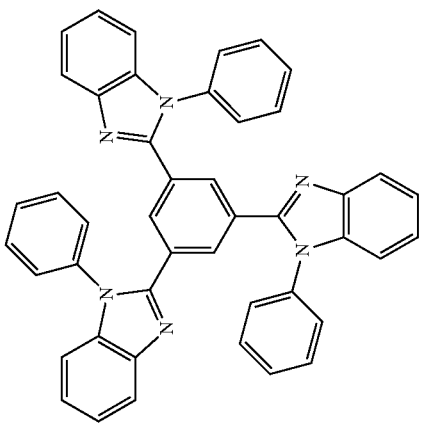 | US20050025993 |

TABLE 6-continued
| MATERIAL | EXAMPLES OF MATERIAL | PUBLICATIONS |
|---|---|---|
| Fluorinated aromatic compounds | 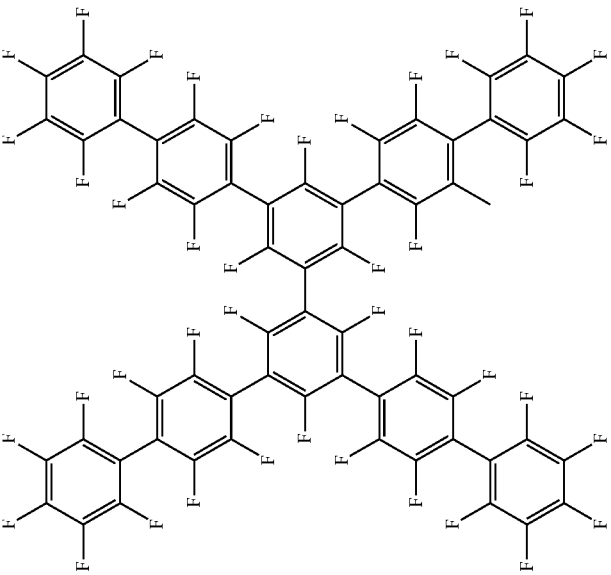 | Appl. Phys. Lett. 79, 156 (2001) |
| Phenothiazine-S-oxide | 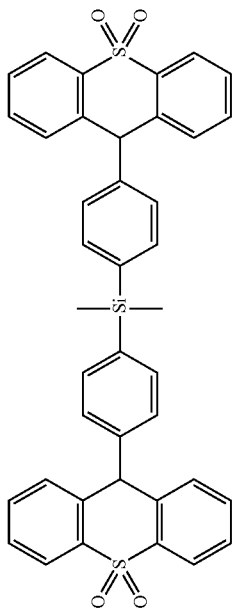 | WO2008013208 5 |

TABLE 6-continued
| MATERIAL | EXAMPLES OF MATERIAL | PUBLICATIONS |
|---|---|---|
| Silylated five-membered nitrogen, oxygen, sulfur or phosphorus dibenzoheterocycles | 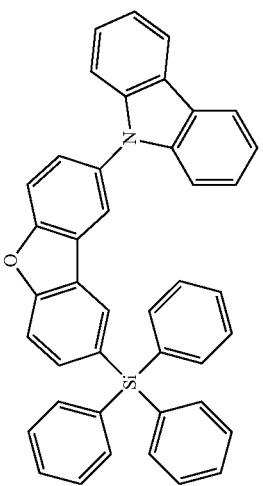 | WO2010079051 |
| Aza-carbazoles | 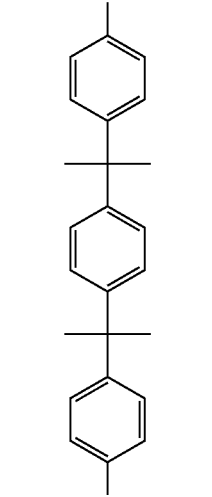 | US20060121308 |
| Electron transporting materials | | |
| Anthracene-benzoimidazole compounds | 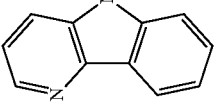 | WO2003060956 |

TABLE 6-continued
| MATERIAL | EXAMPLES OF MATERIAL | PUBLICATIONS |
|---|---|---|
| | 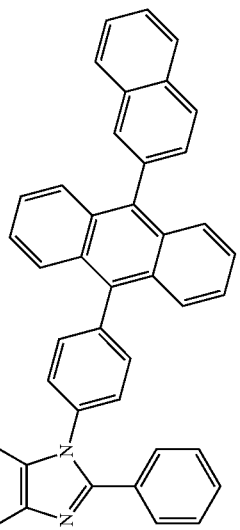 | US2009017554 |
| Aza triphenylene derivatives | 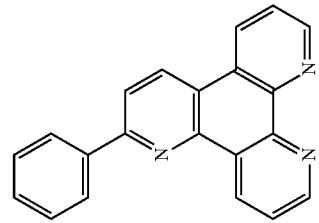 | US20090115316 |
| Anthracene-benzothiazole compounds | 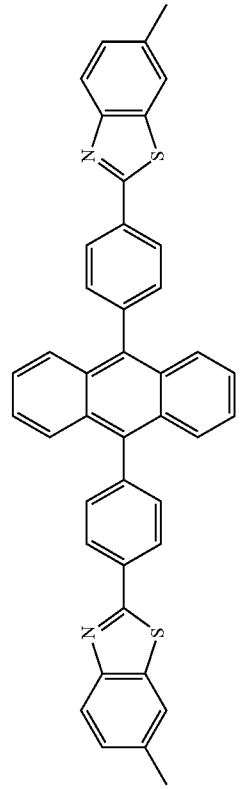 | Appl. Phys. Lett. 89, 063504 (2006) |

TABLE 6-continued
| MATERIAL | EXAMPLES OF MATERIAL | PUBLICATIONS |
|---|---|---|
| Metal 8-hydroxyquinolates (e.g., Alq$_3$, Zrq$_4$) | 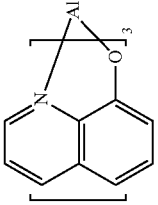 | Appl. Phys. Lett. 51, 913 (1987) U.S. Pat. No. 7,230,107 |
| Metal hydroxybenoquinolates | 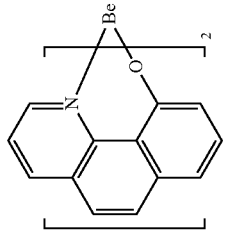 | Chem. Lett. 5, 905 (1993) |
| Bathocuprine compounds such as BCP, BPhen, etc | 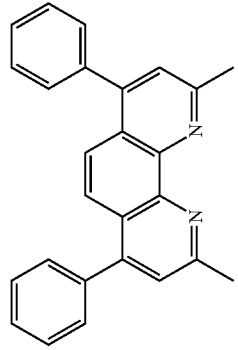 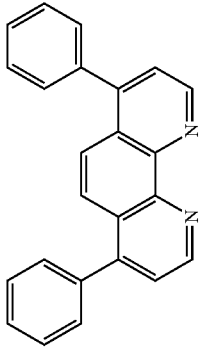 | Appl. Phys. Lett. 91, 263503 (2007) Appl. Phys. Lett. 79, 449 (2001) |

TABLE 6-continued
| MATERIAL | EXAMPLES OF MATERIAL | PUBLICATIONS |
|---|---|---|
| 5-member ring electron deficient heterocycles (e.g. triazole, oxadiazole, imidazole, benzoimidazole) | 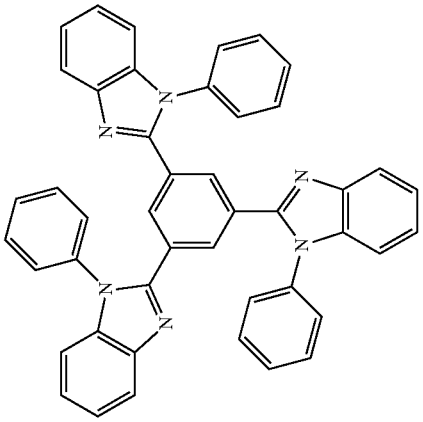 | Appl. Phys. Lett. 74, 865 (1999)<br><br>Appl. Phys. Lett. 55, 1489 (1989)<br><br>Jpn. J. Apply. Phys. 32, L917 (1993) |
| Silole compounds | 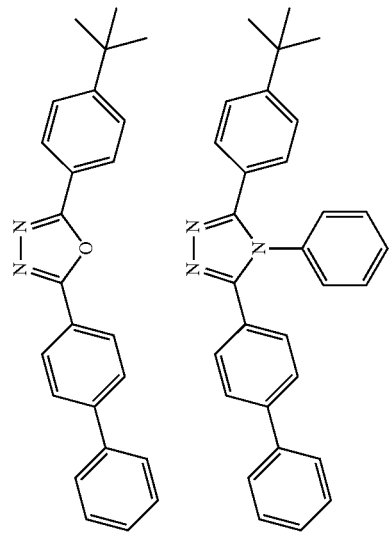 | Org. Electron. 4, 113 (2003) |

TABLE 6-continued

| MATERIAL | EXAMPLES OF MATERIAL | PUBLICATIONS |
| --- | --- | --- |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US2009010187O |

TABLE 6-continued
| MATERIAL | EXAMPLES OF MATERIAL | PUBLICATIONS |
|---|---|---|
| Triazine complexes | 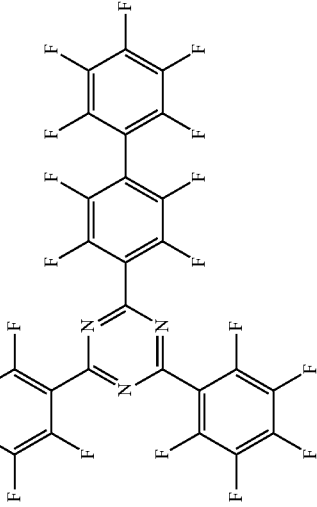 | US20040036077 |
| Zn (N^N) complexes | 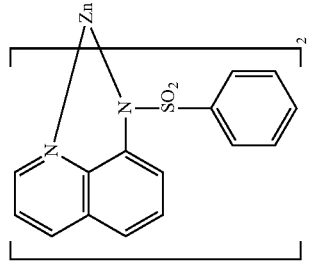 | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DCM is dichloromethane, S-Phos is dicyclohexyl(2',6'-dimethoxy-[1,1'-biphenyl]-2-yl)phosphine, DMSO is dimethyl sulfoxide, DBU is 1,8-diazabicyclo[5.4.0]undec-7-ene.

Synthesis of Compound 1

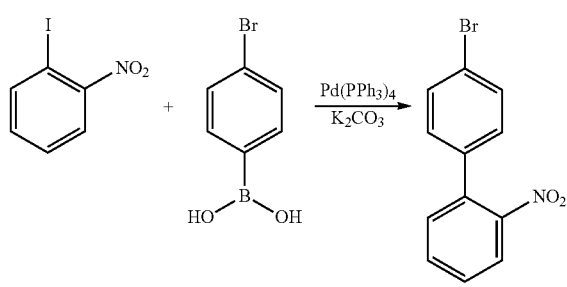

Synthesis of 4'-Bromo-2-nitro-1,1'-biphenyl

1-Iodo-2-nitrobenzene (28.2 g, 113 mmol), (4-bromophenyl)boronic acid (25 g, 124 mmol), Pd(PPh$_3$)$_4$ (1.3 g, 1.1 mmol), potassium carbonate (46.9 g, 340 mmol), DME (300 mL) and water (200 mL) were added to a flask and degassed with nitrogen for 20 minutes. The reaction was heated to reflux for 16 hours. The reaction was cooled to room temperature and 200 mL of EtOAc and 200 mL of water were added into reaction mixture. After separating the layers, the aqueous layer was washed twice with EtOAc and the combined organic layers were washed twice with water. The combined organic portion was dry over sodium sulfate, filtered and evaporated to dryness to give 34.3 g of an amber oil. It was then subjected to column chromatography (silica gel, 9/1 hexane/EtOAc, v/v) to yield 23.7 g (75%) of 4'-bromo-2-nitro-1,1'-biphenyl. The product was confirmed by GC/MS and NMR.

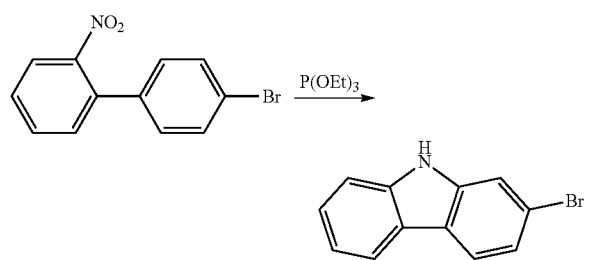

Synthesis of 2-Bromo-9H-carbazole

A round bottom flask was charged with 4'-bromo-2-nitro-1,1'-biphenyl (14.5 g, 52.1 mmol), triethyl phosphite (50 g, 301 mmol) and heated to reflux under nitrogen overnight. The reaction mixture was allowed to cool to room temperature and 60 mL of 6 N HCl was added dropwise. The reaction mixture was then heated to 80° C. for 3 hours. The reaction mixture was then cooled and neutralized with 50% NaOH, diluted with water and extracted with 3×150 mL EtOAc. The combined organic extracts were washed with 150 mL water and 150 mL brine, dried over MgSO$_4$ and evaporated to dryness. The lower boiling impurities were removed by Kugelrohr distillation and the residue was chromatographed (SiO$_2$, 9/1 hexane/EtOAc) to yield 8.4 g (65%) of 2-bromo-9H-carbazole as an off-white solid. The product was confirmed by GC/MS and NMR.

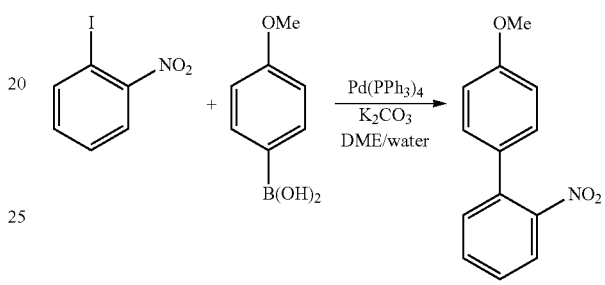

Synthesis of 4'-Methoxy-2-nitro-1,1'-biphenyl

In a 500 mL three-neck round-bottom flask was added 1-iodo-2-nitrobenzene (24.6 g, 99 mmol), (4-methoxyphenyl)boronic acid (15 g, 99 mmol), potassium carbonate (41 g, 296 mmol) and Pd(PPh$_3$)$_4$ (5.7 g, 4.9 mmol) with 300 mL of DME and 200 mL of water. The reaction mixture was degassed for 30 minutes and heated to reflux for 18 hours. The reaction mixture was cooled to room temperature, the aqueous layer was removed and the organic portion was evaporated to dryness. The crude material was chromatographed on silica with 8/2 hexane/EtOAc (v/v) to yield 19.9 g (88%) of 4'-methoxy-2-nitro-1,1'-biphenyl. The product was confirmed by GC/MS and NMR.

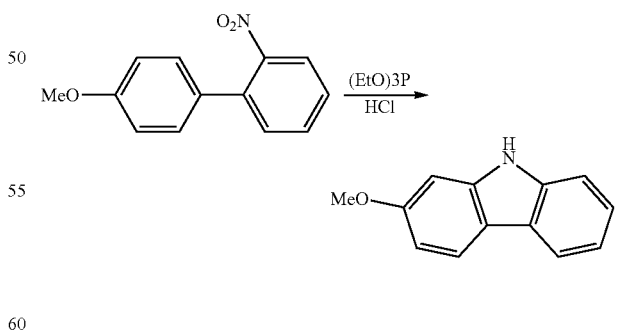

Synthesis of 2-methoxy-9H-carbazole

In a 500 mL round-bottom flask was added 4'-methoxy-2-nitro-1,1'-biphenyl (10.3 g, 44.7 mmol) and triethyl phosphite (44.2 mL, 258 mmol). The reaction mixture was heated to reflux at 165° C. in an oil bath under nitrogen for 18 hours. The reaction mixture was cooled to room temperature and 60 mL of 6 N HCl was added dropwise over a period of 30 min. with continuous stirring (exothermic reaction). After the addition, the reaction was heated for 3 hours at 80° C., resulting in the formation of copious precipitate. After cooling to room temperature, water was added (100 mL) and the reaction mixture was neutralized with 50% NaOH (aq.) (60-70 mL, exothermic reaction). The resulting mixture was extracted with 3×250 mL EtOAc and the combined organic layers were washed with brine, dried over Na$_2$SO$_4$, filtered and solvent removed under reduced pressure. To this was added ~5-10 mL DCM and the insoluble solid was filtered and washed with hexane to give 6.2 g (70%) of 2-methoxy-9H-carbazole as a light yellow solid. The product was confirmed by GC/MS and NMR.

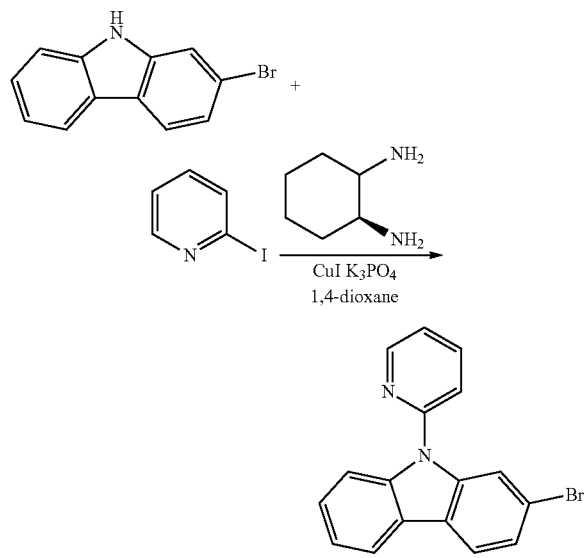

Synthesis of 2-Bromo-9-(pyridin-2-yl)-9H-carbazole

A 100 mL 3-neck flask was charged with copper iodide (0.057 g, 0.301 mmol), 2-bromo-9H-carbazole (7.4 g, 30.1 mmol), 2-iodopyridine (12.3 g, 60.1 mmol), potassium phosphate (12.8 g, 60.1 mmol), (1R,4R)-cyclohexane-1,4-diamine (0.343 g, 3.0 mmol) and dioxane (25 mL) and the reaction mixture was heated at 65° C. overnight. The reaction mixture was poured into water and extracted with dichloromethane. The organic layers were combined and subjected to column chromatography (neutral Al$_2$O$_3$, 99/1 hexane/EtOAc, v/v) to yield 4.2 g (43%) of 2-bromo-9-(pyridin-2-yl)-9H-carbazole as a white solid. The product was confirmed by GC/MS and NMR.

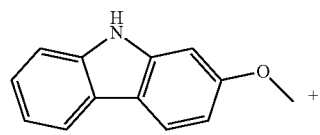

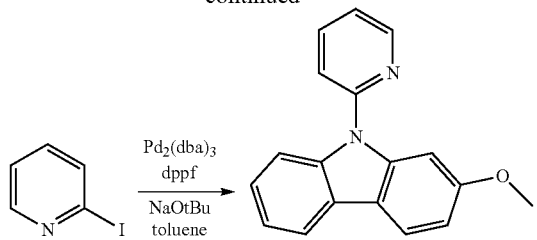

Synthesis of 2-Methoxy-9-(pyridin-2-yl)-9H-carbazole

A 1 L three-neck round-bottom flask was charged with 2-methoxy-9H-carbazole (4.6 g, 23.2 mmol), 2-iodopyridine (3.1 ml, 29.0 mmol), 1,1'-bis(diphenylphosphino)ferrocene (0.514 g, 0.927 mmol), Pd$_2$(dba)$_3$ (0.424 g, 0.463 mmol), sodium tert-butoxide (3.12 g, 32.4 mmol) and toluene (150 mL). The reaction mixture was degassed for 20 minutes and heated to reflux for 18 hours. The reaction mixture was cooled to room temperature and diluted with water. The aqueous layer was extracted three times with EtOAc and the combined organic layers were concentrated. The crude material was chromatographed on silica with 85/15 hexane/EtOAc (v/v) to 70/30 hexane/EtOAc (v/v) to yield 5.5 g (60%) of 2-methoxy-9-(pyridin-2-yl)-9H-carbazole as an off-white solid. The product was confirmed by GC/MS and NMR.

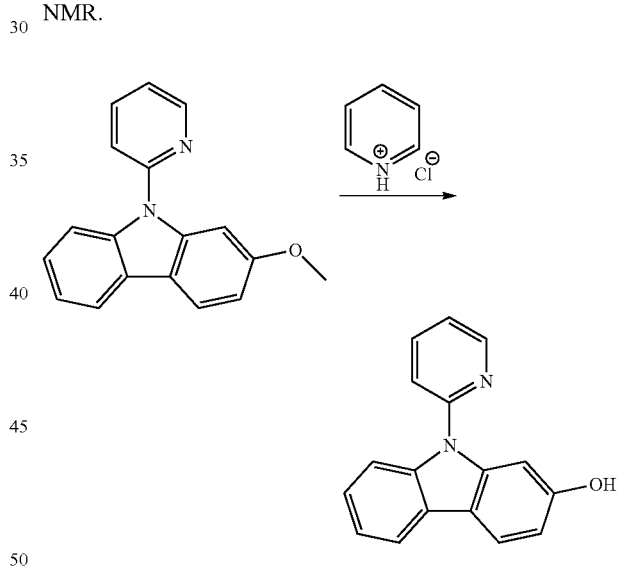

Synthesis of 9-(pyridin-2-yl)-9H-carbazol-2-ol

To a 250 mL three-neck round-bottom flask was added 2-methoxy-9-(pyridin-2-yl)-9H-carbazole (5.49 g, 20.01 mmol) and pyridinium hydrochloride (18.5 g, 160 mmol). The reaction mixture was heated to 200° C. for 18 hours. The reaction mixture was cooled to 90° C. and water was slowly added and the reaction mixture stirred until all the solids were broken down to small particles as it cooled to room temperature. The reaction mixture was extracted with EtOAc and the combined organic layers were combined and concentrated. The crude material was chromatographed on silica with 85/15 hexane/EtOAc (v/v) to 70/30 hexane/EtOAc (v/v) to yield 3.7 g (60%) of 9-(pyridin-2-yl)-9H-carbazol-2-ol as an off-white solid. The product was confirmed by NMR.

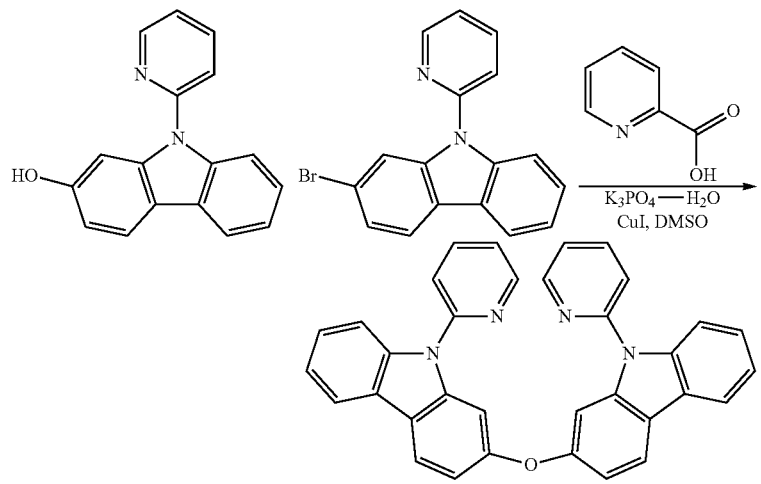

Synthesis of 2,2'-Oxybis(9-(pyridin-2-yl)-9H-carbazole)

A 250 mL round bottom flask was charged with 9-(pyridin-2-yl)-9H-carbazol-2-ol (1.2 g, 4.4 mmol), 2-bromo-9-(pyridin-2-yl)-9H-carbazole (1.7 g, 5.3 mmol), picolinic acid (0.22 g, 1.8 mmol), copper(I) iodide (0.17 g, 0.88 mmol) and potassium phosphate (2.0 g, 8.8 mmol) in DMSO (100 mL) to give a brown suspension. The reaction mixture was heated to 120° C. for 20 hours. The solvent was removed by vacuum distillation and the residue was chromatographed on silica with 1/1 hexane/EtOAc (v/v) to yield 1.6 g (70%) of 2,2'-oxybis(9-(pyridin-2-yl)-9H-carbazole) as a white solid. The product was confirmed by NMR.

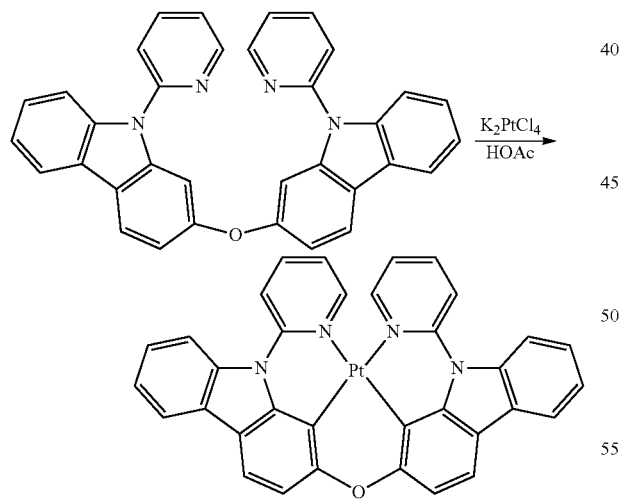

Synthesis of Compound 1

2'-Oxybis(9-(pyridin-2-yl)-9H-carbazole) (1.6 g, 3.1 mmol) and potassium tetrachloroplatinate (1.3 g, 3.1 mmol) were added to acetic acid (130 mL) and the mixture was degassed thoroughly with nitrogen before heating to 130° C. (bath temp.). After heating for 40 hours, the reaction was cooled to room temperature and the solvent was removed by rotatory evaporation. The residue was poured into a saturated sodium carbonate aqueous solution and extracted with ethyl acetate. The organic portions were combined and subjected to column chromatography with 1/1 hexane/ethyl acetate (v/v) on a silica column pre-treated with triethylamine to yield 1.2 g (55%) of Compound 1 as a yellow solid. The product was confirmed by LC/MS and NMR.

Synthesis of Compound 2

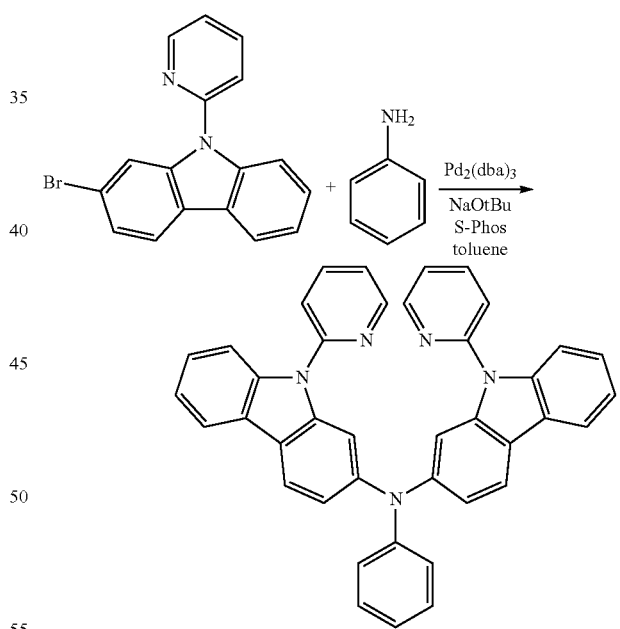

Synthesis of N-Phenyl-9-(pyridin-2-yl)-N-(9-(pyridin-2-yl)-9H-carbazol-2-yl)-9H-carbazol-2-amine 2-Bromo-9-(pyridin-2-yl)-9H-carbazole (4.4 g, 13.6 mmol), dicyclohexyl(2',6'-dimethoxy-[1,1'-biphenyl]-2-yl)phosphine (0.224 g, 0.545 mmol), $Pd_2(dba)_3$ (0.125 g, 0.136 mmol) and sodium tert-butoxide (2.0 g, 20.4 mmol) were added to toluene (100 mL) and then aniline (0.622 ml, 6.81 mmol) was added. The reaction was degassed with nitrogen before being heated to reflux overnight. After cooling to room temperature, the reaction mixture was filtered through a bed of Celite®, and washed with DCM. After removal of solvent under reduced pressure, the crude material was first chromatographed on a silica gel column with DCM and then on a neutral alumina column with 7/3 hexane/DCM (v/v) to 5/5 hexane/DCM (v/v) to give 3.8 g (97%) of N-phenyl-9-(pyridin-2-yl)-N-(9-(pyridin-2-yl)-9H-carbazol-2-yl)-9H-carbazol-2-amine as white needles (HPLC purity: 99.6%). The product was confirmed by NMR.

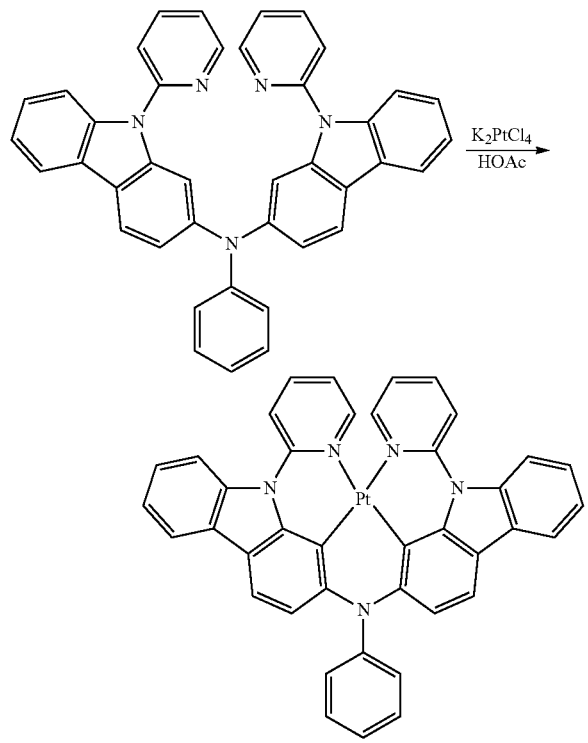

Synthesis of Compound 2

N-Phenyl-9-(pyridin-2-yl)-N-(9-(pyridin-2-yl)-9H-carbazol-2-yl)-9H-carbazol-2-amine (3.8 g, 6.6 mmol) and potassium tetrachloroplatinate (2.7 g, 6.6 mmol) were added to acetic acid (100 mL) and the mixture was degassed for 20 minutes with nitrogen before being heated to 130° C. (bath temp.) overnight. After cooling to room temperature, water was added and the mixture stirred for 20 minutes before the solid was filtered off, the solid collected was chromatographed on silica with DCM to give 0.1 g (2%) compound 2 as a yellow solid (HPLC purity: 99.5%). The product was confirmed by LC/MS and NMR.

Synthesis of Compound 7

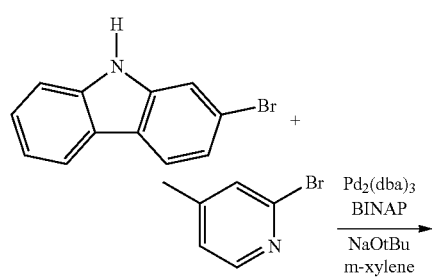

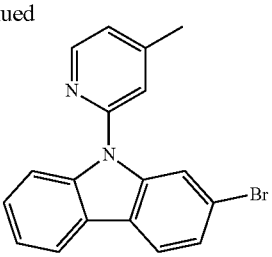

Synthesis of 2-Bromo-9-(4-methylpyridin-2-yl)-9H-carbazole

In a 500 mL three-neck round-bottom flask was added 2,2'-bis(diphenylphosphino)-1,1'-binaphthalene (1.1 g, 1.8 mmol), Pd$_2$(dba)$_3$ (0.56 g, 0.61 mmol) in 250 mL of m-xylene. The reaction mixture was degassed by bubbling nitrogen for 30 minutes and heated to 80° C. for 15 minutes. The reaction mixture was cooled to room temperature and 2-bromo-9H-carbazole (5.0 g, 20.3 mmol), 2-bromo-4-methylpyridine (4.2 g, 24.4 mmol) and sodium tert-butoxide (2.9 g, 30.5 mmol) were added. The reaction was again degassed for 15 minutes and heated to reflux for 18 hours. After cooling to room temperature, the reaction mixture was diluted with 250 mL of water and extracted with EtOAc (3×150 mL). The combined organic layers were washed with water (2×150 mL), brine (1×150 mL) and dried over NaSO$_4$. After removal of the solvents under reduced pressure, the crude material was first chromatographed on a silica gel column with DCM and then on a neutral alumina column with 3/1 hexane/DCM (v/v) to give 2.8 g (40%) of 2-Bromo-9-(4-methylpyridin-2-yl)-9H-carbazole as a white solid. The product was confirmed by GC/MS and NMR.

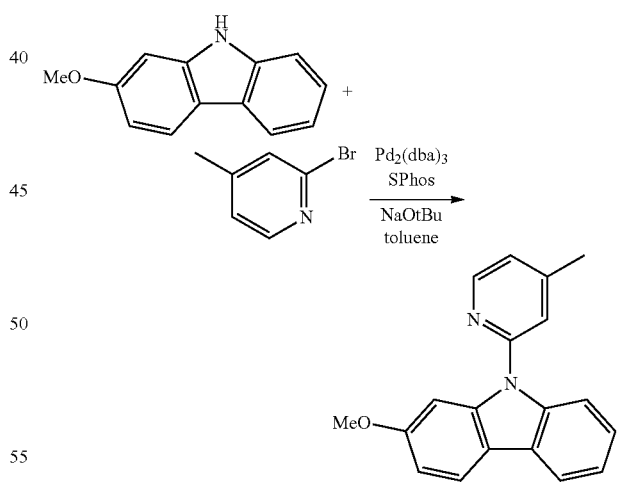

Synthesis of 2-Methoxy-9-(4-methylpyridin-2-yl)-9H-carbazole

In a 500 mL three-neck round-bottom flask was added 2-methoxy-9H-carbazole (6.2 g, 31.5 mmol), 2-bromo-4-methylpyridine (3.9 mL, 34.7 mmol), dicyclohexyl(2',6'-dimethoxy-[1,1'-biphenyl]-2-yl)phosphine (1.3 g, 3.2 mmol), Pd$_2$(dba)$_3$ (1.4 g, 1.6 mmol) and sodium tert-butoxide (4.6 g, 47.3 mmol) with 230 mL of toluene. The reaction mixture was degassed for 20 min. and heated to reflux at 125° C. in an oil bath under nitrogen for 18 h. After cooling to room temperature, the reaction mixture was passed through a tightly packed Celite® plug, washing with DCM and EtOAc. After removal of the solvents under reduced pressure, the crude material was first chromatographed on a silica gel column with 95/5 hexane/EtOAc (v/v) to 85/15 hexane/EtOAc (v/v) to give 8.9 g (98%) of 2-methoxy-9-(4-methylpyridin-2-yl)-9H-carbazole as a white solid. The product was confirmed by GC/MS and NMR.

Synthesis of 9-(4-methylpyridin-2-yl)-9H-carbazol-2-ol

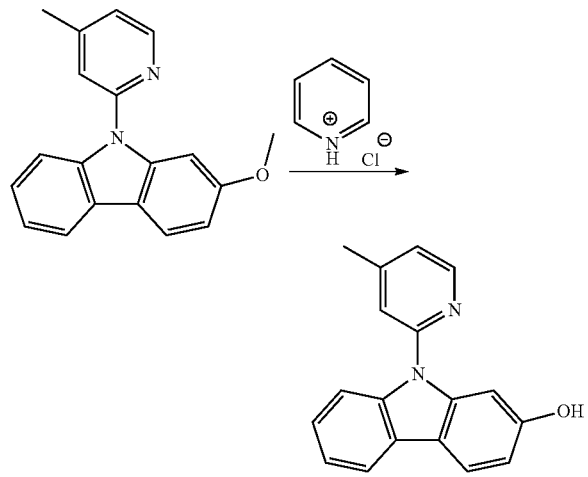

In a 500 mL round bottom flask was added 2-methoxy-9-(4-methylpyridin-2-yl)-9H-carbazole (8.9 g, 31 mmol) and pyridinium hydrochloride (28.7 g, 248 mmol). The reaction mixture was heated to 200° C. for 18 hours with continuous stirring. The reaction mixture was cooled to 90° C. and water was slowly added and the reaction mixture stirred until all the solids were broken down to small particles as it cooled to room temperature. The reaction mixture was extracted with EtOAc and the combined organic layers were combined and concentrated. The crude material was chromatographed on silica with 85/15 hexane/EtOAc (v/v) to 70/30 hexane/EtOAc (v/v) to yield 4.6 g (54%) of 9-(4-methylpyridin-2-yl)-9H-carbazol-2-ol as an off-white solid. The product was confirmed by NMR.

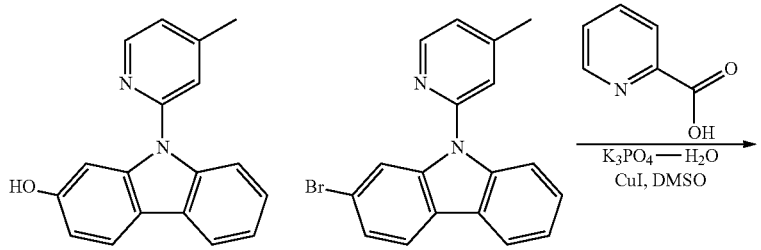

Synthesis of 2,2'-oxybis(9-(4-methylpyridin-2-yl)-9H-carbazole

To a 250 mL three-neck round-bottom flask was added 2-bromo-9-(4-methylpyridin-2-yl)-9H-carbazole (1.5 g, 4.5 mmol), 9-(4-methylpyridin-2-yl)-9H-carbazol-2-ol (1.3 g, 4.9 mmol), copper(I) iodide (0.25 g, 1.3 mmol), picolinic acid (0.82 g, 6.7 mmol) and potassium phosphate tribasic monohydrate (3.6 g, 15.6 mmol) in 100 mL of DMSO. The reaction mixture was heated to 150° C. for 20 hours. The solvent was removed by vacuum distillation and the residue was chromatographed on silica with DCM followed by 99/1 DCM/EtOAc (v/v) to yield 1.9 g (78%) of 2,2'-oxybis(9-(4-methylpyridin-2-yl)-9H-carbazole as a white solid. The product was confirmed by NMR.

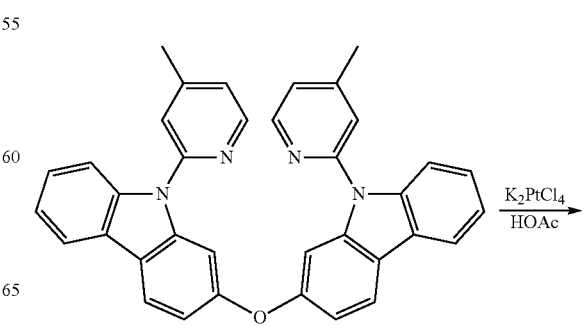

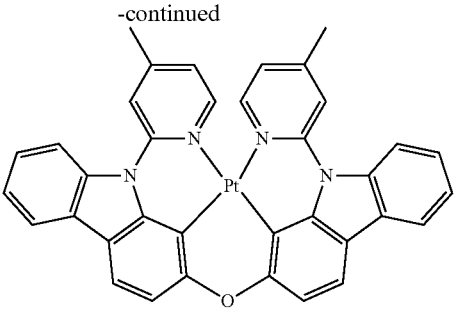

Synthesis of Compound 7

To a 250 mL round-bottom flask was added 2,2'-oxybis(9-(4-methylpyridin-2-yl)-9H-carbazole) (1.9 g, 3.5 mmol) and potassium tetrachloroplatinate(II) (1.4 g, 3.5 mmol) with 100 mL of acetic acid. The reaction mixture was degassed with nitrogen for 20 minutes and was stirred in an oil bath at 140° C. for 18 hours. After cooling to room temperature, 100 mL of water was added causing copious gray precipitate to form. The precipitate was filtered and washed with water (3×50 mL). The solid was dissolved in DCM and was dried over $Na_2SO_4$, filtered and concentrated. The crude material was chromatographed on silica gel, eluting with dichloromethane to give a yellow solid after evaporation. The solid was dissolved in DCM and precipitated with hexane. The solid was filtered, washed with hexane and dried to give 1.5 g (58%) of Compound 7 as a crystalline yellow solid (HPLC purity: 99.4%). The product was confirmed by LC/MS and NMR.

Synthesis of Compound 22

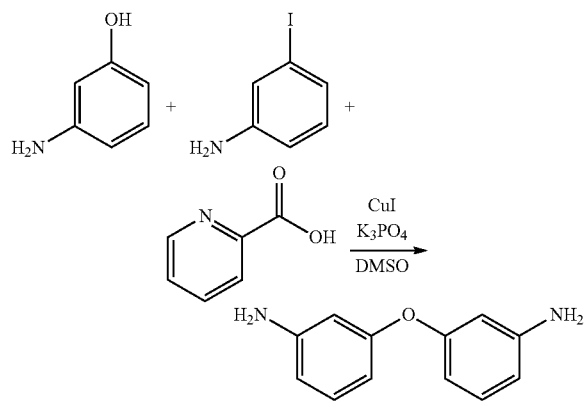

Synthesis of 3,3'-oxydianiline

3-Aminophenol (6.0 g, 54.8 mmol), 3-iodoaniline (10.0 g, 45.7 mmol), picolinic acid (0.56 g, 4.6 mmol), copper(I) iodide and potassium phosphate (19.4 g, 91 mmol) were added to DMSO (100 mL) and the reaction mixture degassed by bubbling nitrogen into the mixture for 1 hour. The reaction flask was then placed into a preheated 80° C. oil bath and stirred for 15 hours before cooling to room temperature. The reaction mixture was then poured into 150 mL of water and extracted with 3×50 mL EtOAc. The combined organics were washed with 50 mL water, 50 mL brine, dried and evaporated. The crude oil was chromatographed on silica with 80/20 hexane/EtOAc (v/v) followed by 50/50 hexane/EtOAc (v/v) to give 7.2 g (79%) of 3,3'-oxydianiline as a white solid. The product was confirmed by GC/MS and NMR.

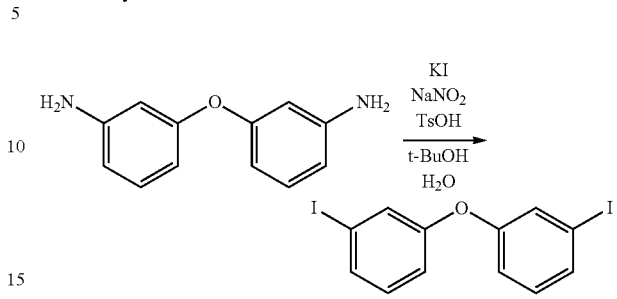

Synthesis of 3,3'-oxybis(iodobenzene)

To a suspension of p-toluenesulfonic acid hydrate (30.8 g, 162 mmol) in tert-butylalcohol (110 mL) and water (5 mL) was added 3,3'-oxydianiline (3.6 g, 17.9 mmol) and the reaction mixture cooled to 10° C. in an ice/water bath. A solution of sodium nitrite (7.4 g, 108 mmol) and potassium iodide (22.4 g, 135 mmol) in water (30 mL) was added dropwise over 1 hour, keeping the temperature below 15° C. The cold bath was removed and the reaction mixture allowed to warm to room temperature and stirred for another 3 hours. To the reaction mixture was added 15 g $NaHCO_3$ to pH ~8 followed by 35 g $Na_2S_2O_3$ and the mixture stirred for 30 minutes before being poured into 300 mL of water. The mixture was extracted 2×100 mL with ether and 3×100 mL DCM. The combined extracts were washed with 2×100 mL water, dried over sodium sulfate and evaporated leaving 4.5 g of a dark liquid. The crude oil was chromatographed on silica with hexane to give 4.8 g (79%) of 3,3'-oxybis(iodobenzene) as a white solid. The product was confirmed by GC/MS and NMR.

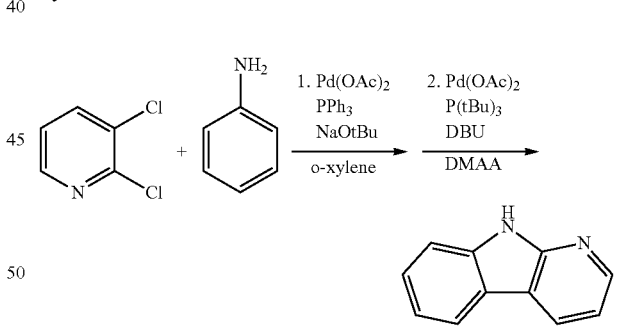

Synthesis of 9H-pyrido[2,3-b]indole 2,3-Dichloropyridine (15 g, 101 mmol), aniline (10.2 mL, 111 mmol), palladium(II) acetate (1.1 g, 5.1 mmol), sodium tert-butoxide (11.7 g, 122 mmol), triphenylphosphine (2.7 g, 10.1 mmol) and o-xylene (100 mL) were combined and degassed by bubbling nitrogen into the mixture for 1 hour. The reaction mixture was then heated in the dark at 120° C. for 3 hours, before being allowed to cool to room temperature. In a separate flask tri(tert-butyl)phosphine (10.1 mL, 10.1 mmol), palladium(II) acetate (1.1 g, 5.1 mmol) and DBU (30.9 g, 203 mmol) were added followed by dimethylacetamide (100 mL). The solution was degassed with nitrogen for 1 hour before being transferred to the reaction mixture and heating to 150° C. for 12 hours. After cooling to room temperature, 250 mL of water was added and the mixture extracted with 4×100 mL EtOAc. The combined extracts were washed with 2×100 mL water, 2×100 mL 10% LiCl (aq.), dried over sodium sulfate and evaporated to give a black solid. The crude product was chromatographed on silica gel with DCM followed by 90/10 DCM/EtOAc (v/v) and finally 90/10 DCM/EtOAc (v/v) to give the product as a brown solid (5.7 g, 33%). The product was confirmed by GC/MS and NMR.

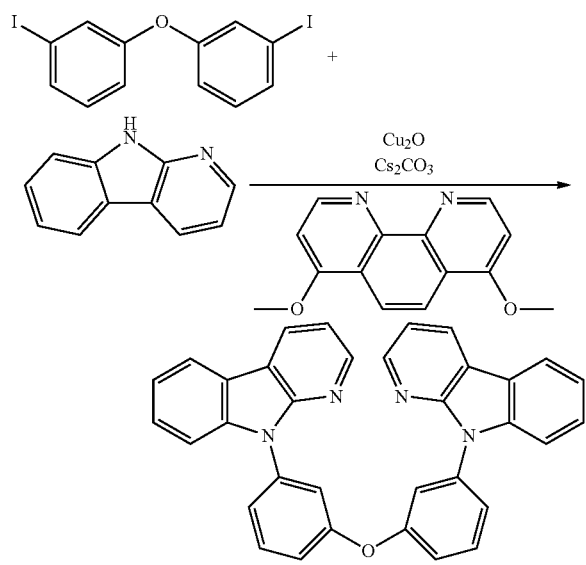

Synthesis of 9,9'-(oxybis(3,1-phenylene))bis(9H-pyrido[2,3-b]indole)

3,3'-Oxybis(iodobenzene) (2.1 g, 5.0 mmol), 9H-pyrido[2,3-b]indole (1.8 g, 10.5 mmol), copper(I) oxide (0.014 g, 0.100 mmol), 4,7-dimethoxy-1,10-phenanthroline (0.048 g, 0.199 mmol), cesium carbonate (3.2 g, 9.9 mmol) and DMSO (100 mL) were combined and degassed for 15 minutes. The reaction mixture was heated to 130° C. for 5 hours and then 160° C. overnight. After cooling, 150 mL of water was added and the mixture extracted with 2×75 mL DCM and 2×75 mL EtOAc. The combined extracts were washed with 150 mL water, 150 mL brine, dried over sodium sulfate and evaporated. The crude material was chromatographed on silica with 95/5 DCM/EtOAc (v/v) to give 2.3 g (92%) of 9,9'-(oxybis(3,1-phenylene))bis(9H-pyrido[2,3-b]indole) as a white solid. The product was confirmed by NMR.

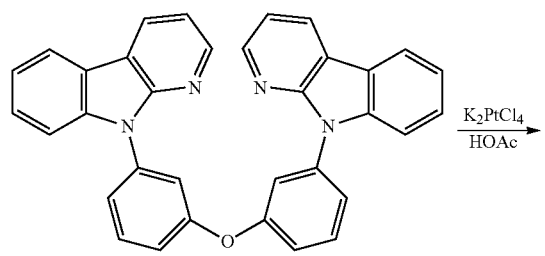

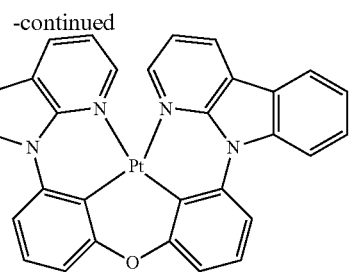

Synthesis of Compound 22

9,9'-(oxybis(3,1-phenylene))bis(9H-pyrido[2,3-b]indole) (2.1 g, 4.18 mmol) and potassium tetrachloroplatinate (1.7 g, 4.2 mmol) were added to acetic acid (70 mL) and the mixture was degassed thoroughly with nitrogen before heating to 130° C. (bath temp.). After 16 hours, the reaction was cooled to room temperature and 100 mL of water was added. After stirring for 20 minutes, the reaction mixture was filtered through a small bed of Celite® and the yellow solid washed with copious water and then MeOH. After drying, the solid was washed off the Celite® with DCM. The resulting filtrate was evaporated to give 2.2 g of a yellow solid. The crude material was chromatographed on silica gel with DCM to give 0.9 g (31%) of Compound 22 as a yellow solid (HPLC purity: 99.5%). The product was confirmed by LC/MS and NMR.

Synthesis of Compound 88

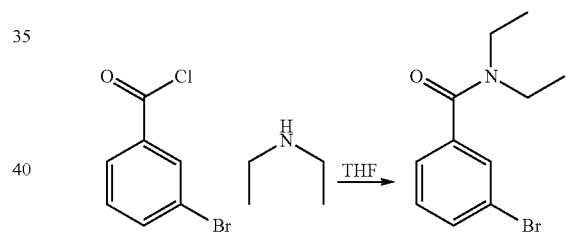

Synthesis of 3-Bromo-N,N-diethylbenzamide

A 1 L round-bottomed flask was charged with 3-bromobenzoyl chloride (25.4 g, 116 mmol) in THF (350 mL) and cooled to 0° C. Diethylamine (25.9 mL, 254 mmol) was added dropwise and temperature was maintained at 0° C. and the reaction mixture was allowed to warm to room temperature and stirred for 16 hours. The reaction mixture was diluted with 500 mL of ethyl acetate, filtered and the filtrate was washed with saturated ammonium chloride solution and brine. The organic portion was evaporated to dryness to give 29.4 g (99%) of 3-bromo-N,N-diethylbenzamide.

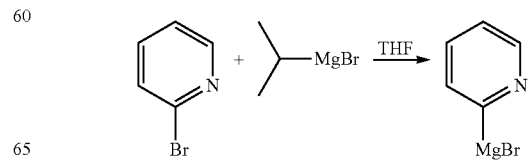

Synthesis of Pyridin-2-ylmagnesium bromide

A 100 mL round-bottomed flask was charged with 2-bromopyridine (6.9 mL, 72.7 mmol) and isopropylmagnesium bromide (40 mL, 80 mmol, 2 M solution in THF) was added dropwise into the reaction mixture at 0° C. After the addition was complete, the reaction was allowed to slowly warm to room temperature and stirred overnight. The reaction mixture was used for the next step without purification.

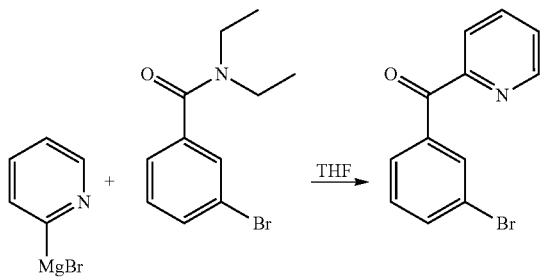

Synthesis of (3-Bromophenyl)(pyridin-2-yl)methanone

To a 250 mL round-bottomed flask was added pyridin-2-ylmagnesium bromide (13.3 g, 72.7 mmol) in THF (40 mL) to give a white suspension. 3-Bromo-N,N-diethylbenzamide (20.5 g, 80 mmol) in 50 mL of anhydrous THF was added into the reaction mixture over a period of 1 hour. The reaction mixture was stirred at room temperature for 48 hours and then quenched by adding cold saturated ammonium chloride aqueous solution. The mixture was extracted with toluene and the organic portion was subjected to column chromatography (SiO$_2$, 15% THF in hexanes) to yield 15.3 g (80%) of (3-bromophenyl)(pyridin-2-yl)methanone.

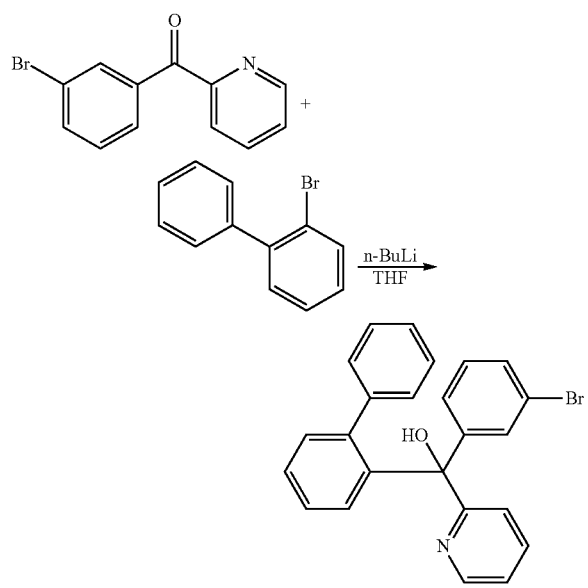

Synthesis of [1,1'-Biphenyl]-2-yl(3-bromophenyl)(pyridin-2-yl)methanol

A 500 mL round-bottom flask was charged with 3-bromo-1,1'-biphenyl (15.6 g, 64.2 mmol) and THF (180 mL) to give a colorless solution. n-Butyllithium (26.9 ml, 67.1 mmol, 2.5 Min hexanes) was added dropwise at −78° C. and the reaction mixture was stirred at −78° C. for 40 minutes. [1,1'-Biphenyl]-2-yl(3-bromophenyl)(pyridin-2-yl)methanol (23.9 g, 57.6 mmol) in 100 mL of THF was added dropwise to the reaction mixture via an additional funnel at −78° C. After the addition was completed, the reaction mixture was warmed to room temperature and stirred for 16 hours. The reaction mixture was dumped into aqueous ammonium chloride solution and extracted with ethyl acetate. The organic layer was combined and subjected to column chromatography (SiO$_2$, 10% THF in hexanes) to yield 24.0 g (99%) of [1,1'-biphenyl]-2-yl(3-bromophenyl)(pyridin-2-yl)methanol.

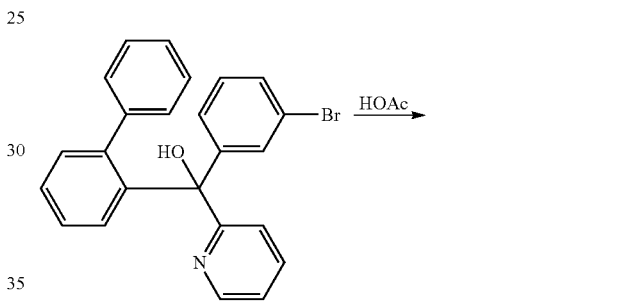

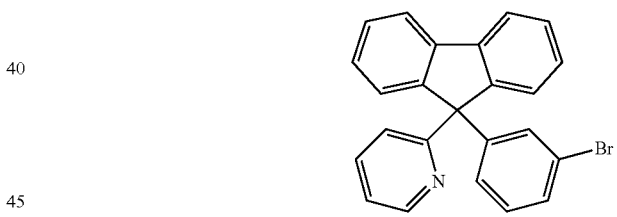

Synthesis of 2-(9-(3-Bromophenyl)-9H-fluoren-9-yl)pyridine

A 500 mL round-bottomed flask was charged with [1,1'-biphenyl]-2-yl(3-bromophenyl)(pyridin-2-yl)methanol (24.0 g, 57.6 mmol), acetic acid (105 mL) and concentrated HCl (1.5 mL) to give a brown solution. The reaction was heated to 110° C. for 24 hours, cooled to room temperature and the solvent was evaporated. The residue was dissolved in dichloromethane and washed with saturated sodium carbonated aqueous solution. The organic portion was combined and evaporated to dryness. The residue was subjected to column chromatography (SiO$_2$, 30% THF in hexanes) to yield 13.7 g (60%) of 2-(9-(3-bromophenyl)-9H-fluoren-9-yl)pyridine.

201

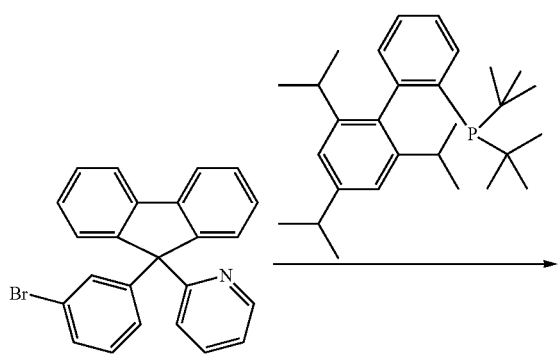

Synthesis of 3-(9-(pyridin-2-yl)-9H-fluoren-9-yl)phenol

In a 100 mL round-bottomed flask was charged with 2-(9-(3-bromophenyl)-9H-fluoren-9-yl)pyridine (3 g, 7.53 mmol), potassium phosphate (4.00 g, 18.83 mmol), Pd₂(dba)₃ (0.276 g, 0.301 mmol), di-tert-butyl(2',4',6'-triisopropyl-[1',1'-biphenyl]-2-yl)phosphine (0.512 g, 1.205 mmol), dioxane (9 mL) and water (9 mL) to give a tan suspension. The reaction was heated to 100° C. for 18 hours. The reaction mixture was poured into water and neutralized by 1N HCl, extracted with EtOAc. The organic portion was evaporated to dryness and the residue was subjected to column chromatography (SiO₂, 1% methanol in methylene chloride) to yield the desired compound (2.42 g, 96%).

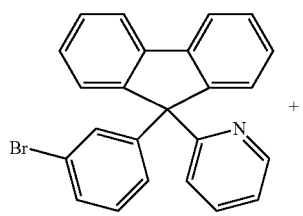
+

202

-continued

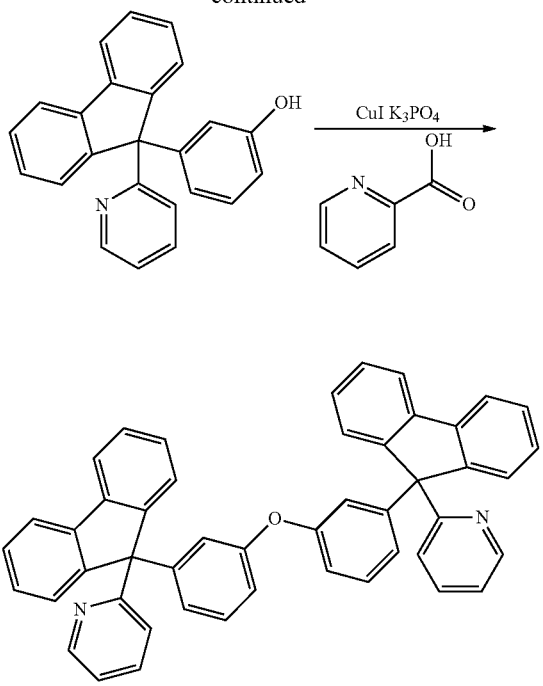

Synthesis of 2,2'-((oxybis(3,1-phenylene))bis(9H-fluorene-9,9-diyl))dipyridine In a 100 mL round-bottomed flask was added 2-(9-(3-bromophenyl)-9H-fluoren-9-yl)pyridine (2.42 g, 6.08 mmol), 3-(9-(pyridin-2-yl)-9H-fluoren-9-yl)phenol (2.038 g, 6.08 mmol), copper(I) iodide (0.231 g, 1.215 mmol), picolinic acid (0.299 g, 2.430 mmol), potassium phosphate (2.58 g, 12.15 mmol) and DMSO (50 mL) to give a brown solution. The reaction mixture was heated to 120° C. for 16 hours. The reaction was diluted with 10% lithium chloride solution and extracted with EtOAc. The organic portion was evaporated to dryness and the residue was subjected to column chromatography (SiO₂, 30% EtOAc in hexanes) to yield the desired product. (2 g, 50%)

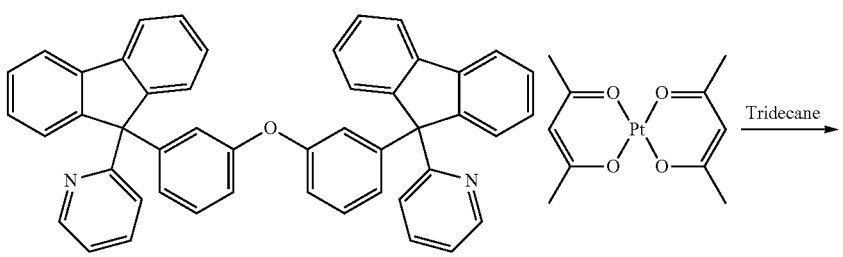

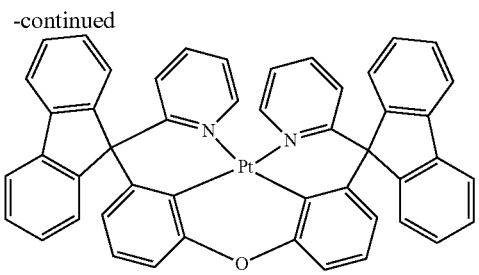

Synthesis of Compound 88

A 50 mL round-bottom flask was charged with 2,2'-((oxybis(3,1-phenylene))bis(9H-fluorene-9,9-diyl))dipyridine (0.3 g, 0.46 mmol) and Pt(acac)$_2$ (0.09 g, 0.23 mmol) and tridecane (10 drops). The reaction mixture was heated to 240° C. for 16 hours. The reaction mixture was subjected to column chromatography (SiO$_2$ pretreated with Et$_3$N 40% DCM in hexanes) to yield Compound 88 as a pink solid The product was confirmed by LC/MS and NMR.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

What is claimed is:

1. A compound having the formula:

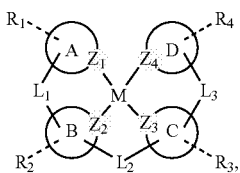

Formula I wherein A-L$_1$-B has a structure selected from the group consisting of:

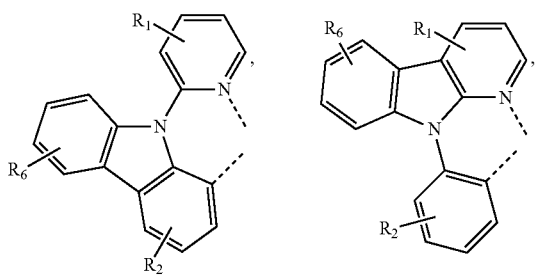

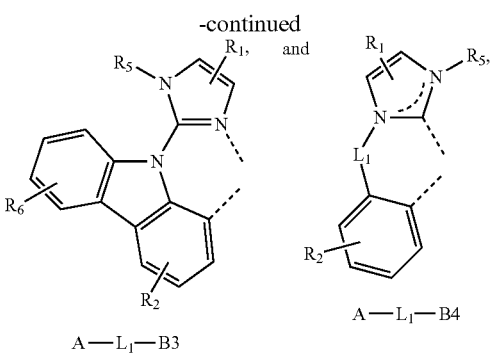

wherein C and D are each independently a 5- or 6-membered carbocyclic or heterocyclic ring;
wherein M is Pt or Pd;
wherein L$_3$ is selected from the group consisting of BR, NR, PR, CRR', SiRR', and GeRR';
wherein, in A-L$_1$-B4, L$_1$ is selected from the group consisting of BR, NR, PR, CRR', SiRR', and GeRR';
wherein L$_2$ is independently selected from the group consisting of BR, NR, PR, O, S, Se, C=O, S=O, SO$_2$, CRR', SiRR', and GeRR';
wherein each of Z$_3$ and Z$_4$ is carbon or nitrogen;
wherein R$_1$, R$_2$, R$_3$, R$_4$, and R$_6$ may represent no substitution up to the maximum available substitutions;
wherein R, R', R$_1$, R$_2$, R$_3$, R$_4$, R$_5$, and R$_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein, when present, each R and R' of L$_1$ is optionally joined to an adjacent substituent selected from the group consisting of R$_1$ and R$_2$ to form a fused ring,
wherein, when present, each R and R' of L$_2$ is optionally joined to an adjacent substituent selected from the group consisting of R$_2$ and R$_3$ to form a fused ring,
wherein, when present, each R and R' of L$_3$ is optionally joined to an adjacent substituent selected from the group consisting of R$_3$ and R$_4$ to form a fused ring,
wherein two or more adjacent R$_1$, R$_2$, R$_3$ and R$_4$ substituents on the same ring are optionally joined to form a fused ring, and
wherein, when the A-L$_1$-B structure is A-L$_1$-B4, at least one of the following applies:
(i) at least one fused ring is formed by joining (a) R or R' of L$_1$ to an adjacent substituent selected from the group consisting of R$_1$ and R$_2$, (b) R or R of L$_2$ to an adjacent substituent selected from the group consisting of R$_2$ and R₃, or (c) R or R' of L₃ to an adjacent substituent selected from the group consisting of R₃ and R₄, (ii) at least one of L₁ and L₃ is NR, (iii) and Z₄ are nitrogen atoms coordinated to metal atom M, and (iv) L₂ is selected from the group consisting of O, S, and NR.

2. The compound of claim 1, wherein the A-L₁-B structure is A-L₁-B4 and at least one fused ring is formed by joining R or R' of L₁ to an adjacent substituent selected from the group consisting of R₁ and R₂, R or R' of L₂ to an adjacent substituent selected from the group consisting of R₂ and R₃, or R or R' of L₃ to an adjacent substituent selected from the group consisting of R₃ and R₄.

3. The compound of claim 1, wherein at least one of L₁, L₂ and L₃ is NR.

4. The compound of claim 1, wherein L₁ and L₃ are NR.

5. The compound of claim 1, wherein the A-L₁-B structure is A-L₁-B4 and Z₄ are nitrogen atoms coordinated to metal atom M.

6. The compound of claim 1, wherein the A-L₁-B structure is A-L₁-B4 and Z₄ are carbon atoms coordinated to metal atom M.

7. The compound of claim 1, wherein M is Pt.

8. A compound having the formula:

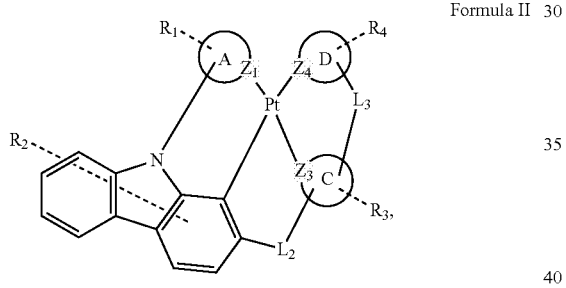

Formula II wherein A, C and D are each independently a 5- or 6-membered carbocyclic or heterocyclic ring;

wherein L₃ is independently selected from the group consisting of BR, NR, PR, CRR', SiRR', and GeRR';

wherein L₂ is independently selected from the group consisting of BR, NR, PR, O, S, Se, C=O, S=O, SO₂, CRR', SiRR', and GeRR';

wherein each of Z₁, Z₃ and Z₄ is carbon or nitrogen;

wherein R₁, R₂, R₃ and R₄, may represent no substitution, up to the maximum available substitutions;

wherein R, R', R₁, R₂, R₃, and R₄ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein, when present, each R and R' of L₂ is optionally joined to an adjacent substituent selected from the group consisting of R₂ and R₃ to form a fused ring, wherein, when present, each R and R' of L₃ is optionally joined to an adjacent substituent selected from the group consisting of R₃ and R₄ to forth a fused ring, and wherein two or more adjacent R₁, R₂, R₃ and R₄ substituents on the same ring are optionally joined to form a fused ring.

9. The compound of claim 8, wherein the compound has the formula:

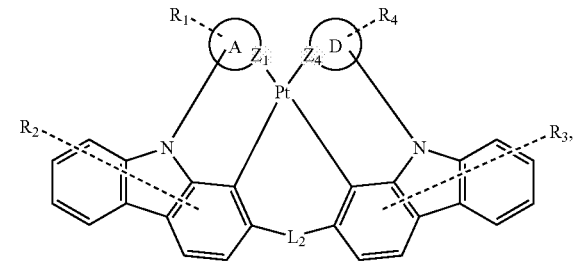

Formula III.

10. The compound of claim 1, wherein the compound has the formula:

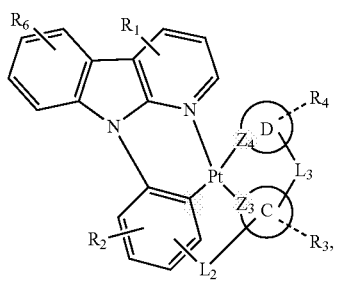

Formula IV.

11. The compound of claim 10, wherein the compound has the formula:

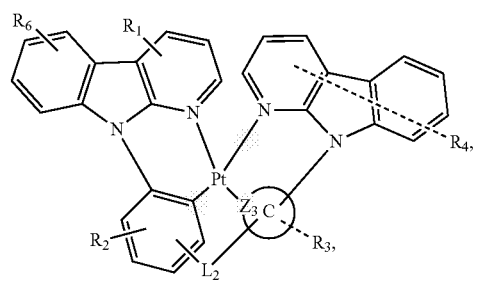

Formula V.

12. The compound of claim 1, wherein the compound is selected from the group consisting of:

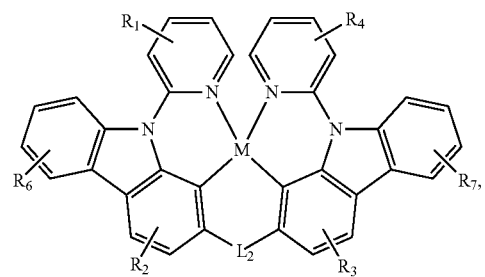

207
-continued

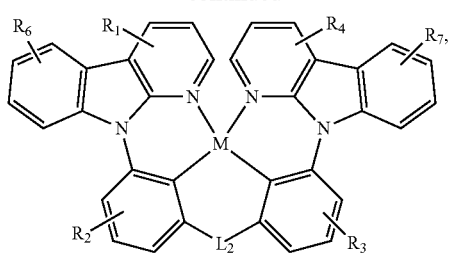

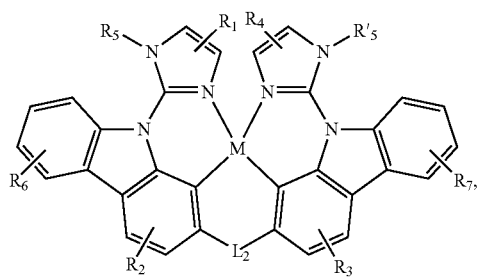

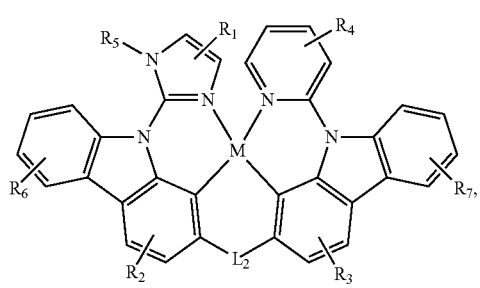

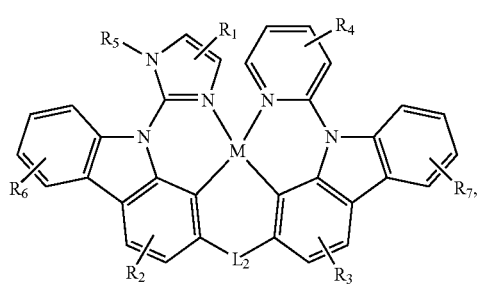

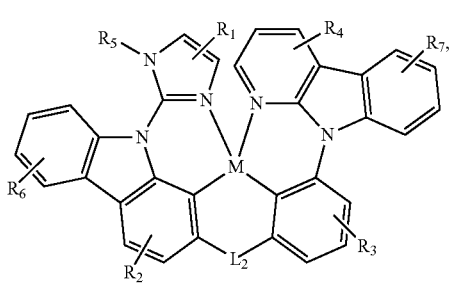

208
-continued

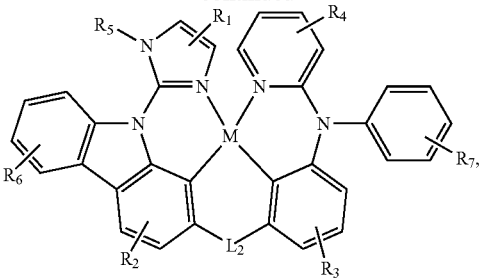

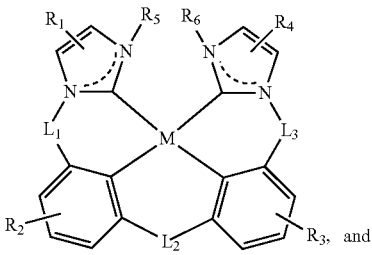

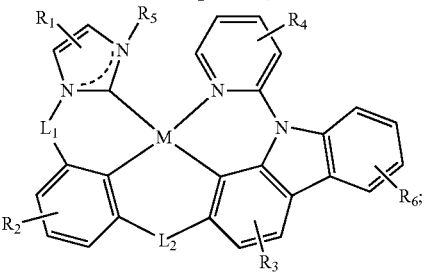

wherein $R_5$, $R'_5$, $R_6$, and $R_7$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfanyl, sulfonyl, phosphino, and combinations thereof.

13. The compound of claim 1, wherein $L_2$ is independently selected from the group consisting of O, S, and NR.

14. The compound of claim 13, wherein $L_2$ is NR, and R is phenyl or substituted phenyl.

15. The compound of claim 13, wherein $L_2$ is O.

16. The compound of claim 1, wherein $Z_1$ and $Z_4$ are nitrogen atoms.

17. A compound selected from the group consisting of compounds 1-24, 34-115, 121-129 and 131, wherein compounds 1-24, 34-115, 121-129 and 131 have the following structures:

Compound 1

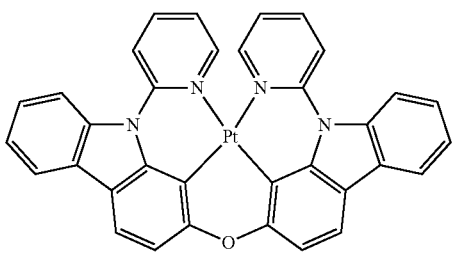

-continued
Compound 2
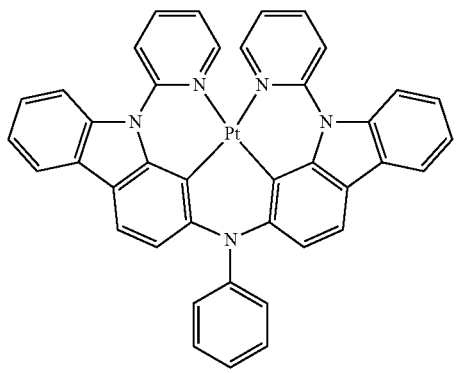
Compound 3
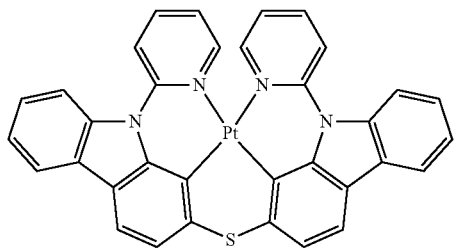
Compound 4
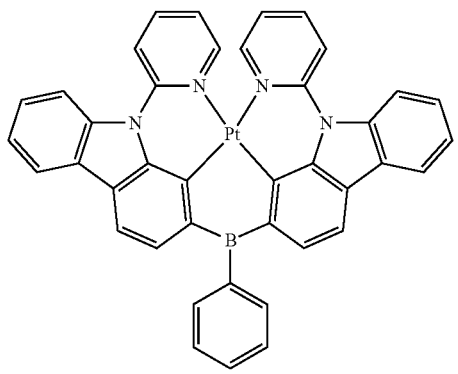
Compound 5
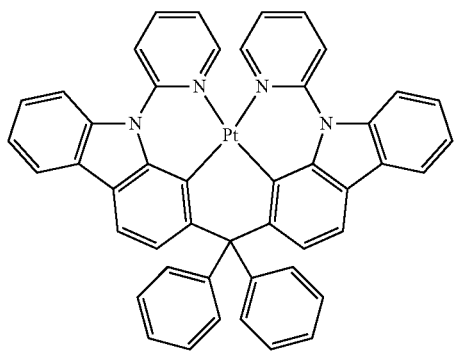
-continued
Compound 6
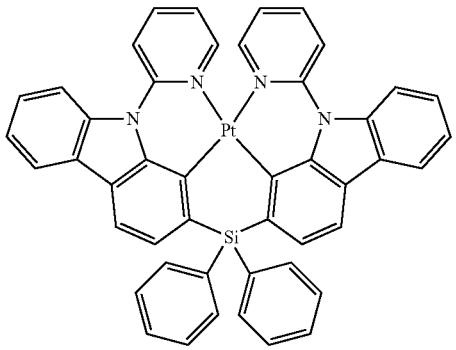
Compound 7
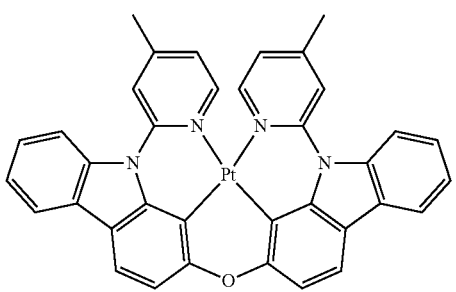
Compound 8
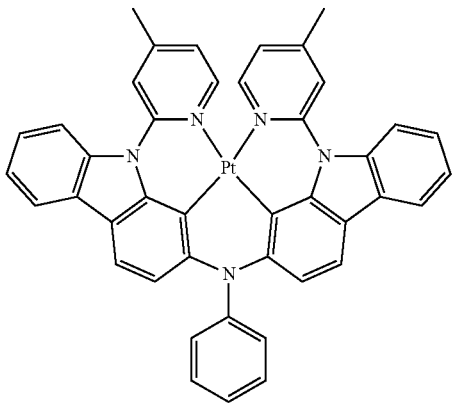
Compound 9
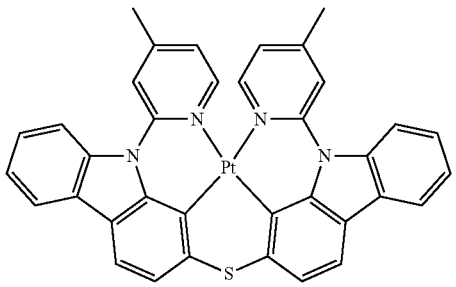

-continued
Compound 10
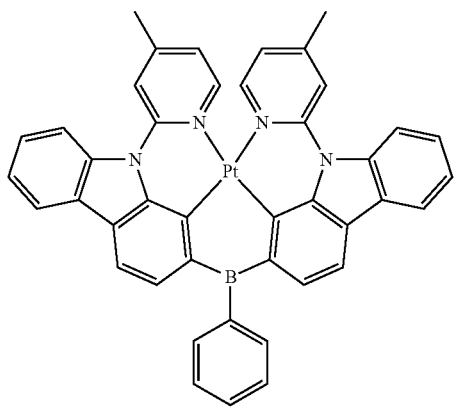
Compound 11
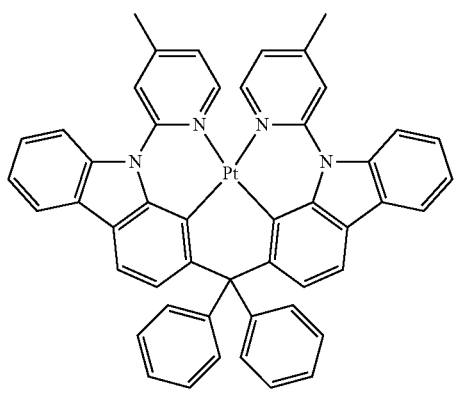
Compound 12
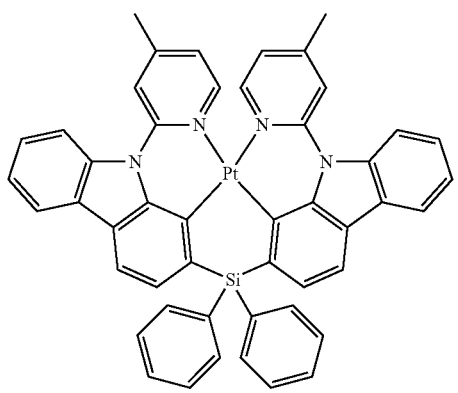
Compound 13
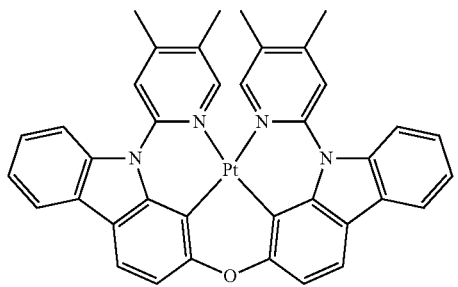
-continued
Compound 14
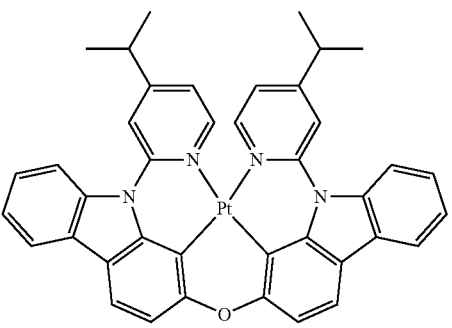
Compound 15
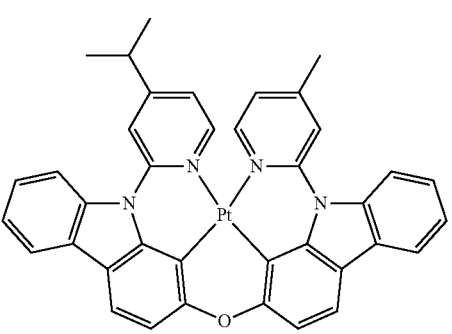
Compound 16
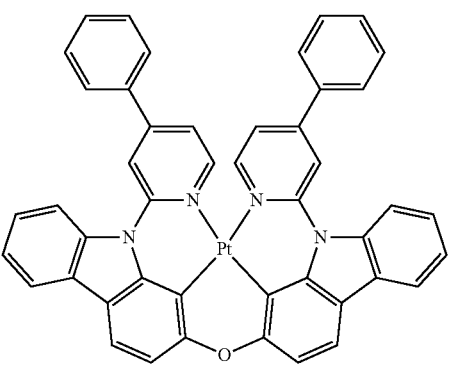
Compound 17
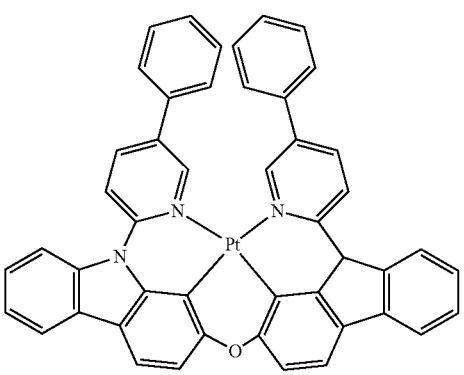

-continued
Compound 18
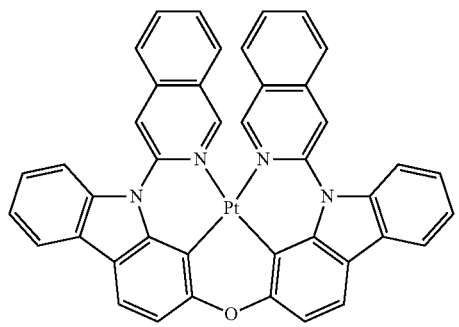
Compound 19
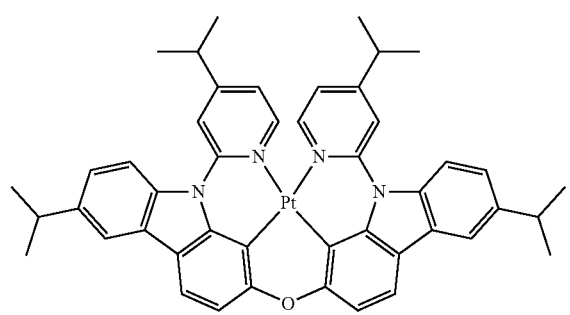
Compound 20
Compound 21
Compound 22
-continued
Compound 23
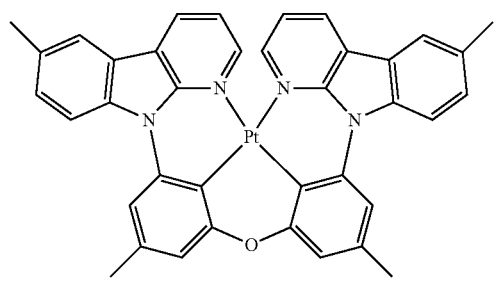
Compound 24
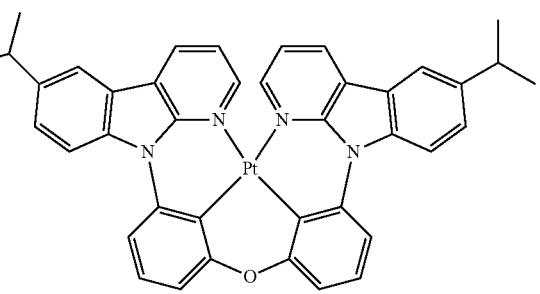
Compound 25
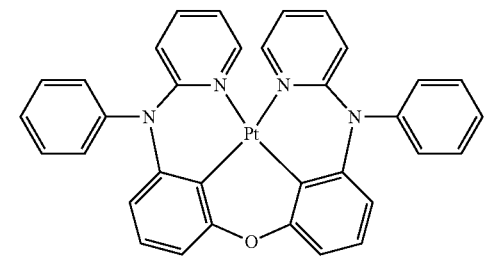
Compound 34
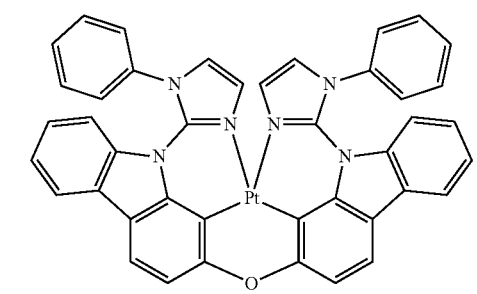
Compound 35
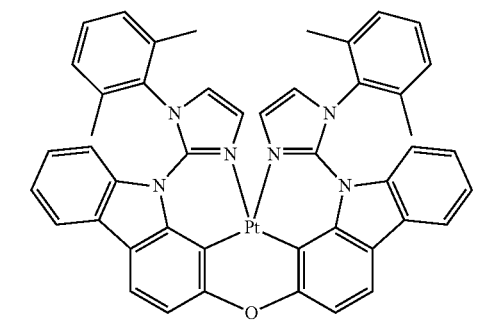

Compound 36
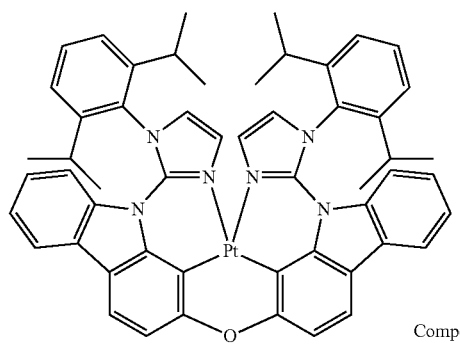
Compound 37
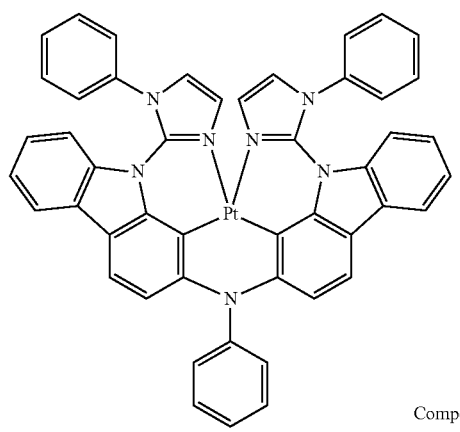
Compound 38
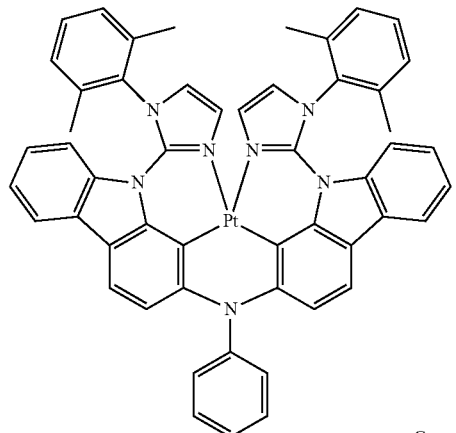
Compound 39
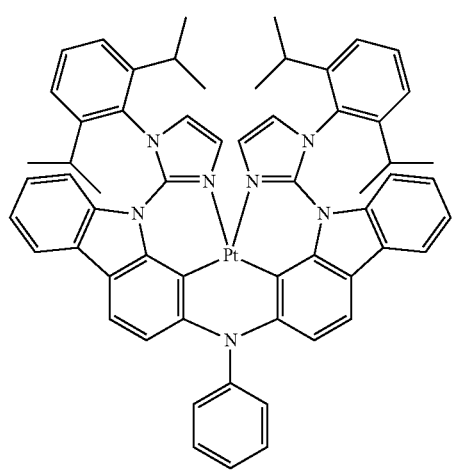
Compound 40
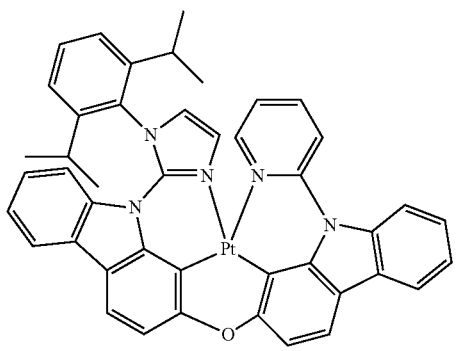
Compound 41
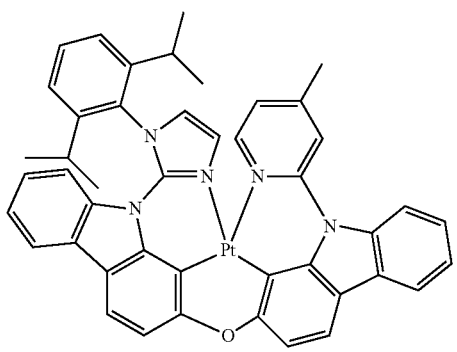
Compound 42
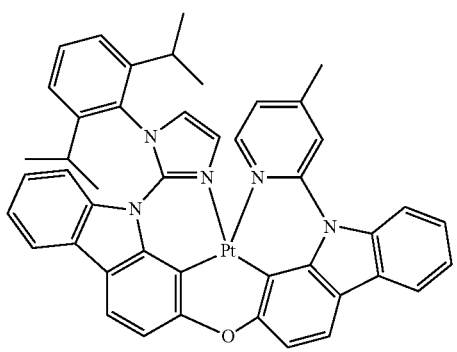
Compound 43
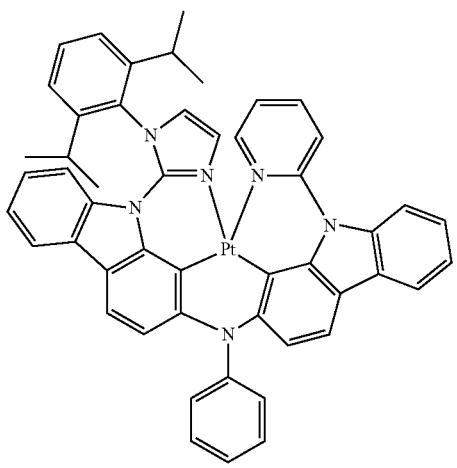

Compound 44
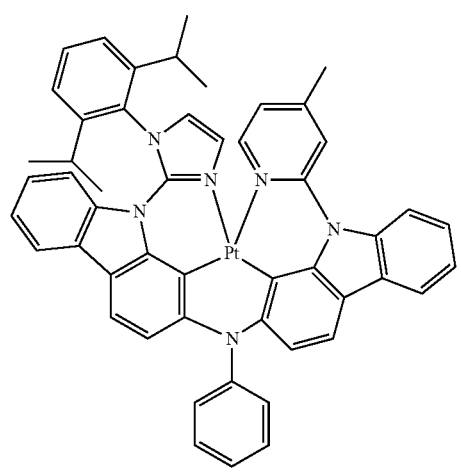
Compound 45
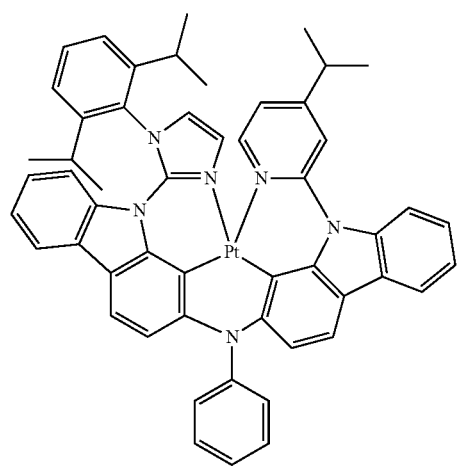
Compound 46
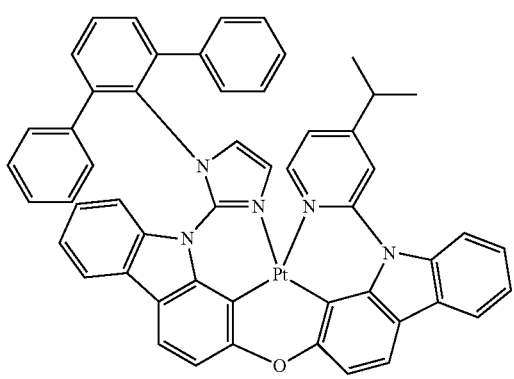
Compound 47
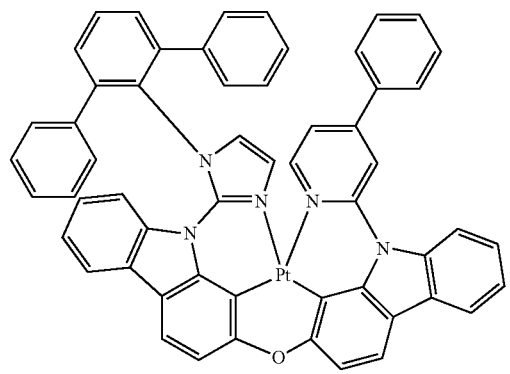
Compound 48
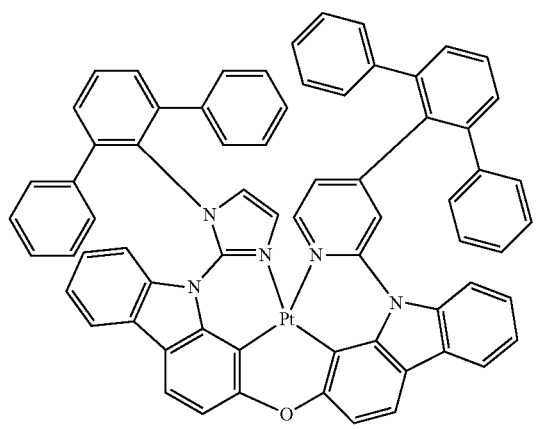
Compound 49
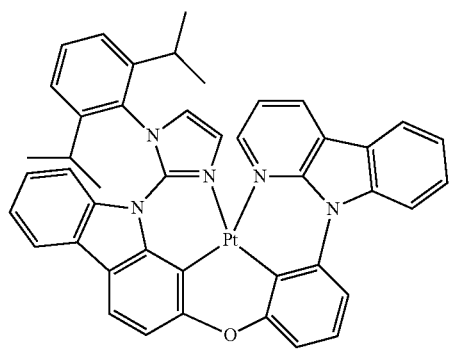
Compound 50
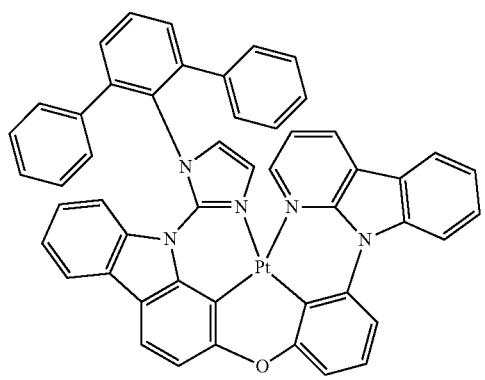

-continued
Compound 51
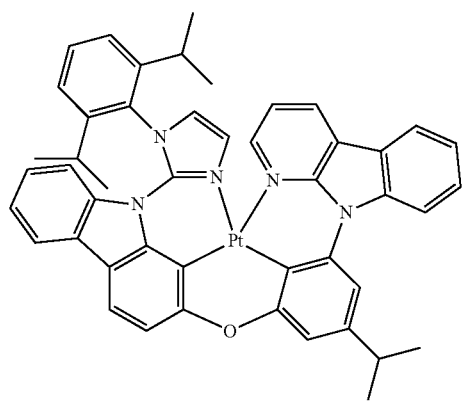
Compound 52
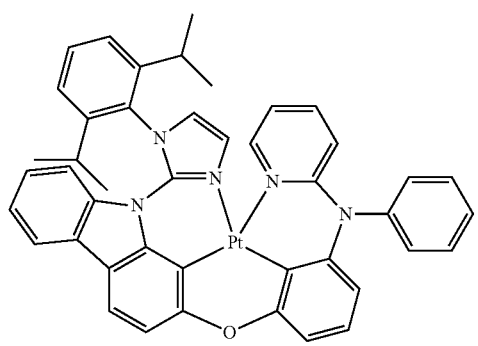
Compound 53
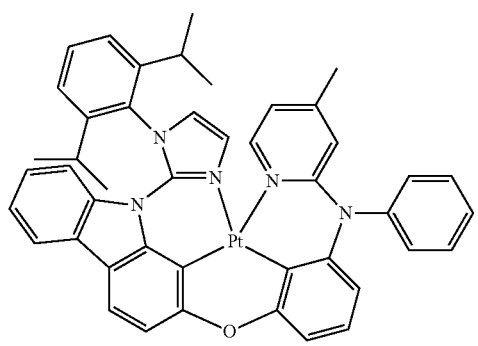
Compound 54
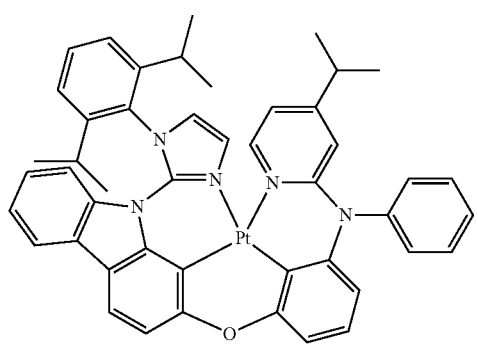
-continued
Compound 55
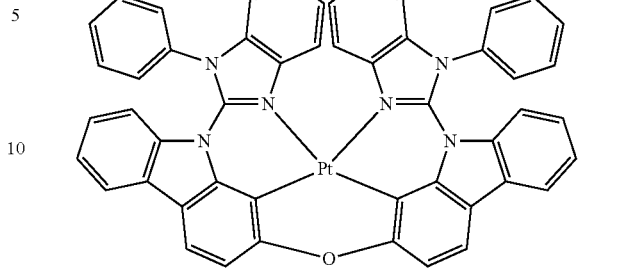
Compound 56
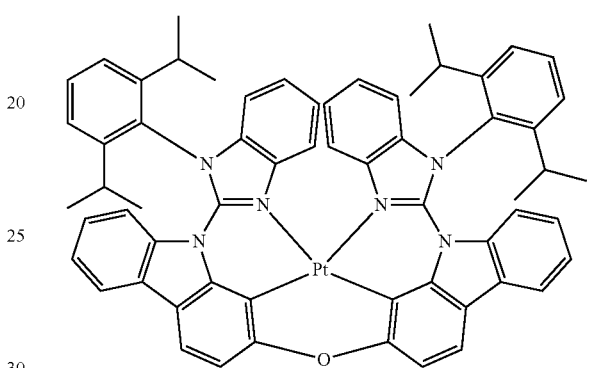
Compound 57
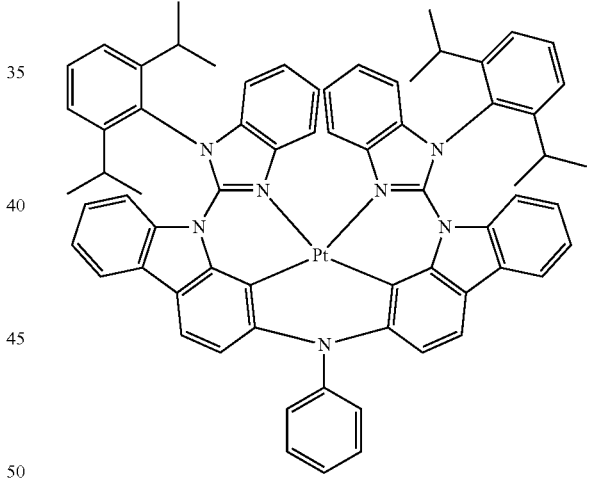
Compound 58
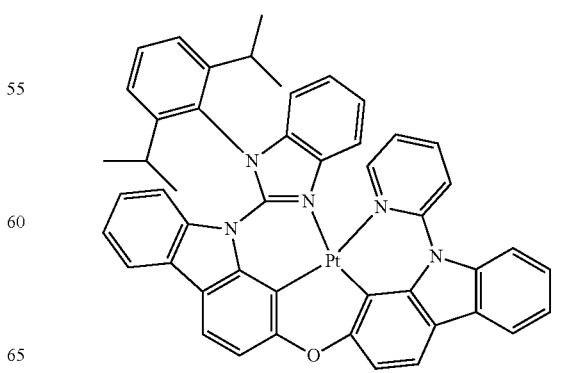

Compound 59
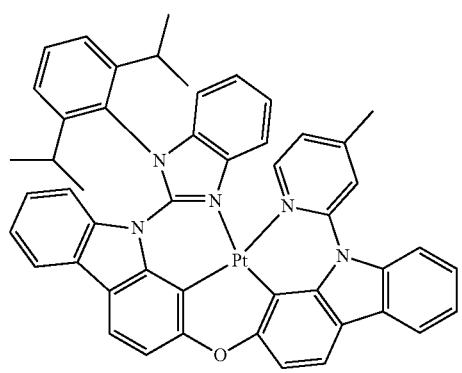
Compound 60
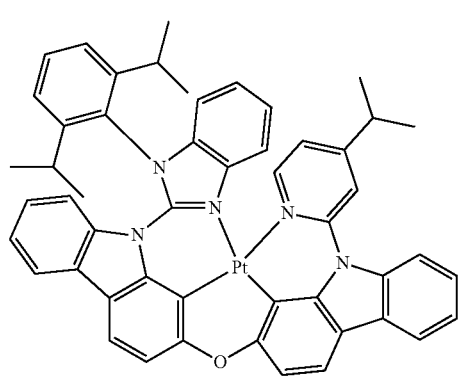
Compound 61
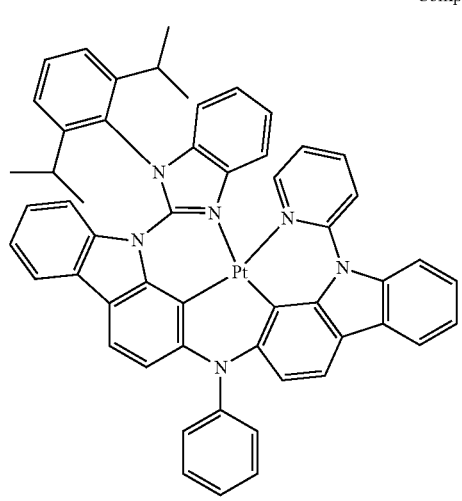
Compound 62
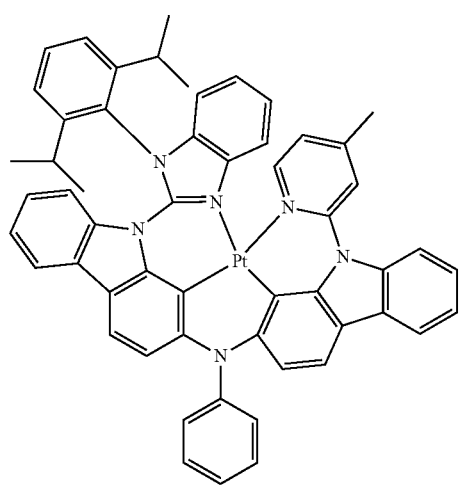
Compound 63
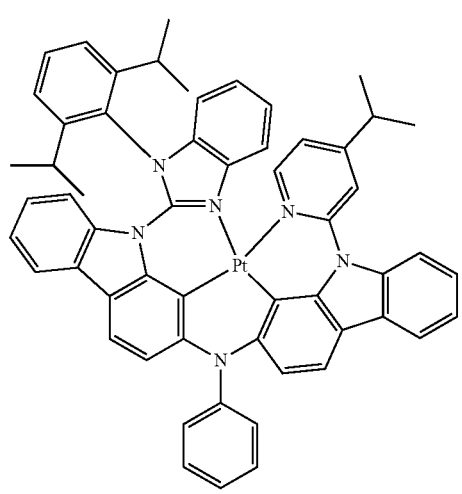
Compound 64
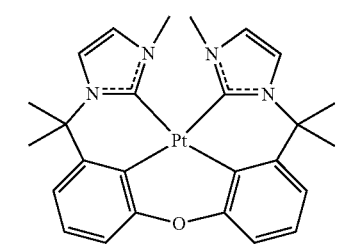
Compound 65
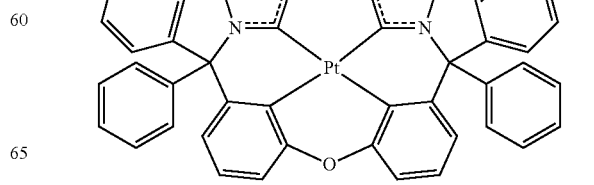

Compound 66
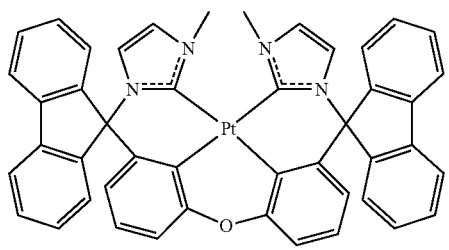
Compound 67
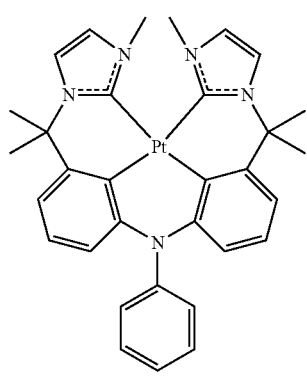
Compound 68
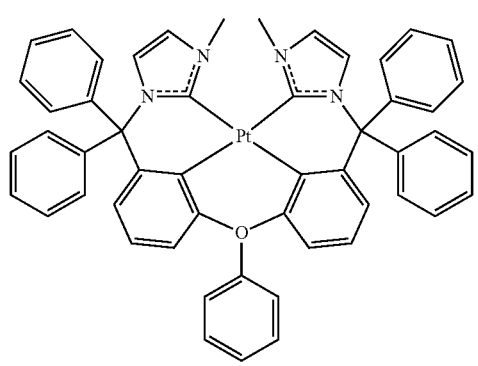
Compound 69
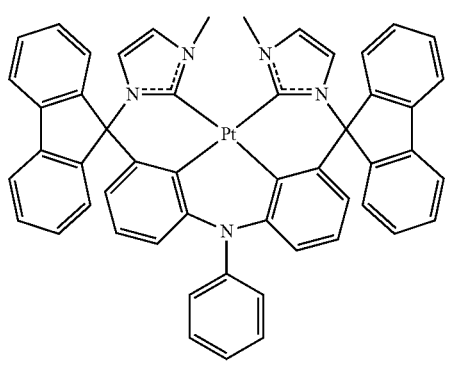
Compound 70
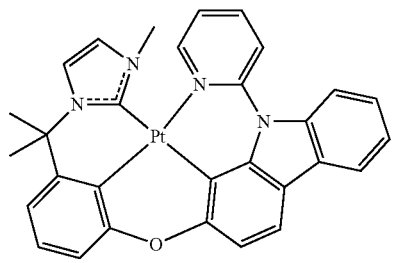
Compound 71
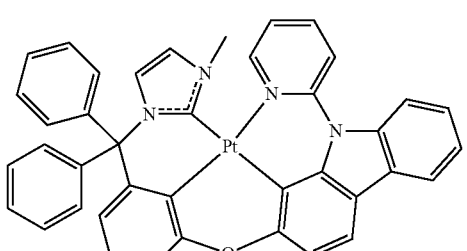
Compound 72
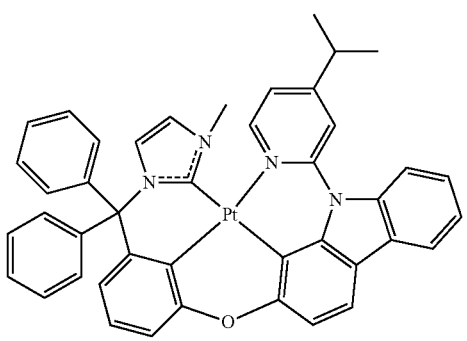
Compound 73
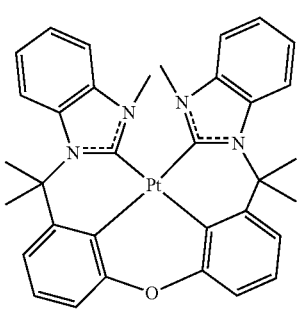
Compound 74
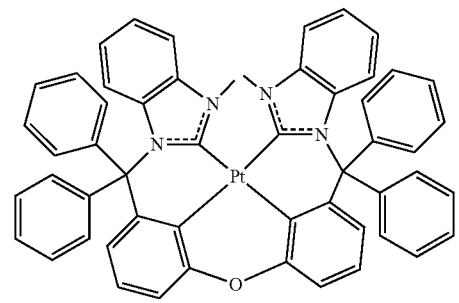

Compound 75
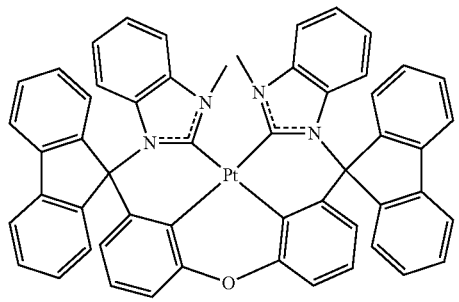
Compound 76
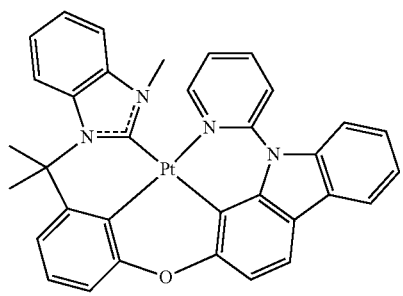
Compound 77
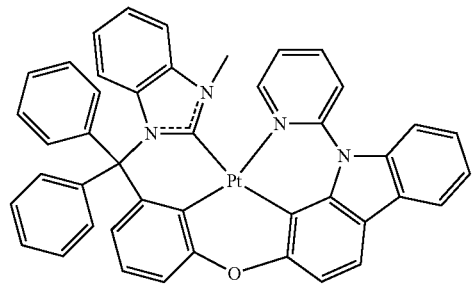
Compound 78
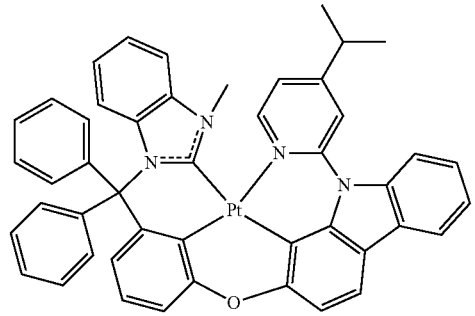
Compound 79
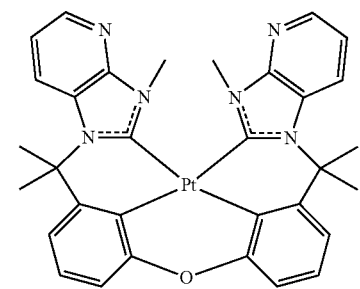
Compound 80
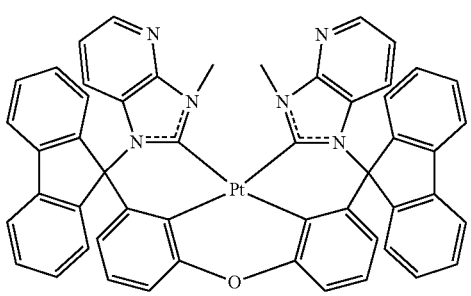
Compound 81
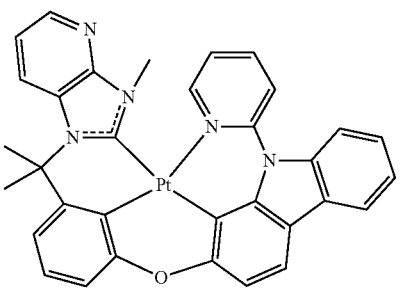
Compound 82
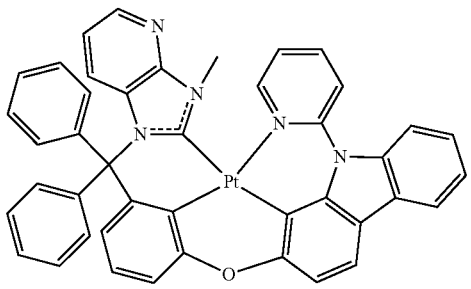
Compound 83
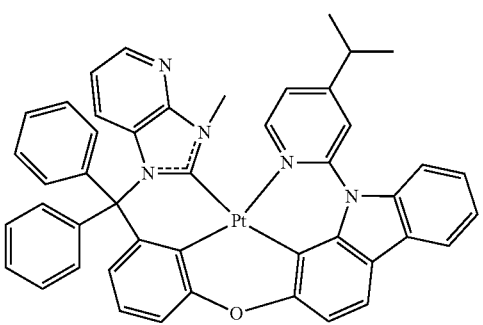
Compound 84

Compound 85
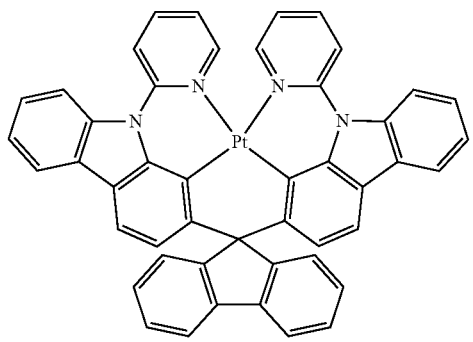
Compound 89
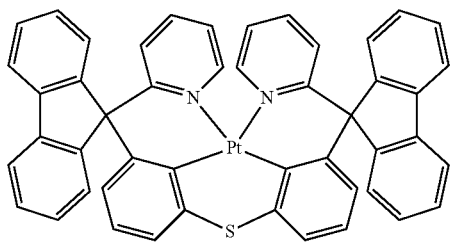
Compound 86
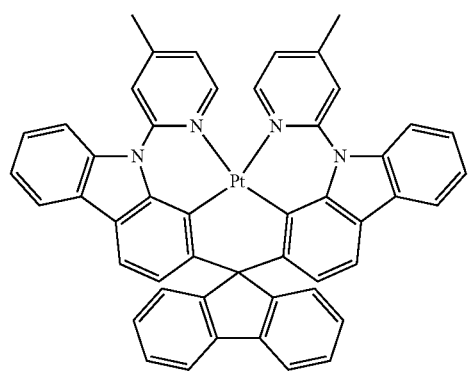
Compound 90
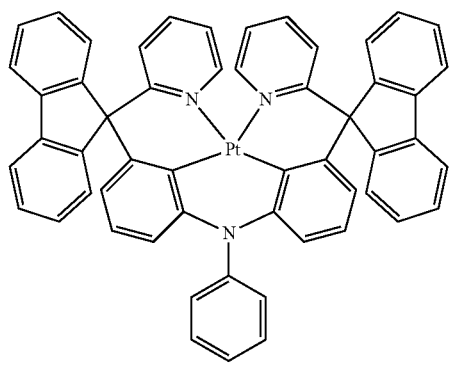
Compound 87
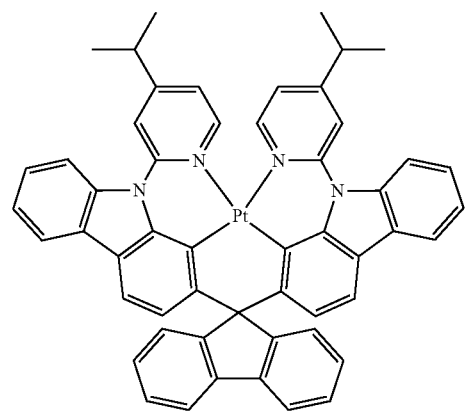
Compound 91
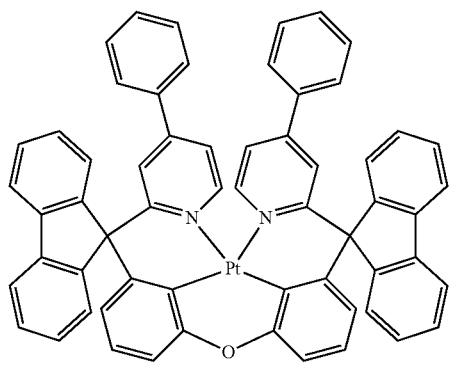
Compound 88
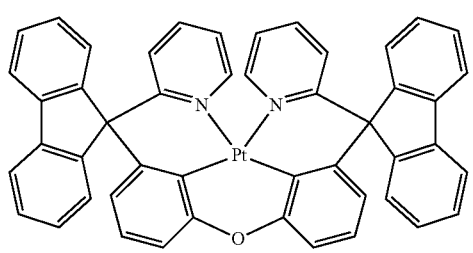
Compound 92
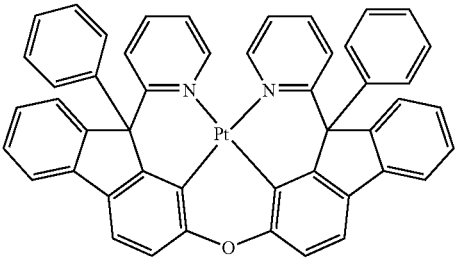

Compound 93
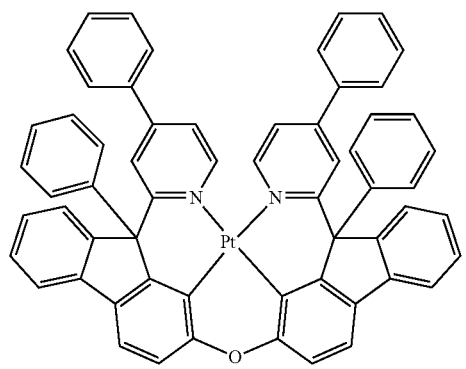
Compound 94
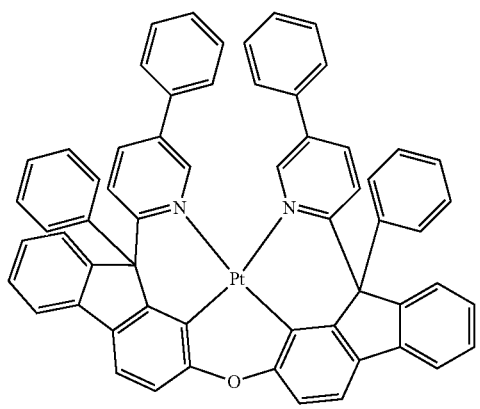
Compound 95
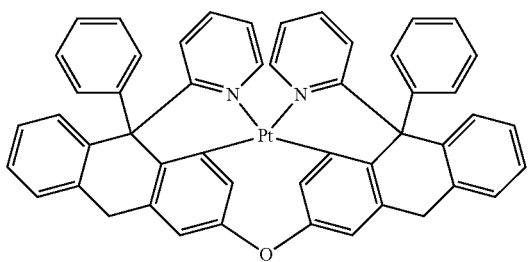
Compound 96
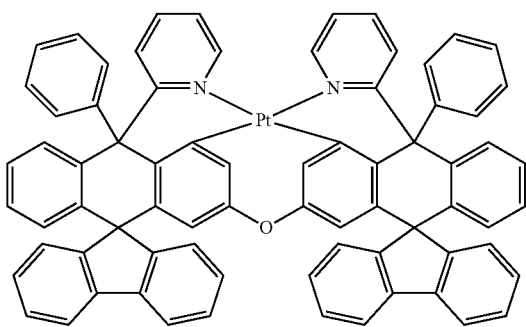
Compound 97
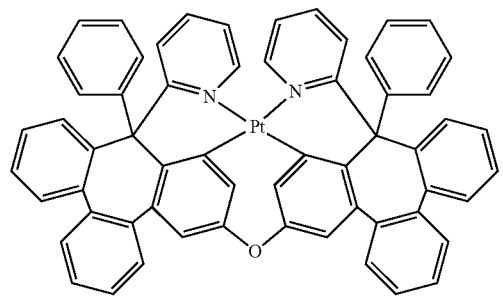
Compound 98
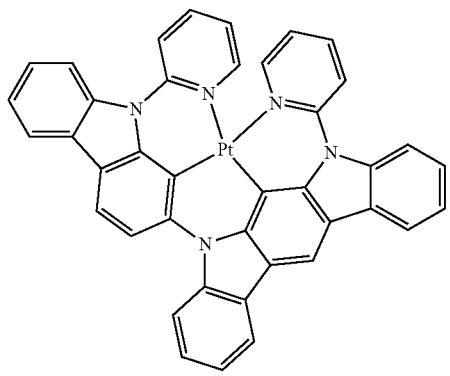
Compound 99
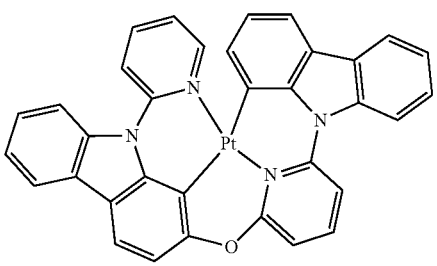
Compound 100
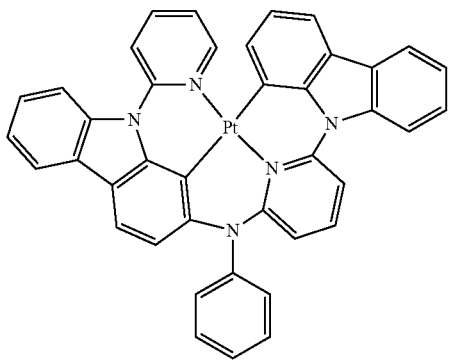

Compound 101
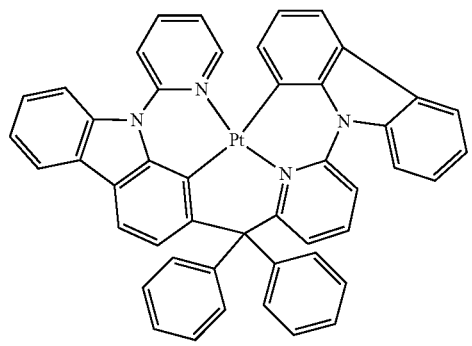
Compound 102
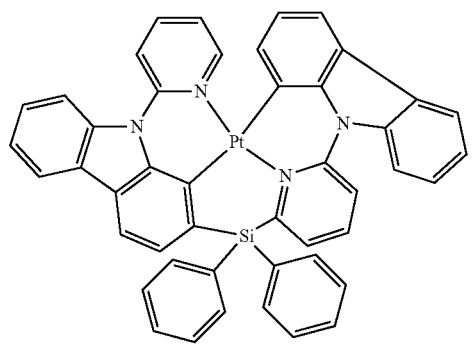
Compound 103
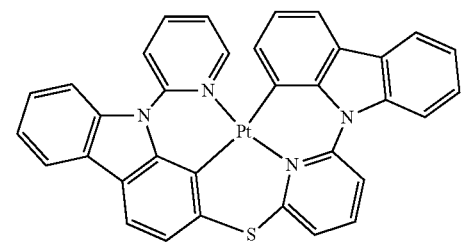
Compound 104
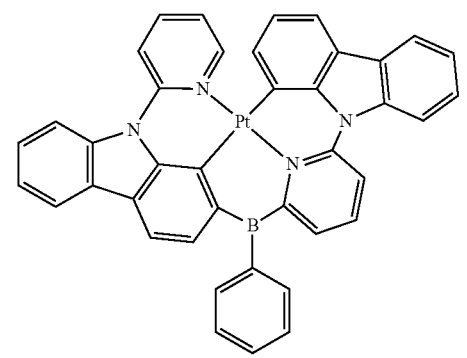
Compound 105
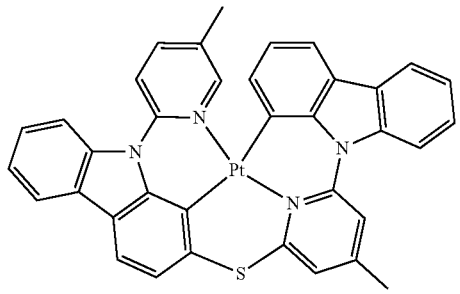
Compound 106
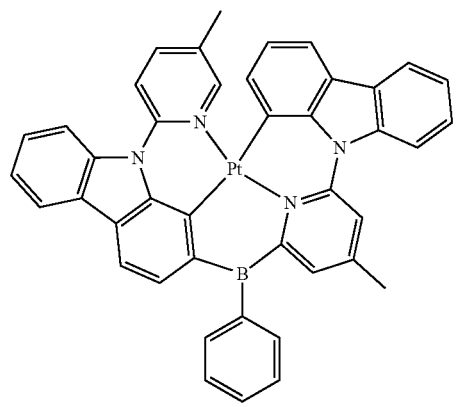
Compound 107
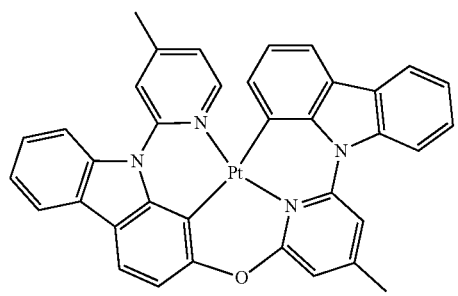
Compound 108
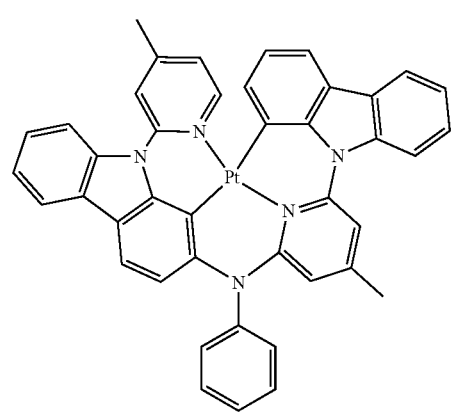

Compound 109
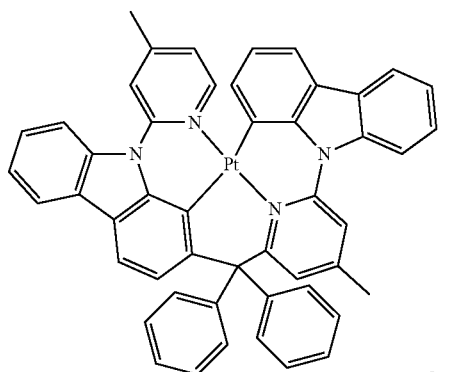
Compound 110
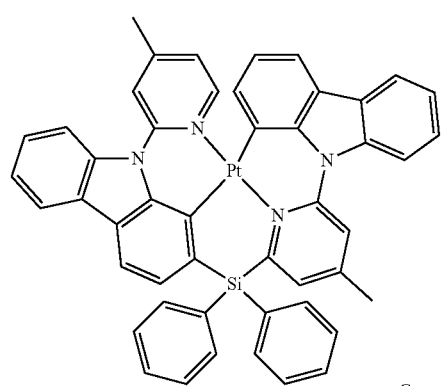
Compound 111
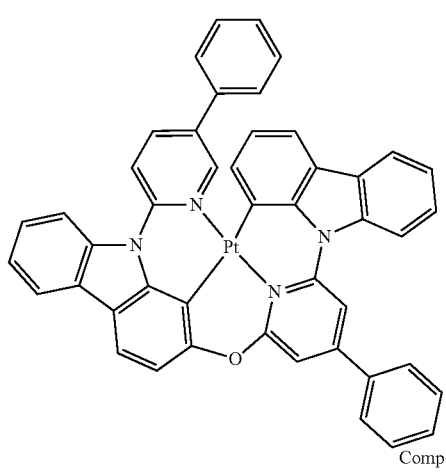
Compound 112
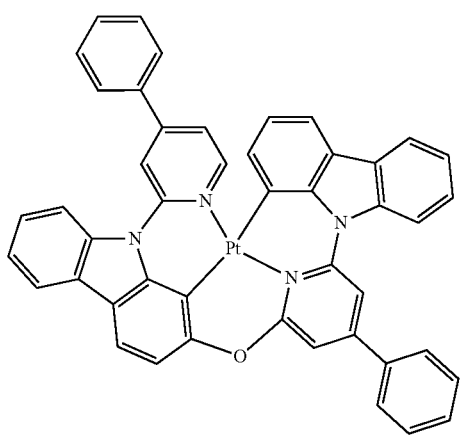
Compound 113
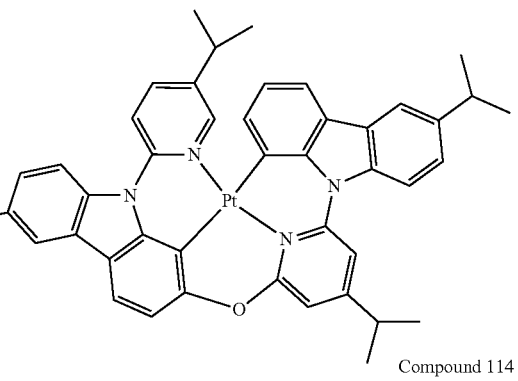
Compound 114
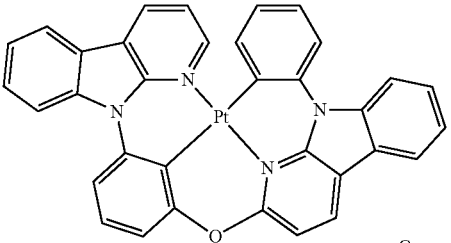
Compound 115
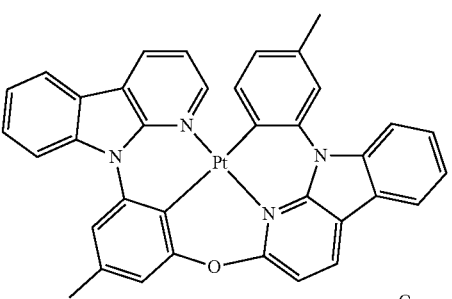
Compound 121
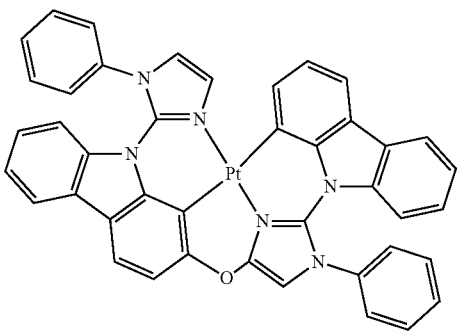
Compound 122
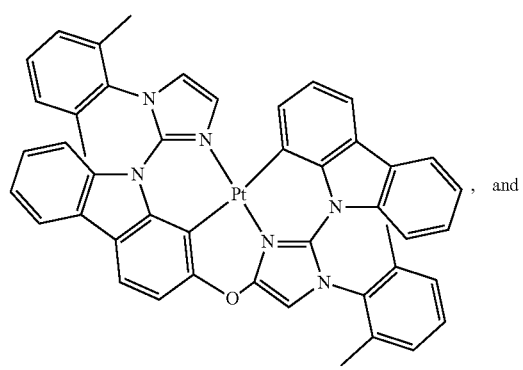
, and -continued
Compound 123
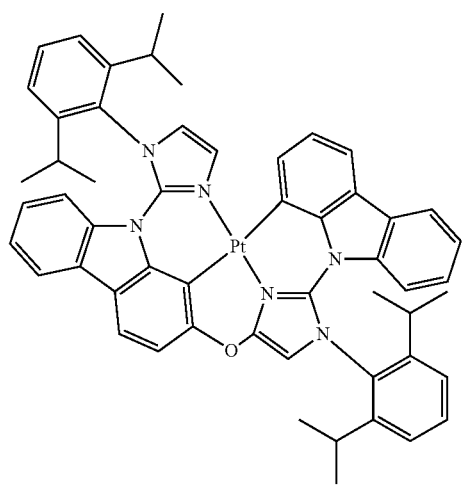
Compound 124
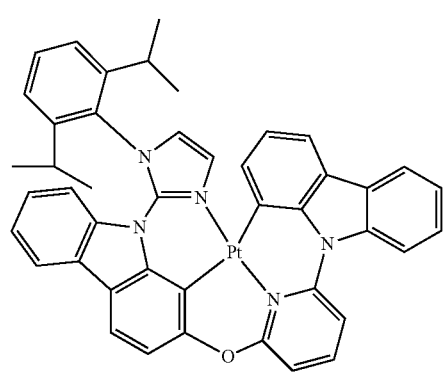
Compound 125
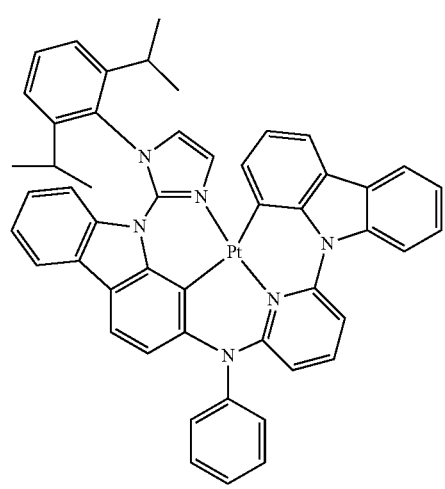
-continued
Compound 126
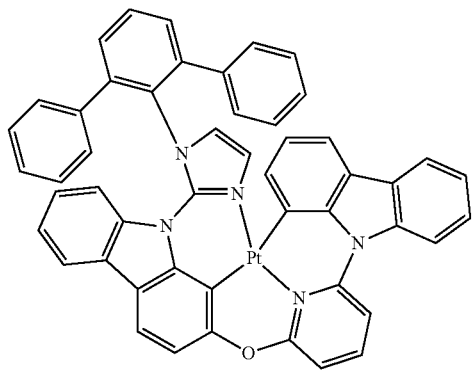
Compound 127
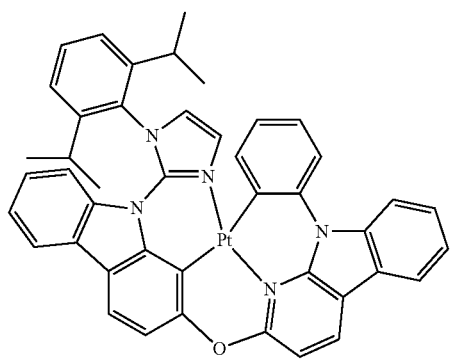
Compound 128
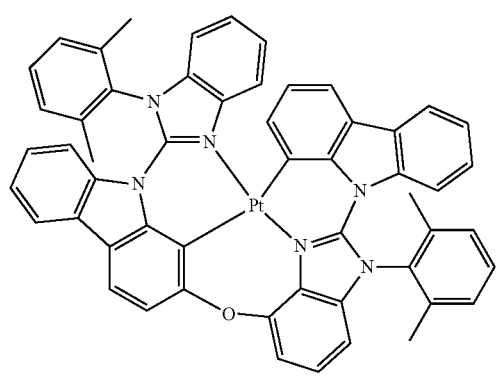
Compound 129
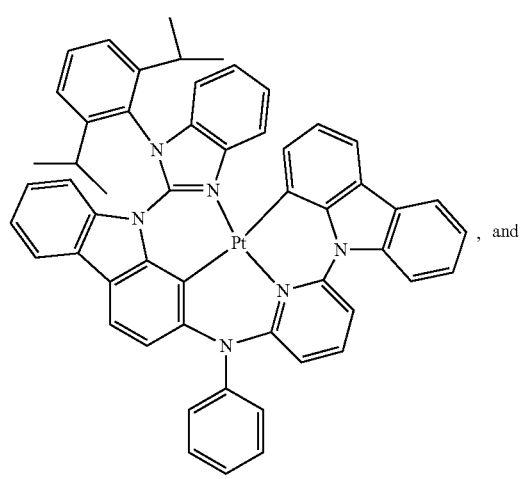
, and -continued Compound 131

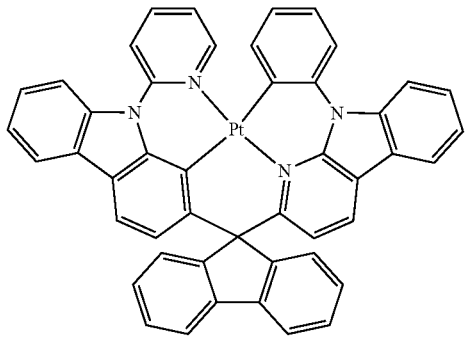

18. A first device comprising a first organic light emitting device, comprising:
an anode;
a cathode; and
an organic layer, disposed between the anode and the cathode, comprising a compound having the formula:

Formula I,

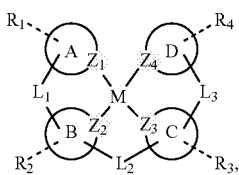

wherein A-$L_1$-B has a structure selected from the group consisting of:

Formula I

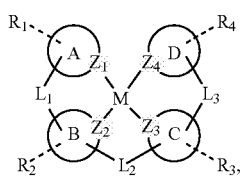

wherein C and D are each independently a 5- or 6-membered carbocyclic or heterocyclic ring;
wherein M is Pt or Pd;
wherein $L_3$ is selected from the group consisting of BR, NR, PR, CRR', SiRR', and GeRR';
wherein, in A-$L_1$-B4, $L_1$ is selected from the group consisting of BR, NR, PR, CRR', SiRR', and GeRR';
wherein $L_2$ is independently selected from the group consisting of BR, NR, PR, O, S, Se, C=O, S=O, $SO_2$, CRR', SiRR', and GeRR';
wherein each of $Z_3$ and $Z_4$ is carbon or nitrogen;
wherein $R_1$, $R_2$, $R_3$, $R_4$, and $R_6$ may represent no substitution up to the maximum available substitutions;
wherein R, $R_1$, $R_2$, $R_3$, $R_4$, $R_5$, and $R_6$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein, when present, each R and R' of $L_1$ is optionally joined to an adjacent substituent selected from the group consisting of $R_1$ and $R_2$ to form a fused ring,
wherein, when present, each R and R' of $L_2$ is optionally joined to an adjacent substituent selected from the group consisting of $R_2$ and $R_3$ to form a fused ring,
wherein, when present, each R and R' of $L_3$ is optionally joined to an adjacent substituent selected from the group consisting of $R_3$ and $R_4$ to form a fused ring,
wherein two or more adjacent $R_1$, $R_2$, $R_3$ and $R_4$ substituents on the same ring are optionally joined to form a fused ring, and
wherein, when the A-$L_1$-B structure is A-$L_1$-B4, at least one of the following applies:
(i) at least one fused ring is formed by joining (a) R or R' of $L_1$ to an adjacent substituent selected from the group consisting of $R_1$ and $R_2$, (b) R or R' of $L_2$ to an adjacent substituent selected from the group consisting of $R_2$ and $R_3$, or (c) R or R' of $L_3$ to an adjacent substituent selected from the group consisting of $R_3$ and $R_4$,
(ii) at least one of $L_1$ and $L_3$ is NR,
(iii) and $Z_4$ are nitrogen atoms coordinated to metal atom M, and
(iv) $L_2$ is selected from the group consisting of O, S, and NR.

19. The first device of claim 18, wherein the first device is a consumer product.
20. The first device of claim 18, wherein the first device is an organic light-emitting device.
21. The first device of claim 18, wherein the first device comprises a lighting panel.
22. The first device of claim 18, wherein the organic layer is an emissive layer and the compound is an emissive dopant.
23. The first device of claim 18, wherein the organic layer is an emissive layer and the compound is an non-emissive dopant.
24. The first device of claim 18, wherein the organic layer further comprises a host.
25. The first device of claim 24, wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C$C_nH_{2n+1}$, $Ar_1$, $Ar_1$—$Ar_2$, and $C_nH_{2n}$—$Ar_1$;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.
26. The first device of claim 25, wherein the host comprises one or more compounds having the formula:

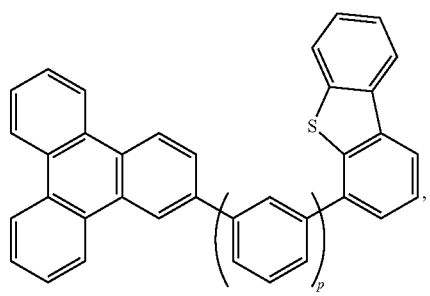

wherein p is 0 or 1.

27. The first device of claim 25, wherein the host comprises a metal complex.
28. The first device of claim 24, wherein the host is selected from the group consisting of
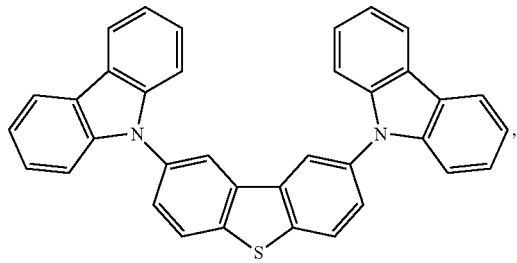,
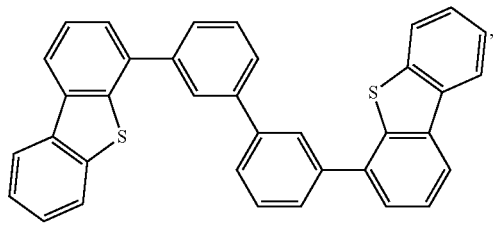,
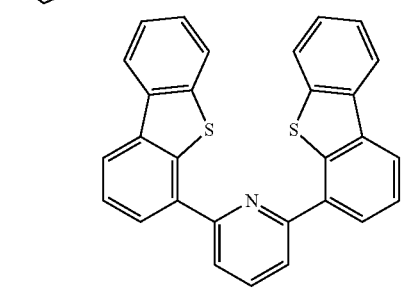,
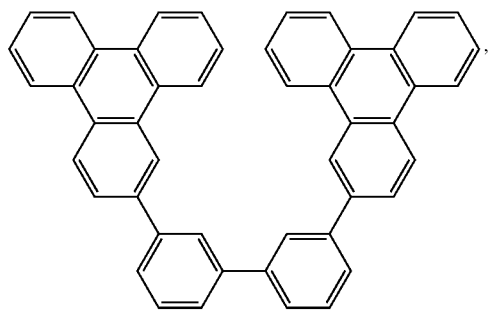,
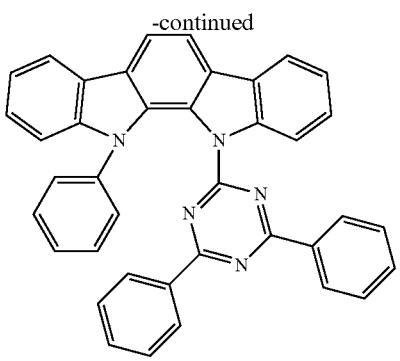,
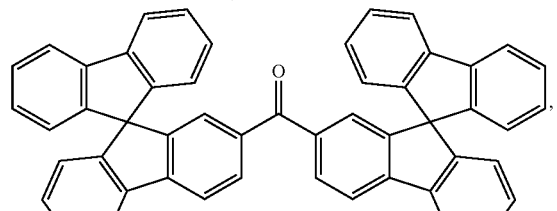,
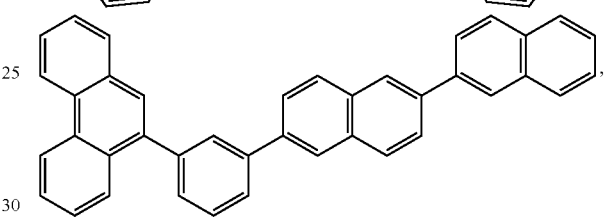,
and combinations thereof.
29. The compound of claim 1, wherein A-L$_1$-B is
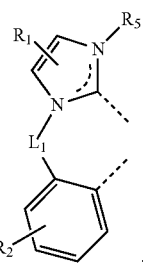.
* * * * *

UNITED STATES PATENT AND TRADEMARK OFFICE
CERTIFICATE OF CORRECTION

PATENT NO. : 9,461,254 B2  Page 1 of 3
APPLICATION NO. : 13/732502
DATED : October 4, 2016
INVENTOR(S) : Jui-Yi Tsai et al.

It is certified that error appears in the above-identified patent and that said Letters Patent is hereby corrected as shown below:

In the Specification

Column 201, Lines 1-26, please delete

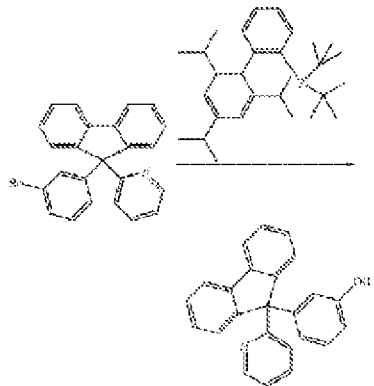

" and insert

Signed and Sealed this
Twentieth Day of June, 2017

Joseph Matal
*Performing the Functions and Duties of the
Under Secretary of Commerce for Intellectual Property and
Director of the United States Patent and Trademark Office*

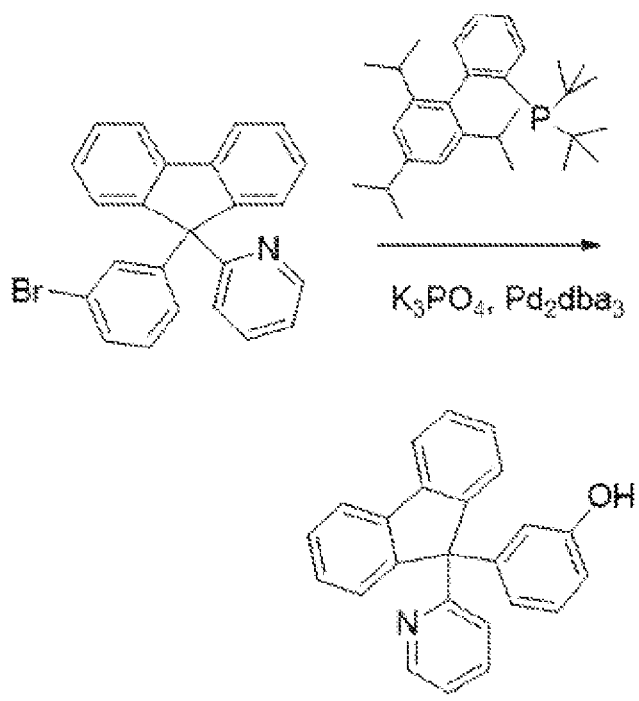
-- --
In the Claims
Column 204, Line 66, replace "(b) R or R" with -- (b) R or R' --
Column 205, Line 4, after "(iii)," please insert -- $Z_3$ --
Column 205, Line 21, after "and," please insert -- $Z_3$ and --
Column 205, Line 24, after "and," please insert -- $Z_3$ and --
Column 214, Lines 29-39, please delete
" 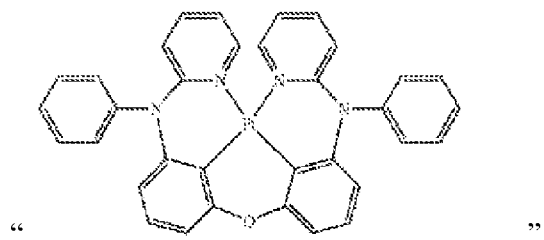 "

CERTIFICATE OF CORRECTION (continued)
U.S. Pat. No. 9,461,254 B2

Column 237, Lines 38-47, please delete

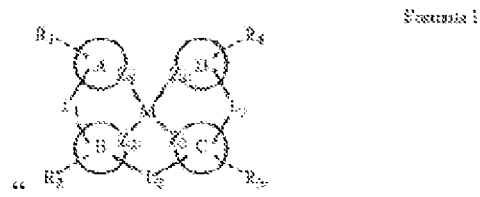

" and insert

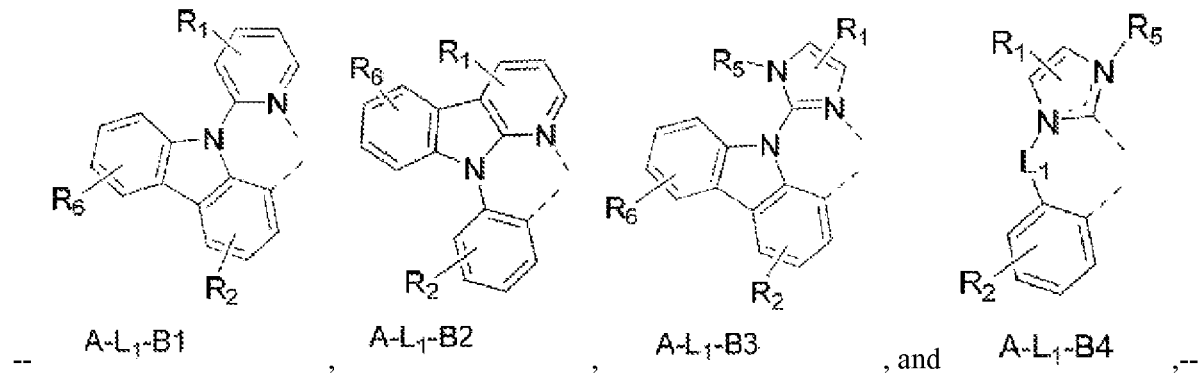

Column 237, Line 61, after "wherein R", please insert -- R', --

Column 238, Line 21, after "(iii)", please insert -- $Z_3$ --